US007981888B2

(12) United States Patent
Song et al.

(10) Patent No.: US 7,981,888 B2
(45) Date of Patent: *Jul. 19, 2011

(54) 1-OXYALKYL-2-CARBOXYL-7-NONSUBSTITUTED INDOLE DERIVATIVES

(75) Inventors: Xiaohong Song, Grayslake, IL (US); Hong Ding, Gurnee, IL (US); Steven W. Elmore, Northbrook, IL (US); Milan Bruncko, Green Oaks, IL (US); David J. Madar, Gilbert, AZ (US); Andrew J. Souers, Evanston, IL (US); Cheol-Min Park, Singapore (KR); Zhi-Fu Tao, Gurnee, IL (US); Xilu Wang, Grayslake, IL (US); Aaron R. Kunzer, Shaumburg, IL (US)

(73) Assignee: Abbott Laboratories, Abbott Park, IL (US)

( * ) Notice: Subject to any disclaimer, the term of this patent is extended or adjusted under 35 U.S.C. 154(b) by 251 days.

This patent is subject to a terminal disclaimer.

(21) Appl. No.: 12/104,319

(22) Filed: Apr. 16, 2008

(65) Prior Publication Data

US 2009/0124616 A1    May 14, 2009

Related U.S. Application Data

(60) Provisional application No. 60/949,683, filed on Jul. 13, 2007, provisional application No. 60/912,049, filed on Apr. 16, 2007.

(51) Int. Cl.
    *A61K 31/535*    (2006.01)
(52) U.S. Cl. ..................... 514/235.2; 514/326; 514/415; 546/201; 544/143; 548/483
(58) Field of Classification Search ................... 514/326, 514/235.2, 415; 546/201; 544/143; 548/483
    See application file for complete search history.

(56) References Cited

U.S. PATENT DOCUMENTS

| 4,994,477 | A | 2/1991 | Kempf |
| 6,787,651 | B2 * | 9/2004 | Stolle et al. ..................... 544/143 |
| 7,268,159 | B2 * | 9/2007 | Hu et al. ......................... 514/419 |
| 2006/0160879 | A1 * | 7/2006 | Olofsson et al. ............... 514/414 |

FOREIGN PATENT DOCUMENTS

| WO | 2006041961 A1 | 4/2006 |
| WO | 2006/061493 A1 | 6/2006 |

OTHER PUBLICATIONS

Amundson, Sally, "An Informatics approach Identifying Markers of Chemosensitivity in Human Cancer Cell Lines", Cancer Research, vol. 60, pp. 6101-6110, Nov. 2000.
Backus, Annals of Oncology: Official Journal of the European Society for Medical Oncology/ESMO 2001, vol. 12, pp. 779-785, 2001.
Baekelandt, M., "Expression of apoptosis-Related Proteins Is an Independent Determinant of Patient Prognosis in Advanced Ovarian Cancer", J Clin. Oncol., vol. 18, pp. 3775-3781, 2000.
Chung, T, "Expression of apoptotic regulators and their significance in cervical cancer", Cancer Letters, vol. 180, pp. 63-68, 2002.
Deininger, Martin, "Antiapoptotic Bcl-2 Family Protein Expression Increases with Progression of Oligodendroglioma", Cancer, vol. 86, pp. 1832-1839, 1999.
Eerola, A-K, "Accelerated Apoptosis and Low Bcl-2 Expression Associated with Neuroendocrine Differentiation Predict Shortened Survival in Operated Large Cell Carcinoma of the Lung", Pathology Oncology Research, vol. 5, pp. 179-186, 1999.
Fong, P., "Mcl-1 Expression in Gestational Trophoblastic Disease Correlates with Clinical Outcome", Cancer, vol. 103, pp. 268-276, 2005.
Gomez-Bougie, P., "The imbalance between Bim and Mcl-1 expression controls the survival of human myeloma cells", Eur. J. Immunol., vol. 34, pp. 3156-3164, 2004.
Greene, T.H. and P.G.M. Wuts, "Protective Groups in Organic Synthesis", 3rd E., John Wiley & Sons, New York, pp. 246-292, 1999.
Holzelova, E., "Autoimmune Lymphoproliferative Syndrome with Somatic Fas Mutations", New England Journal of Medicine, vol. 351, pp. 1409-1418, 2004.
Hotz, M., "Spontaneous Apoptosis and the Expression of p53 and Bcl-2 Family Proteins in Locally Advanced Head and Neck Cancer", Archives of Otolaryngology-Head and Neck Surgery, vol. 125, pp. 417-422, 1999.
IUPAC Commission on Nomenclature of Organic Chemistry, Pure Appl. Chem., vol. 45, pp. 10-13, 1976.
Kaufmann, S.H., "Elevated Expression of the Apoptotic Regulator Mcl-1 at the Time of Leukemic Relapse", Blood, vol. 91, pp. 991-1000, 1998.
Kuramoto, K., "High expression of MCL1 gene related to vascular endothelial growth factor is associated with poor outcome in non-Hodgkin's lymphoma", British J. of Haematology, vol. 116, pp. 158-161, 2002.
Maeta, Y., "Expression of Mcl-1 and p53 proteins predicts the survival of patients with T3 gastric carcinoma", Gastric Cancer, vol. 7, pp. 78-84, 2004.
Moshynska, O., "Prognostic Significance of a Short Sequence Insertion in the McL-1 Promoter in Chronic Lymphocytic Leukemia", J. of the National Cancer Institute, vol. 96, pp. 673 to 682, 2004.

(Continued)

*Primary Examiner* — Yong Chu
*Assistant Examiner* — Valerie Rodriguez-Garcia
(74) *Attorney, Agent, or Firm* — Jones Day

(57) ABSTRACT

Compounds of Formula I

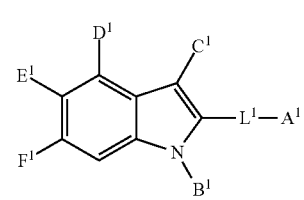

wherein $A^1$, $B^1$, $C^1$, $D^1$, $E^1$, $F^1$ and $L^1$ are as defined herein, which inhibit the activity of anti-apoptotic Mcl-1 protein, compositions containing the compounds, and methods of treating diseases involving overexpressed or unregulated Mcl-1 protein, such as leukemia and lymphoma, are disclosed.

7 Claims, No Drawings

OTHER PUBLICATIONS

Packham, G., "Bodyguards and assassins: Bcl-2 family proteins and apoptosis control in chronic cymphocytic leukaemia", Immunology, vol. 114, pp. 441-449, 2005.

Puck, J., "Immune disorders caused by Defects in the Caspase Cascade", Current Allergy and Asthma Reports, vol. 3, pp. 378-384, 2003.

Rassidakis, G., "BCL-2 family proteins in peripheral T-cell lymphomas: correlation with tumour apoptosis and proliferation", Journal of Pathology, vol. 200, pp. 240-248, 2003.

Shi, X, "Acquired Resistance of Pancreatic Cancer Cells towards 5-Fluorouracil and gemcitabine is Associated with Altered Expression of Apoptosis-Regulating Genes", Oncology, vol. 62, pp. 354-362, 2002.

Shimazaki, K., "Evaluation of apoptosis as a prognostic factor in myelodysplastic syndromes", Br. J. Haematol. , vol. 110(3), pp. 584-591, 2000.

Soini, Y., "Apoptosis and Expression of Apoptosis Regulating Proteins bcl-2, mcl-1, bcl-X, and bax in Malignant Mesothelioma", Clinical Cancer Research, vol. 5, pp. 3508-3515, 1999.

Strik, H , "BCL-2 Family protein expression in initial and recurrent gliobastomas: modulation by radiochemotherapy", J. Neurol. Neurosurg. Psychiatry, vol. 67, pp. 763-768, 1999.

Tsuji, J., "Palladium Reagents and Catalysts: New Perspectives for the 21st Century", John Wiley & Sons, Ltd. Chichester, pp. 1-670, 2004.

8798WO01 PCT Search Report and Written Opinion (PCT/US2008/060427) mailed Nov. 20, 2009.

\* cited by examiner

1-OXYALKYL-2-CARBOXYL-7-NONSUBSTITUTED INDOLE DERIVATIVES

CROSS-REFERENCE SECTION TO RELATED APPLICATIONS

This application claims the benefit of U.S. Provisional Patent Application No. 60/949,683, filed Jul. 13, 2007, and U.S. Provisional Patent Application No. 60/912,049, filed Apr. 16, 2007, which is hereby incorporated by reference.

FIELD OF THE INVENTION

This invention pertains to compounds which inhibit the activity of anti-apoptotic Mcl-1 protein, compositions containing the compounds, and methods of treating diseases involving overexpressed or unregulated Mcl-1 protein.

BACKGROUND OF THE INVENTION

Mcl-1 protein is associated with a number of diseases. There is therefore an existing need in the therapeutic arts for compounds which bind to and inhibit the activity of Mcl-1 protein.

SUMMARY OF THE INVENTION

One embodiment of this invention, therefore, pertains to compounds which inhibit the activity of Mcl-1 protein, the compounds having Formula I,

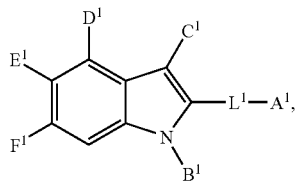

and therapeutically acceptable salts thereof, wherein $L^1$ is a bond or is alkylene, alkenylene or alkynylene;

$A^1$ is C(O)OH, or a bioisostere thereof, or is $C(O)OR^1$, $C(O)OR^1$, $C(O)OR^3$ or $C(O)OR^4$;

one, two, three, four or each of $B^1$, $C^1$, $D^1$, $E^1$ and $F^1$ are independently $R^1$, $R^2$, $R^3$ or $R^4$, $OR^1$, $SR^1$, $S(O)R^1$, $SO_2R^L$, $NH_2$, $NHR^1$, $N(R^1)_2$, $C(O)R^1$, $C(O)NH_2$, $C(O)NHR^1$, $C(O)N(R^1)_2$, $NHC(O)R^1$, $NR^1C(O)R^1$, $NHSO_2R^1$, $NR^1SO_2R^1$, $NHC(O)OR^1$, $NR^1C(O)OR^1$, $SO_2NH_2$, $SO_2NHR^1$, $SO_2N(R^1)_2$, $NHC(O)NH_2$, $NHC(O)R^1NHC(O)N(R^1)_2$, $NR^1C(O)N(R^1)_2$, $OR^2$, $SR^2$, $S(O)R^2$, $SO_2R^2$, $NH_2$, $NHR^2$, $N(R^2)_2$, $C(O)R^2$, $C(O)NH_2$, $C(O)NHR^2$, $C(O)N(R^2)_2$, $NHC(O)R^2$, $NR^2C(O)R^2$, $NHSO_2R^2$, $NR^2SO_2R^2$, $NHC(O)OR^2$, $NR^2C(O)OR^2$, $SO_2NH_2$, $SO_2NHR^2$, $SO_2N(R^2)_2$, $NHC(O)NH_2$, $NHC(O)R^2NHC(O)N(R^2)_2$, $NR^1C(O)N(R^2)_2$, $OR^3$, $SR^3$, $S(O)R^3$, $SO_2R^3$, $NH_2$, $NHR^3$, $N(R^3)_2$, $C(O)R^3$, $C(O)NH_2$, $C(O)NHR^3$, $C(O)N(R^3)_2$, $NHC(O)R^3$, $NR^2C(O)R^3$, $NHSO_2R^3$, $NR^3SO_2R^3$, $NHC(O)OR^3$, $NR^3C(O)OR^3$, $SO_2NH_2$, $SO_2NHR^3$, $SO_2N(R^3)_2$, $NHC(O)NH_2$, $NHC(O)R^3NHC(O)N(R^3)_2$, $NR^1C(O)N(R^3)_2$, $OR^4$, $SR^4$, $S(O)R^4$, $SO_2R^4$, $NH_2$, $NHR^4$, $N(R^4)_2$, $C(O)R^4$, $C(O)NH_2$, $C(O)NHR^4$, $C(O)N(R^4)_2$, $NHC(O)R^4$, $NR^4C(O)R^4$, $NHSO_2R^4$, $NR^4SO_2R^4$, $NHC(O)OR^4$, $NR^4C(O)OR^4$, $SO_2NH_2$, $SO_2NHR^4$, $SO_2N(R^4)_2$, $NHC(O)NH_2$, $NHC(O)R^4$, $NHC(O)N(R^4)_2$ or $NR^1C(O)N(R^4)_2$, and the remainder are H, OH, CN, F, Cl, Br or I;

$R^1$ is phenyl which is unfused or fused with benzene, heteroarene or $R^{1A}$; $R^{1A}$ is cycloalkane, cycloalkene, heterocycloalkane or heterocycloalkene;

$R^2$ is heteroaryl which is unfused or fused with benzene, heteroarene or $R^{2A}$; $R^{2A}$ is cycloalkane, cycloalkene, heterocycloalkane or heterocycloalkene;

$R^3$ is cycloalkyl, cycloalkenyl, heterocycloalkyl or heterocycloalkenyl, each of which is unfused or fused with benzene, heteroarene or $R^{3A}$; $R^{3A}$ is cycloalkane, cycloalkene, heterocycloalkane or heterocycloalkene;

$R^4$ is alkyl, alkenyl or alkynyl, each of which is unsubstituted or substituted with one, two, three, four or five of independently selected $R^5$, $OR^5$, $SR^5$, $S(O)R^5$, $SO_2R^5$, $NH_2$, $NHR^5$, $N(R^5)_2$, $C(O)R^5$, $C(O)NH_2$, $C(O)NHR^5$, $C(O)N(R^5)_2$, $NHC(O)R^5$, $NR^5C(O)R^5$, $NHSO_2R^5$, $NR^5SO_2R^5$, $NHC(O)OR^5$, $NR^5C(O)OR^5$, $SO_2NH_2$, $SO_2NHR^5$, $SO_2N(R^5)_2$, $NHC(O)NH_2$, $NHC(O)R^5$, $NHC(O)N(R^5)_2$, $NR^5C(O)N(R^5)_2$, OH, (O), C(O)OH, CN, $CF_3$, $OCF_3$, $CF_2CF_3$, F, Cl, Br or I;

$R^5$ is $R^6$, $R^7$, $R^8$ or $R^9$, $R^6$ is phenyl which is unfused or fused with benzene, heteroarene or $R^{6A}$; $R^{6A}$ is cycloalkane, cycloalkene, heterocycloalkane or heterocycloalkene;

$R^7$ is heteroaryl which is unfused or fused with benzene, heteroarene or $R^{7A}$; $R^{7A}$ is cycloalkane, cycloalkene, heterocycloalkane or heterocycloalkene;

$R^8$ is cycloalkyl, cycloalkenyl, heterocycloalkyl or heterocycloalkenyl, each of which is unfused or fused with benzene, heteroarene or $R^{8A}$; $R^{8A}$ is cycloalkane, cycloalkene, heterocycloalkane or heterocycloalkene;

$R^9$ is alkyl, alkenyl or alkynyl, each of which is unsubstituted or substituted with one, two, three, four or five of independently selected $R^{9A}$, $OR^{9A}$, $SR^{9A}$, $S(O)R^{9A}$, $SO_2R^{9A}$, $NH_2$, $NHR^{9A}$, $N(R^{9A})_2$, $C(O)R^{9A}$, $C(O)NH_2$, $C(O)NHR^{9A}$, $C(O)N(R^{9A})_2$, $NHC(O)R^{9A}$, $NR^{9A}C(O)R^{9A}$, $NHSO_2R^{9A}$, $NR^{9A}SO_2R^{9A}$, $NHC(O)OR^{9A}$, $NR^{9A}C(O)OR^{9A}$, $SO_2NH_2$, $SO_2NHR^{9A}$, $SO_2N(R^{9A})_2$, $NHC(O)NH_2$, $NHC(O)R^{9A}$ NHC(O)N(R^{9A})_2$, $NR^{9A}C(O)N(R^{9A})_2$, OH, (O), C(O)OH, CN, $CF_3$, $OCF_3$, $CF_2CF_3$, F, Cl, Br or I;

$R^{9A}$ is $R^{9B}$, $R^{9C}$ or $R^{9D}$;

$R^{9B}$ is phenyl which is unfused or fused with benzene, heteroarene or $R^{9B2}$; $R^{9B2}$ is cycloalkane, cycloalkene, heterocycloalkane or heterocycloalkene;

$R^{9C}$ is heteroaryl which is unfused or fused with benzene, heteroarene or $R^{9C2}$; $R^{9C2}$ is cycloalkane, cycloalkene, heterocycloalkane or heterocycloalkene;

$R^{9D}$ is cycloalkyl, cycloalkenyl, heterocycloalkyl or heterocycloalkenyl, each of which is unfused or fused with benzene, heteroarene or $R^{9D2}$; $R^{9D2}$ is cycloalkane, cycloalkene, heterocycloalkane or heterocycloalkene;

wherein each foregoing cyclic moiety is independently unsubstituted or substituted with one or two or three or four or five of independently selected $R^{10}$, $OR^{10}$, $OCH_2R^{10}$, $SR^{10}S(O)R^{10}$, $SO_2R^{10}$, $C(O)R^{10}$, $CO(O)R^{10}$, $OC(O)R^{10}$, $OC(O)OR^{10}$, $NO_2$, $NH_2$, $NHR^{10}$, $N(R^{10})_2$, $CH_2R^{10}$, $C(O)NH_2$, $C(O)NHR^{10}$, $C(O)N(R^{10})_2$, $NHC(O)R^{10}$, $NR^{10}C(O)R^{10}$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $CF_3$, $CF_2CF_3$, C(O)H, C(O)OH, $C(N)NH_2$, $C(N)NHR^{10}$, $C(N)N(R^{10})_2$, =NO-(alkylene)-C(O)CF_3$, CNOH, CNOCH_3$, OH, (O), $N_3$, $CF_3$, $CF_2CF_3$, $OCF_3$, $OCF_2CF_3$, F, Cl, Br or I;

$R^{10}$ is $R^{11}$, $R^{12}$, $R^{13}$ or $R^{14}$;

$R^{11}$ is phenyl which is unfused or fused with benzene, heteroarene or $R^{11A}$; $R^{11A}$ is cycloalkane, cycloalkene, heterocycloalkane or heterocycloalkene;

$R^{12}$ is heteroaryl which is unfused or fused with benzene, heteroarene or $R^{12A}$; $R^{12A}$ is cycloalkane, cycloalkene, heterocycloalkane or heterocycloalkene;

$R^{13}$ is cycloalkyl, cycloalkenyl, heterocycloalkyl or heterocycloalkenyl, each of which is unfused or fused with benzene, heteroarene or $R^{13A}$; $R^{13A}$ is cycloalkane, cycloalkene, heterocycloalkane or heterocycloalkene;

$R^{14}$ is alkyl, alkenyl or alkynyl, each of which is unsubstituted or substituted with one, two, three, four or five of independently selected $R^{15}$, $OR^{15}$, $SR^{15}$, $S(O)R^{15}$, $SO_2R^{15}$, $NH_2$, $NHR^{15}$, $N(R^{15})_2$, $C(O)R^{15}$, $C(O)NH_2$, $C(O)NHR^{15}$, $C(O)N(R^{15})_2$, $NHC(O)R^{15}$, $NR^{15}C(O)R^{15}$, $NHSO_2R^{15}$, $NR^{15}SO_2R^{15}$, $NHC(O)OR^{15}$, $NR^{15}C(O)OR^{15}$, $SO_2NH_2$, $SO_2NHR^{15}$, $SO_2N(R^{15})_2$, $NHC(O)NH_2$, $NHC(O)R^{15}NHC(O)N(R^{15})_2$, $NR^{15}C(O)N(R^{15})_2$, OH, (O), C(O)OH, CN, $CF_3$, $OCF_3$, $CF_2CF_3$, F, Cl, Br or I;

$R^{15}$ is $R^{16}$, $R^{17}$, $R^{18}$ or $R^{19}$;

$R^{16}$ is phenyl which is unfused or fused with benzene, heteroarene or $R^{15A}$; $R^{15A}$ is cycloalkane, cycloalkene, heterocycloalkane or heterocycloalkene;

$R^{17}$ is heteroaryl which is unfused or fused with benzene, heteroarene or $R^{16A}$; $R^{16A}$ is cycloalkane, cycloalkene, heterocycloalkane or heterocycloalkene;

$R^{18}$ is cycloalkyl, cycloalkenyl, heterocycloalkyl or heterocycloalkenyl, each of which is unfused or fused with benzene, heteroarene or $R^{18A}$; $R^{18A}$ is cycloalkane, cycloalkene, heterocycloalkane or heterocycloalkene;

$R^{19}$ is alkyl, alkenyl or alkynyl, each of which is unsubstituted or substituted with $R^{20}$;

$R^{20}$ is phenyl, heteroaryl, cycloalkyl, cycloalkenyl or heterocycloalkyl;

wherein $R^{11}$, $R^{12}$, $R^{13}$, $R^{16}$, $R^{17}$, and $R^{18}$ are independently unsubstituted or substituted with one or two or three or four or five of independently $R^{21}$, $OR^{21}$, $OCH_2R^{21}$, $SR^{21}$, $S(O)SO_2R^{21}$, $C(O)R^{21}$, $CO(O)R^{21}$, $C(O)R^{21}$, $C(O)OR^{21}$, $NO_2$, $NH_2$, $NHR^{21}$, $N(R^{21})_2$, $CH_2R^{21}$, $C(O)NH_2$, $C(O)NHR^{21}$, $C(O)N(R^{21})_2$, $NHC(O)R^{21}$, $NR^{21}C(O)R^{21}$, $C(O)NHOH$, $C(O)NHOR^{21}$, $C(O)NHSO_2R^{21}$, $C(O)NR^{21}SO_2R^{21}$, $SO_2NH_2$, $SO_2NHR^{21}$, $SO_2N(R^{21})_2$, $CF_3$, $CF_2CF_3$, $C(O)H$, C(O)OH, $C(N)NH_2$, $C(N)NHR^{21}$, $C(N)N(R^{21})_2$, =NO-(alkylene)-$C(O)CF_3$, CNOH, $CNOCH_3$, OH, (O), $N_3$, $CF_3$, $CF_2CF_3$, $OCF_3$, $OCF_2CF_3$, F, Cl, Br or I; and $R^{21}$ is alkyl, alkenyl, alkynyl, phenyl, heteroaryl, cycloalkyl, cycloalkenyl or heterocycloalkyl.

Still another embodiment pertains to compounds having Formula I,

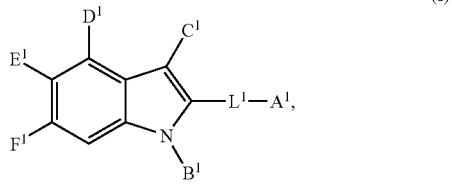

(I)

and therapeutically acceptable salts thereof, wherein $L^1$ is a bond or is alkylene, alkenylene or alkynylene;

$A^1$ is C(O)OH, or a bioisostere thereof, or is $C(O)OR^1$, $C(O)OR^2$, $C(O)OR^3$ or $C(O)OR^4$;

one, two, three, four or each of $B^1$, $C^1$, $D^1$, $E^1$ and $F^1$ are independently $R^1$, $R^2$, $R^3$ or $R^4$, $OR^1$, $SR^1$, $S(O)R^1$, $SO_2R^1$, $NH_2$, $NHR^1$, $N(R^1)_2$, $C(O)R^1$, $C(O)NH_2$, $C(O)NHR^1$, $C(O)N(R^1)_2$, $NHC(O)R^1$, $NR^1C(O)R^1$, $NHSO_2R^1$, $NR^1SO_2R^1$, $NHC(O)OR^1$, $NR^1C(O)OR^1$, $SO_2NH_2$, $SO_2NHR^1$, $SO_2N(R^1)_2$, $NHC(O)NH_2$, $NHC(O)R^1NHC(O)N(R^1)_2$, $NR^1C(O)N(R^1)_2$, $OR^2$, $SR^2$, $S(O)R^2$, $SO_2R^2$, $NH_2$, $NHR^2$, $N(R^2)_2$, $C(O)R^2$, $C(O)NH_2$, $C(O)NHR^2$, $C(O)N(R^2)_2$, $NHC(O)R^2$, $NR^2C(O)R^2$, $NHSO_2R^2$, $NR^2SO_2R^2$, $NHC(O)OR^2$, $NR^2C(O)OR^2$, $SO_2NH_2$, $SO_2NHR^2$, $SO_2N(R^2)_2$, $NHC(O)NH_2$, $NHC(O)R^2NHC(O)N(R^2)_2$, $NR^1C(O)N(R^2)_2$, $OR^3$, $SR^3$, $S(O)R^3$, $SO_2R^3$, $NH_2$, $NHR^3$, $N(R^3)_2$, $C(O)R^3$, $C(O)NH_2$, $C(O)NHR^3$, $C(O)N(R^3)_2$, $NHC(O)R^3$, $NR^2C(O)R^3$, $NHSO_2R^3$, $NR^3SO_2R^3$, $NHC(O)OR^3$, $NR^3C(O)OR^3$, $SO_2NH_2$, $SO_2NHR^3$, $SO_2N(R^3)_2$, $NHC(O)NH_2$, $NHC(O)R^3NHC(O)N(R^3)_2$, $NR^1C(O)N(R^3)_2$, $OR^4$, $SR^4$, $S(O)R^4$, $SO_2R^4$, $NH_2$, $NHR^4$, $N(R^4)_2$, $C(O)R^4$, $C(O)NH_2$, $C(O)NHR^4$, $C(O)N(R^4)_2$, $NHC(O)R^4$, $NR^4C(O)R^4$, $NHSO_2R^4$, $NR^4SO_2R^4$, $NHC(O)OR^4$, $NR^4C(O)OR^4$, $SO_2NH_2$, $SO_2NHR^4$, $SO_2N(R^4)_2$, $NHC(O)NH_2$, $NHC(O)R^4$, $NHC(O)N(R^4)_2$ or $NR^1C(O)N(R^4)_2$, and the remainder are H, OH, CN, F, Cl, Br or I;

$R^1$ is phenyl which is unfused or fused with benzene, heteroarene or $R^{1A}$; $R^{1A}$ is cycloalkane, cycloalkene, heterocycloalkane or heterocycloalkene;

$R^2$ is heteroaryl which is unfused or fused with benzene, heteroarene or $R^{2A}$; $R^{2A}$ is cycloalkane, cycloalkene, heterocycloalkane or heterocycloalkene;

$R^3$ is cycloalkyl, cycloalkenyl, heterocycloalkyl or heterocycloalkenyl, each of which is unfused or fused with benzene, heteroarene or $R^{3A}$; $R^{3A}$ is cycloalkane, cycloalkene, heterocycloalkane or heterocycloalkene;

$R^4$ is alkyl, alkenyl or alkynyl, each of which is unsubstituted or substituted with one, two, three, four or five of independently selected $R^5$, $OR^5$, $SR^5$, $S(O)R^5$, $SO_2R^5$, $NH_2$, $NHR^5$, $N(R^5)_2$, $C(O)R^5$, $C(O)NH_2$, $C(O)NHR^5$, $C(O)N(R^5)_2$, $NHC(O)R^5$, $NR^5C(O)R^5$, $NHSO_2R^5$, $NR^5SO_2R^5$, $NHC(O)OR^5$, $NR^5C(O)OR^5$, $SO_2NH_2$, $SO_2NHR^5$, $SO_2N(R^5)_2$, $NHC(O)NH_2$, $NHC(O)R^5$, $NHC(O)N(R^5)_2$, $NR^5C(O)N(R^5)_2$, OH, (O), C(O)OH, CN, $CF_3$, $OCF_3$, $CF_2CF_3$, F, Cl, Br or I;

$R^5$ is $R^6R^7R^8$ or $R^9$, $R^6$ is phenyl which is unfused or fused with benzene, heteroarene or $R^{6A}$; $R^{6A}$ is cycloalkane, cycloalkene, heterocycloalkane or heterocycloalkene;

$R^7$ is heteroaryl which is unfused or fused with benzene, heteroarene or $R^{7A}$; $R^{7A}$ is cycloalkane, cycloalkene, heterocycloalkane or heterocycloalkene;

$R^8$ is cycloalkyl, cycloalkenyl, heterocycloalkyl or heterocycloalkenyl, each of which is unfused or fused with benzene, heteroarene or $R^{8A}$; $R^{8A}$ is cycloalkane, cycloalkene, heterocycloalkane or heterocycloalkene;

$R^9$ is alkyl, alkenyl or alkynyl, each of which is unsubstituted or substituted with one, two, three, four or five of independently selected $R^{9A}$, $OR^{9A}$, $SR^{9A}$, $S(O)R^{9A}$, $SO_2R^{9A}$, $NH_2$, $NHR^{9A}$, $N(R^{9A})_2$, $C(O)R^{9A}$, $C(O)NH_2$, $C(O)NHR^{9A}$, $C(O)N(R^{9A})_2$, $NHC(O)R^{9A}$, $NR^{9A}C(O)R^{9A}$, $NHSO_2R^{9A}$, $NR^{9A}SO_2R^{9A}$, $NHC(O)OR^{9A}$, $NR^{9A}C(O)OR^{9A}$, $SO_2NH_2$, $SO_2NHR^{9A}$, $SO_2N(R^{9A})_2$, $NHC(O)NH_2$, $NHC(O)R^{9A}$ $NHC(O)N(R^{9A})_2$, $NR^{9A}C(O)N(R^{9A})_2$, OH, (O), C(O)OH, CN, $CF_3$, $OCF_3$, $CF_2CF_3$, F, Cl, Br or I;

$R^{9A}$ is $R^{9B}$, $R^{9C}$ or $R^{9D}$;

$R^{9B}$ is phenyl which is unfused or fused with benzene, heteroarene or $R^{9B2}$; $R^{9B2}$ is cycloalkane, cycloalkene, heterocycloalkane or heterocycloalkene;

$R^{9C}$ is heteroaryl which is unfused or fused with benzene, heteroarene or $R^{9C2}$; $R^{9C2}$ is cycloalkane, cycloalkene, heterocycloalkane or heterocycloalkene;

$R^{9D}$ is cycloalkyl, cycloalkenyl, heterocycloalkyl or heterocycloalkenyl, each of which is unfused or fused with benzene, heteroarene or $R^{9D2}$; $R^{9D2}$ is cycloalkane, cycloalkene, heterocycloalkane or heterocycloalkene;

wherein each foregoing cyclic moiety is independently unsubstituted or substituted with one or two or three or four or five of independently selected $R^{10}$, $OR^{10}$, $OCH_2R^{10}$, $SR^{10}S(O)R^{10}$, $SO_2R^{10}$, $C(O)R^{10}$, $CO(O)R^{10}$, $OC(O)R^{10}$, $OC(O)OR^{10}$, $NO_2$, $NH_2$, $NHR^{10}$, $N(R^{10})_2$, $CH_2R^{10}$, $C(O)NH_2$, $C(O)$ NHR$^{10}$, C(O)N(R$^{10}$)$_2$, NHC(O)R$^{10}$, NR$^{10}$C(O)R$^{10}$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, CF$_3$, CF$_2$CF$_3$, C(O)H, C(O)OH, C(N)NH$_2$, C(N)NHR$^{10}$, C(N)N(R$^{10}$)$_2$, =NO-(alkylene)-C(O)CF$_3$, CNOH, CNOCH$_3$, OH, (O), N$_3$, CF$_3$, CF$_2$CF$_3$, OCF$_3$, OCF$_2$CF$_3$, F, Cl, Br or I;

R$^{10}$ is R$^{11}$, R$^{12}$, R$^{13}$ or R$^{14}$;

R$^{11}$ is phenyl which is unfused or fused with benzene, heteroarene or R$^{11A}$; R$^{11A}$ is cycloalkane, cycloalkene, heterocycloalkane or heterocycloalkene;

R$^{12}$ is heteroaryl which is unfused or fused with benzene, heteroarene or R$^{12A}$; R$^{12A}$ is cycloalkane, cycloalkene, heterocycloalkane or heterocycloalkene;

R$^{13}$ is cycloalkyl, cycloalkenyl, heterocycloalkyl or heterocycloalkenyl, each of which is unfused or fused with benzene, heteroarene or R$^{13A}$; R$^{13A}$ is cycloalkane, cycloalkene, heterocycloalkane or heterocycloalkene;

R$^{14}$ is alkyl, alkenyl or alkynyl, each of which is unsubstituted or substituted with one, two, three, four or five of independently selected R$^{15}$, OR$^{15}$, SR$^{15}$, S(O)R$^{15}$, SO$_2$R$^{15}$, NH$_2$, NHR$^{15}$, N(R$^{15}$)$_2$, C(O)R$^{15}$, C(O)NH$_2$, C(O)NHR$^{15}$, C(O)N(R$^{15}$)$_2$, NHC(O)R$^{15}$, NR$^{15}$C(O)R$^{15}$, NHSO$_2$R$^{15}$, NR$^{15}$SO$_2$R$^{15}$, NHC(O)OR$^{15}$, NR$^{15}$C(O)OR$^{15}$, SO$_2$NH$_2$, SO$_2$NHR$^{15}$, SO$_2$N(R$^{15}$)$_2$, NHC(O)NH$_2$, NHC(O)R$^{15}$NHC(O)N(R$^{15}$)$_2$, NR$^{15}$C(O)N(R$^{15}$)$_2$, OH, (O), C(O)OH, CN, CF$_3$, OCF$_3$, CF$_2$CF$_3$, F, Cl, Br or I;

R$^{15}$ is R$^{16}$, R$^{17}$, R$^{18}$ or R$^{19}$;

R$^{16}$ is phenyl which is unfused or fused with benzene, heteroarene or R$^{15A}$; R$^{15A}$ is cycloalkane, cycloalkene, heterocycloalkane or heterocycloalkene;

R$^{17}$ is heteroaryl which is unfused or fused with benzene, heteroarene or R$^{16A}$; R$^{16A}$ is cycloalkane, cycloalkene, heterocycloalkane or heterocycloalkene;

R$^{18}$ is cycloalkyl, cycloalkenyl, heterocycloalkyl or heterocycloalkenyl, each of which is unfused or fused with benzene, heteroarene or R$^{18A}$; R$^{18A}$ is cycloalkane, cycloalkene, heterocycloalkane or heterocycloalkene;

R$^{19}$ is alkyl, alkenyl or alkynyl, each of which is unsubstituted or substituted with R$^{20}$;

R$^{20}$ is phenyl, heteroaryl, cycloalkyl, cycloalkenyl or heterocycloalkyl;

wherein R$^{11}$, R$^{12}$, R$^{13}$, R$^{16}$, R$^{17}$, and R$^{18}$ are independently unsubstituted or substituted with one or two or three or four or five of independently R$^{21}$, OR$^{21}$, OCH$_2$R$^{21}$, SR$^{21}$, S(O)R$^{21}$, SO$_2$R$^{21}$C(O)R$^{21}$CO(O)R$^{21}$, OC(O)R$^{21}$, OC(O)OR$^{21}$, NO$_2$, NH$_2$, NHR$^{21}$, N(R$^{21}$)$_2$, CH$_2$R$^{21}$, C(O)NH$_2$, C(O)NHR$^{21}$, C(O)N(R$^{21}$)$_2$, NHC(O)R$^{21}$, NR$^{21}$C(O)R$^{21}$, C(O)NHOH, C(O)NHOR$^{21}$, C(O)NHSO$_2$R$^{21}$, C(O)NR$^{21}$SO$_2$R$^{21}$, SO$_2$NH$_2$, SO$_2$NHR$^{21}$, SO$_2$N(R$^{21}$)$_2$, CF$_3$, CF$_2$CF$_3$, C(O)H, C(O)OH, C(N)NH$_2$, C(N)NHR$^{21}$, C(N)N(R$^{21}$)$_2$, =NO-(alkylene)-C(O)CF$_3$, CNOH, CNOCH$_3$, OH, (O), N$_3$, CF$_3$, CF$_2$CF$_3$, OCF$_3$, OCF$_2$CF$_3$, F, Cl, Br or I; and R$^{21}$ is alkyl, alkenyl, alkynyl, phenyl, heteroaryl, cycloalkyl, cycloalkenyl or heterocycloalkyl.

with or without administering one or more than one additional therapeutic agents and with or without also administering radiotherapy thereto.

Still another embodiment pertains to compounds having Formula I,

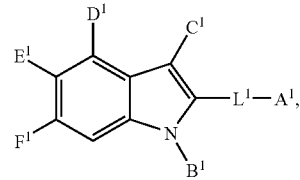

(I)

and therapeutically acceptable salts thereof, wherein

L$^1$ is a bond or is alkylene, alkenylene or alkynylene;

A$^1$ is C(O)OH, or a bioisostere thereof, or is C(O)OR$^1$, C(O)OR$^2$, C(O)OR$^3$ or C(O)OR$^4$;

one, two, three, four or each of B$^1$, C$^1$, D$^1$, E$^1$ and F$_1$ are independently R$^1$, R$^2$, R$^3$ or R$^4$, OR$^1$, SR$^1$, S(O)R$^1$, SO$_2$R$^1$, NH$_2$, NHR$^1$, N(R$^1$)$_2$, C(O)R$^1$, C(O)NH$_2$, C(O)NHR$^1$, C(O)N(R$^1$)$_2$, NHC(O)R$^1$, NR$^1$C(O)R$^1$, NHSO$_2$R$^1$, NR$^1$SO$_2$R$^1$, NHC(O)OR$^1$, NR$^1$C(O)OR$^1$, SO$_2$NH$_2$, SO$_2$NHR$^1$, SO$_2$N(R$^1$)$_2$, NHC(O)NH$_2$, NHC(O)R$^1$NHC(O)N(R$^1$)$_2$, NR$^1$C(O)N(R$^1$)$_2$, OR$^2$, SR$^2$, S(O)R$^2$, SO$_2$R$^2$, NH$_2$, NHR$^2$, N(R$^2$)$_2$, C(O)R$^2$, C(O)NH$_2$, C(O)NHR$^2$, C(O)N(R$^2$)$_2$, NHC(O)R$^2$, NR$^2$C(O)R$^2$, NHSO$_2$R$^2$, NR$^2$SO$_2$R$^2$, NHC(O)OR$^2$, NR$^2$C(O)OR$^2$, SO$_2$NH$_2$, SO$_2$NHR$^2$, SO$_2$N(R$^2$)$_2$, NHC(O)NH$_2$, NHC(O)R$^2$NHC(O)N(R$^2$)$_2$, NR$^1$C(O)N(R$^2$)$_2$, OR$^3$, SR$^3$, S(O)R$^3$, SO$_2$R$^3$, NH$_2$, NHR$^3$, N(R$^3$)$_2$, C(O)R$^3$, C(O)NH$_2$, C(O)NHR$^3$, C(O)N(R$^3$)$_2$, NHC(O)R$^3$, NR$^2$C(O)R$^3$, NHSO$_2$R$^3$, NR$^3$SO$_2$R$^3$, NHC(O)OR$^3$, NR$^3$C(O)OR$^3$, SO$_2$NH$_2$, SO$_2$NHR$^3$, SO$_2$N(R$^3$)$_2$, NHC(O)NH$_2$, NHC(O)R$^3$NHC(O)N(R$^3$)$_2$, NR$^1$C(O)N(R$^3$)$_2$, OR$^4$, SR$^4$, S(O)R$^4$, SO$_2$R$^4$, NH$_2$, NHR$^4$, N(R$^4$)$_2$, C(O)R$^4$, C(O)NH$_2$, C(O)NHR$^4$, C(O)N(R$^4$)$_2$, NHC(O)R$^4$, NR$^4$C(O)R$^4$, NHSO$_2$R$^4$, NR$^4$SO$_2$R$^4$, NHC(O)OR$^4$, NR$^4$C(O)OR$^4$, SO$_2$NH$_2$, SO$_2$NHR$^4$, SO$_2$N(R$^4$)$_2$, NHC(O)NH$_2$, NHC(O)R$^4$, NHC(O)N(R$^4$)$_2$ or NR$^1$C(O)N(R$^4$)$_2$, and the remainder are H, OH, CN, F, Cl, Br or I;

R$^1$ is phenyl which is unfused or fused with benzene, heteroarene or R$^{1A}$; R$^{1A}$ is cycloalkane, cycloalkene, heterocycloalkane or heterocycloalkene;

R$^2$ is heteroaryl which is unfused or fused with benzene, heteroarene or R$^{2A}$; R$^{2A}$ is cycloalkane, cycloalkene, heterocycloalkane or heterocycloalkene;

R$^3$ is cycloalkyl, cycloalkenyl, heterocycloalkyl or heterocycloalkenyl, each of which is unfused or fused with benzene, heteroarene or R$^{3A}$; R$^{3A}$ is cycloalkane, cycloalkene, heterocycloalkane or heterocycloalkene;

R$^4$ is alkyl, alkenyl or alkynyl, each of which is unsubstituted or substituted with one, two, three, four or five of independently selected R$^5$, OR$^5$, SR$^5$, S(O)R$^5$, SO$_2$R$^5$, NH$_2$, NHR$^5$, N(R$^5$)$_2$, C(O)R$^5$, C(O)NH$_2$, C(O)NHR$^5$, C(O)N(R$^5$)$_2$, NHC(O)R$^5$, NR$^5$C(O)R$^5$, NHSO$_2$R$^5$, NR$^5$SO$_2$R$^5$, NHC(O)OR$^5$, NR$^5$C(O)OR$^5$, SO$_2$NH$_2$, SO$_2$NHR$^5$, SO$_2$N(R$^5$)$_2$, NHC(O)NH$_2$, NHC(O)R$^5$, NHC(O)N(R$^5$)$_2$, NR$^5$C(O)N(R$^5$)$_2$, OH, (O), C(O)OH, CN, CF$_3$, OCF$_3$, CF$_2$CF$_3$, F, Cl, Br or I;

R$^5$ is R$^6$, R$^7$, R$^8$ or R$^9$,

R$^6$ is phenyl which is unfused or fused with benzene, heteroarene or R$^{6A}$; R$^{6A}$ is cycloalkane, cycloalkene, heterocycloalkane or heterocycloalkene;

R$^7$ is heteroaryl which is unfused or fused with benzene, heteroarene or R$^{7A}$; R$^{7A}$ is cycloalkane, cycloalkene, heterocycloalkane or heterocycloalkene;

R$^8$ is cycloalkyl, cycloalkenyl, heterocycloalkyl or heterocycloalkenyl, each of which is unfused or fused with benzene, heteroarene or R$^{8A}$; R$^{8A}$ is cycloalkane, cycloalkene, heterocycloalkane or heterocycloalkene;

R$^9$ is alkyl, alkenyl or alkynyl, each of which is unsubstituted or substituted with one, two, three, four or five of independently selected $R^{9A}$, $OR^{9A}$, $SR^{9A}$, $S(O)R^{9A}$, $SO_2R^{9A}$, $NH_2$, $NHR^{9A}$, $N(R^{9A})_2$, $C(O)R^9$, $C(O)NH_2$, $C(O)NHR^9$, $C(O)N(R^{9A})_2$, $NHC(O)R^{9A}$, $NR^{9A}C(O)R^{9A}$, $NHSO_2R^{9A}$, $NR^{9A}SO_2R^{9A}$, $NHC(O)OR^{9A}$, $NR^{9A}C(O)OR^{9A}$, $SO_2NH_2$, $SO_2NHR^{9A}$, $SO_2N(R^{9A})_2$, $NHC(O)NH_2$, $NHC(O)R^{9A}NHC(O)N(R^{9A})_2$, $NR^{9A}C(O)N(R^{9A})_2$, OH, (O), C(O)OH, CN, $CF_3$, $OCF_3$, $CF_2CF_3$, F, Cl, Br or I;

$R^{9A}$ is $R^{9B}$, $R^{9C}$ or $R^{9D}$;

$R^{9B}$ is phenyl which is unfused or fused with benzene, heteroarene or $R^{9B2}$; $R^{9B2}$ is cycloalkane, cycloalkene, heterocycloalkane or heterocycloalkene;

$R^{9C}$ is heteroaryl which is unfused or fused with benzene, heteroarene or $R^{9C2}$; $R^{9C2}$ is cycloalkane, cycloalkene, heterocycloalkane or heterocycloalkene;

$R^{9D}$ is cycloalkyl, cycloalkenyl, heterocycloalkyl or heterocycloalkenyl, each of which is unfused or fused with benzene, heteroarene or $R^{9D2}$; $R^{9D2}$ is cycloalkane, cycloalkene, heterocycloalkane or heterocycloalkene;

wherein each foregoing cyclic moiety is independently unsubstituted or substituted with one or two or three independently selected $R^{10}$, $OR^{10}$, $C(O)R^{10}$, $NO_2$, $N(R^{10})_2$, $C(O)NHR^{10}$, $SO_2N(R^{10})_2$, C(O)OH, OH, (O), $CF_3$, $OCF_3$, F, Cl, Br or I;

$R^{10}$ is $R^{11}$, $R^{12}$, $R^{13}$ or $R^{14}$;

$R^{11}$ is phenyl which is unfused or fused with benzene, heteroarene or $R^{11A}$; $R^{11A}$ is cycloalkane, cycloalkene, heterocycloalkane or heterocycloalkene;

$R^{12}$ is heteroaryl which is unfused or fused with benzene, heteroarene or $R^{12A}$; $R^{12A}$ is cycloalkane, cycloalkene, heterocycloalkane or heterocycloalkene;

$R^{13}$ is cycloalkyl, cycloalkenyl, heterocycloalkyl or heterocycloalkenyl, each of which is unfused or fused with benzene, heteroarene or $R^{13A}$; $R^{13A}$ is cycloalkane, cycloalkene, heterocycloalkane or heterocycloalkene;

$R^{14}$ is alkyl, alkenyl or alkynyl, each of which is unsubstituted or substituted with one, two, three, four or five of independently selected $R^{15}$, $OR^{15}$, $SR^{15}$, $S(O)R^{15}$, $SO_2R^{15}$, $NH_2$, $NHR^{15}$, $N(R^{15})_2$, $C(O)R^{15}$, $C(O)NH_2$, $C(O)NHR^{15}$, $C(O)N(R^{15})_2$, $NHC(O)R^{15}$, $NR^{15}C(O)R^{15}$, $NHSO_2R^{15}$, $NR^{15}SO_2R^{15}$, $NHC(O)OR^{15}$, $NR^{15}C(O)OR^{15}$, $SO_2NH_2$, $SO_2NHR^{15}$, $SO_2N(R^{15})_2$, $NHC(O)NH_2$, $NHC(O)R^{15}NHC(O)N(R^{15})_2$, $NR^{15}C(O)N(R^{15})_2$, OH, (O), C(O)OH, CN, $CF_3$, $OCF_3$, $CF_2CF_3$, F, Cl, Br or I;

$R^{15}$ is $R^{16}$, $R^{17}$, $R^{18}$ or $R^{19}$;

$R^{16}$ is phenyl which is unfused or fused with benzene, heteroarene or $R^{15A}$; $R^{15A}$ is cycloalkane, cycloalkene, heterocycloalkane or heterocycloalkene;

$R^{17}$ is heteroaryl which is unfused or fused with benzene, heteroarene or $R^{16A}$; $R^{16A}$ is cycloalkane, cycloalkene, heterocycloalkane or heterocycloalkene;

$R^{18}$ is cycloalkyl, cycloalkenyl, heterocycloalkyl or heterocycloalkenyl, each of which is unfused or fused with benzene, heteroarene or $R^{18A}$; $R^{18A}$ is cycloalkane, cycloalkene, heterocycloalkane or heterocycloalkene;

$R^{19}$ is alkyl, alkenyl or alkynyl, each of which is unsubstituted or substituted with $R^{20}$;

$R^{20}$ is phenyl, heteroaryl, cycloalkyl, cycloalkenyl or heterocycloalkyl;

wherein $R^{11}$, $R^{12}$, $R^{13}$, $R^{16}$, $R^{17}$, and $R^{18}$ are independently unsubstituted or substituted with one or two or three or four or five of independently $OR^{21}$, $NO_2$, $CF_3$, F, Cl, Br or I; and $R^{21}$ is alkyl, alkenyl, alkynyl, phenyl, heteroaryl, cycloalkyl, cycloalkenyl or heterocycloalkyl.

Still another embodiment pertains to compounds having Formula I,

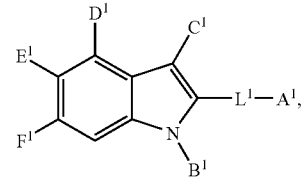

(I)

and therapeutically acceptable salts thereof, wherein $L^1$ is a bond or is alkylene, alkenylene or alkynylene;

$A^1$ is C(O)OH, or a bioisostere thereof, or is $C(O)OR^1$, $C(O)OR^2$, $C(O)OR^3$ or $C(O)OR^4$;

one, two, three, four or each of $B^1$, $C^1$, $D^1$, $E^1$ and $F^1$ are independently $R^1$, $R^2$, $R^3$ or $R^4$, $OR^1$, $SR^1$, $S(O)R^1$, $SO_2R^1$, $NH_2$, $NHR^1$, $N(R^1)_2$, $C(O)R^1$, $C(O)NH_2$, $SO_2NH_2$, $SO_2NHR^1$, $SO_2N(R^1)_2$, $OR^2$, $SR^2$, $S(O)R^2$, $SO_2R^2$, $NH_2$, $NHR^2$, $N(R^2)_2$, $C(O)R^2$, $C(O)NH_2$, $SO_2NH_2$, $SO_2NHR^2$, $SO_2N(R^2)_2$, $NHC(O)NH_2$, $OR^3$, $SR^3$, $S(O)R^3$, $SO_2R^3$, $NH_2$, $NHR^3$, $N(R^3)_2$, $C(O)R^3$, $C(O)NH_2$, $SO_2NH_2$, $SO_2NHR^3$, $SO_2N(R^3)_2$, $OR^4$, $SR^4$, $S(O)R^4$, $SO_2R^4$, $NH_2$, $NHR^4$, $N(R^4)_2$, $C(O)R^4$, $C(O)NH_2$, $SO_2NH_2$, $SO_2NHR^4$ or $SO_2N(R^4)_2$, and the remainder are H, OH, CN, F, Cl, Br or I;

$R^1$ is phenyl which is unfused or fused with benzene;

$R^2$ is heteroaryl;

$R^3$ is cycloalkyl, cycloalkenyl or heterocycloalkyl;

$R^4$ is alkyl, alkenyl or alkynyl, each of which is unsubstituted or substituted with one, two, three, four or five of independently selected $R^5$, $OR^5$, $SR^5$, $S(O)R^5$, $SO_2R^5$, $NH_2$, $NHR^5$, $N(R^5)_2$, $C(O)R^5$, $C(O)NH_2$, $C(O)NHR^5$, $C(O)N(R^5)_2$, $NHC(O)R^5$, $NR^5C(O)R^5$, $NHSO_2R^5$, $NR^5SO_2R^5$, $NHC(O)OR^5$, $NR^5C(O)OR^5$, $SO_2NH_2$, $SO_2NHR^5$, $SO_2N(R^5)_2$, $NHC(O)NH_2$, $NHC(O)R^5$, $NHC(O)N(R^5)_2$, $NR^5C(O)N(R^5)_2$, OH, (O), C(O)OH, CN, $CF_3$, $OCF_3$, $CF_2CF_3$, F, Cl, Br or I;

$R^5$ is $R^6$, $R^7$, $R^8$ or $R^9$, $R^6$ is phenyl which is unfused or fused with benzene, heteroarene or $R^{6A}$; $R^{6A}$ is cycloalkane;

$R^7$ is heteroaryl;

$R^8$ is cycloalkyl, cycloalkenyl, heterocycloalkyl or heterocycloalkenyl;

$R^9$ is alkyl, alkenyl or alkynyl, each of which is unsubstituted or substituted with one, two, three, four or five of independently selected $R^{9A}$, $OR^{9A}$, $SR^{9A}$, $S(O)R^{9A}$, $SO_2R^{9A}$, $NH_2$, $NHR^{9A}$, $N(R^{9A})_2$, $C(O)R^{9A}$, $C(O)NH_2$, $C(O)NHR^{9A}$, $C(O)N(R^{9A})_2$, $NHC(O)R^{9A}$, $NR^{9A}C(O)R^{9A}$, $NHSO_2R^{9A}$, $NR^{9A}SO_2R^{9A}$, $NHC(O)OR^{9A}$, $NR^{9A}C(O)OR^9$, $SO_2NH_2$, $SO_2NHR^{9A}$, $SO_2N(R^{9A})_2$, $NHC(O)NH_2$, $NHC(O)R^{9A}NHC(O)N(R^{9A})_2$, $NR^{9A}C(O)N(R^{9A})_2$, OH, (O), C(O)OH, CN, $CF_3$, $OCF_3$, $CF_2CF_3$, F, Cl, Br or I;

$R^{9A}$ is $R^{9B}$, $R^{9C}$ or $R^{9D}$;

$R^{9B}$ is phenyl;

$R^{9C}$ is heteroaryl;

$R^{9D}$ is cycloalkyl, cycloalkenyl, heterocycloalkyl or heterocycloalkenyl;

wherein each foregoing cyclic moiety is independently unsubstituted or substituted with one or two or three independently selected $R^{10}$, $OR^{10}$, $C(O)R^{10}$, $NO_2$, $N(R^{10})_2$, $C(O)NHR^{10}$, $SO_2N(R^{10})_2$, C(O)OH, OH, (O), $CF_3$, $OCF_3$, F, Cl, Br or I;

$R^{10}$ is $R^{11}$, $R^{12}$, $R^{13}$ or $R^{14}$;

$R^{11}$ is phenyl which is unfused or fused with benzene;

$R^{12}$ is heteroaryl;

$R^{13}$ is cycloalkyl, cycloalkenyl, heterocycloalkyl or heterocycloalkenyl;

$R^{14}$ is alkyl, alkenyl or alkynyl, each of which is unsubstituted or substituted with one, two, three, four or five of independently selected R$^{15}$, OR$^{15}$, SR$^{15}$, S(O)R$^{15}$, SO$_2$R$^{15}$NH$_2$, NHR$^{15}$, N(R$^{15}$)$_2$, C(O)R$^{15}$, C(O)NH$_2$, C(O)NHR$^{15}$, C(O)N (R$^{15}$)$_2$, NHC(O)R$^{15}$NR$^{15}$C(O)R$^{15}$, NHSO$_2$R$^{15}$, NR$^{15}$SO$_2$R$^{15}$, NHC(O)OR$^{15}$, NR$^{15}$C(O)OR$^{15}$, SO$_2$NH$_2$, SO$_2$NHR$^{15}$, SO$_2$N(R$^{15}$)$_2$, NHC(O)NH$_2$, NHC(O)R$^{15}$NHC (O)N(R$^{15}$)$_2$, NR$^{15}$C(O)N(R$^{15}$)$_2$, OH, (O), C(O)OH, CN, CF$_3$, OCF$_3$, CF$_2$CF$_3$, F, Cl, Br or I;

R$^{15}$ is R$^{16}$, R$^{17}$, R$^{18}$ or R$^{19}$;

R$^{16}$ is phenyl;

R$^{17}$ is heteroaryl;

R$^{18}$ is cycloalkyl, cycloalkenyl, heterocycloalkyl or heterocycloalkenyl;

R$^{19}$ is alkyl, alkenyl or alkynyl, each of which is unsubstituted or substituted with R$^{20}$;

R$^{20}$ is phenyl, heteroaryl, cycloalkyl, cycloalkenyl or heterocycloalkyl;

wherein R$^{11}$, R$^{12}$, R$^{13}$, R$^{16}$, R$^{17}$, and R$^{18}$ are independently unsubstituted or substituted with one or two or three or four or five of independently OR$^{21}$, NO$_2$, CF$_3$, F, Cl, Br or I; and R$^{21}$ is alkyl, alkenyl, alkynyl, phenyl, heteroaryl, cycloalkyl, cycloalkenyl or heterocycloalkyl.

Still another embodiment pertains to compounds having Formula I,

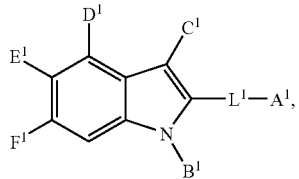

(I)

and therapeutically acceptable salts thereof, wherein

L$^1$ is a bond;

A$^1$ is C(O)OH;

one, two, three, four or each of B$^1$, C$^1$, D$^1$, E$^1$ and F$^1$ are independently R$^1$, R$^2$, R$^3$ or R$^4$, NHR$^1$OR$^4$, and the remainder are H, OH, CN, F, Cl, Br or I;

R$^1$ is phenyl which is unfused or fused with benzene;

R$^2$ is heteroaryl;

R$^3$ is cycloalkyl, cycloalkenyl or heterocycloalkyl;

R$^4$ is alkyl, alkenyl or alkynyl, each of which is unsubstituted or substituted with one, two, three, four or five of independently selected R$^5$, OR$^5$, SR$^5$, NH$_2$, NHR$^5$, N(R$^5$)$_2$, C(O) R$^5$, NHC(O)R$^5$, F, Cl, Br or I;

R$^5$ is R$^6$, R$^7$, R$^8$, R$^9$;

R$^6$ is phenyl which is unfused or fused with benzene, heteroarene or R$^{6A}$; R$^{6A}$ is cycloalkane;

R$^7$ is heteroaryl;

R$^8$ is cycloalkyl, cycloalkenyl, heterocycloalkyl or heterocycloalkenyl;

R$^9$ is alkyl, alkenyl or alkynyl, each of which is unsubstituted or substituted with one, two, three, four or five of independently selected R$^{9A}$, F, Cl, Br or I;

R$^{9A}$ is R$^{9B}$, R$^{9C}$ or R$^{9D}$;

R$^{9B}$ is phenyl;

R$^{9C}$ is heteroaryl;

R$^{9D}$ is cycloalkyl;

wherein each foregoing cyclic moiety is independently unsubstituted or substituted with one or two or three independently selected R$^{10}$, OR$^{10}$, C(O)R$^{10}$, NO$_2$, N(R$^{10}$)$_2$, C(O) NHR$^{10}$, SO$_2$N(R$^{10}$)$_2$, C(O)OH, OH, (O), CF$_3$, OCF$_3$, F, Cl, Br or I;

R$^{10}$ is R$^{11}$, R$^{13}$ or R$^{14}$;

R$^{11}$ is phenyl which is unfused or fused with benzene;

R$^{13}$ is heterocycloalkyl;

R$^{14}$ is alkyl or alkenyl, each of which is unsubstituted or substituted with one, two, three, four or five of independently selected R$^{15}$, OR$^{15}$, SO$_2$R$^{15}$, N(R$^{15}$)$_2$, F, Cl, Br or I;

R$^{15}$ is R$^{16}$, R$^{18}$ or R$^{19}$;

R$^{16}$ is phenyl;

R$^{18}$ is heterocycloalkyl;

R$^{19}$ is alkyl;

wherein R$^{11}$ and R$^{16}$ are independently unsubstituted or substituted with one or two or three or four or five of independently OR$^{21}$, NO$_2$, CF$_3$, F, Cl, Br or I; and R$^{21}$ is alkyl.

Still another embodiment pertains to 3-(3-cyclohexylpropyl)-1H-indole-2-carboxylic acid;

3-(4-cyclohexylbutyl)-1H-indole-2-carboxylic acid;

3-(3-(3-chlorophenoxy)propyl)-1H-indole-2-carboxylic acid;

3-(3-(3-(trifluoromethyl)phenoxy)propyl)-1H-indole-2-carboxylic acid;

3-(3-(1-naphthyloxy)propyl)-1H-indole-2-carboxylic acid;

3-(3-(2-benzylphenoxy)propyl)-1H-indole-2-carboxylic acid;

3-(3-(2,3-dihydro-1H-inden-5-yloxy)propyl)-1H-indole-2-carboxylic acid;

3-(3-((3-methyl-1-naphthyl)oxy)propyl)-1H-indole-2-carboxylic acid;

3-(3-((2-methyl-1-naphthyl)oxy)propyl)-1H-indole-2-carboxylic acid;

3-(3-(1-naphthylthio)propyl)-1H-indole-2-carboxylic acid;

5-bromo-3-(3-(1-naphthyloxy)propyl)-1H-indole-2-carboxylic acid;

3-(3-(1-naphthyloxy)propyl)-5-((1E)-3-phenylprop-1-enyl)-1H-indole-2-carboxylic acid;

5-((E)-2-cyclohexylvinyl)-3-(3-(1-naphthyloxy)propyl)-1H-indole-2-carboxylic acid;

3-(3-(1-naphthyloxy)propyl)-5-((E)-2-phenylvinyl)-1H-indole-2-carboxylic acid;

5-(4-fluorophenyl)-3-(3-(1-naphthyloxy)propyl)-1H-indole-2-carboxylic acid;

3-(3-(1-naphthyloxy)propyl)-5-(2-phenylethyl)-1H-indole-2-carboxylic acid;

3-(3-((7-methyl-2,3-dihydro-1H-inden-4-yl)oxy)propyl)-1H-indole-2-carboxylic acid;

3-(3-(5,6,7,8-tetrahydronaphthalen-1-yloxy)propyl)-1H-indole-2-carboxylic acid;

4-(4-fluorophenyl)-3-(3-(1-naphthyloxy)propyl)-1H-indole-2-carboxylic acid;

3-(3-(1-naphthyloxy)propyl)-6-((E)-2-phenylvinyl)-1H-indole-2-carboxylic acid;

3-(3-(1-naphthyloxy)propyl)-6-((1E)-3-phenylprop-1-enyl)-1H-indole-2-carboxylic acid;

3-(3-(1-naphthyloxy)propyl)-4-((1E)-3-phenylprop-1-enyl)-1H-indole-2-carboxylic acid;

6-(3-(benzyloxy)phenyl)-3-(3-(1-naphthyloxy)propyl)-1H-indole-2-carboxylic acid;

4-(3-(benzyloxy)phenyl)-3-(3-(1-naphthyloxy)propyl)-1H-indole-2-carboxylic acid;

5-bromo-3-(4-(1-naphthyloxy)butyl)-1H-indole-2-carboxylic acid;

1-methyl-3-(3-(1-naphthyloxy)propyl)-1H-indole-2-carboxylic acid;

3-(3-(1-naphthyloxy)propyl)-6-phenyl-1H-indole-2-carboxylic acid;

6-(2-methylphenyl)-3-(3-(1-naphthyloxy)propyl)-1H-indole-2-carboxylic acid;

6-(3-methylphenyl)-3-(3-(1-naphthyloxy)propyl)-1H-indole-2-carboxylic acid;

6-(4-methylphenyl)-3-(3-(1-naphthyloxy)propyl)-1H-indole-2-carboxylic acid;
3-(2-methylphenyl)-1-(3-(1-naphthyloxy)propyl)-1H-indole-2-carboxylic acid;
3-(1-naphthyl)-1-(3-(1-naphthyloxy)propyl)-1H-indole-2-carboxylic acid;
3-(3-(((3-(dimethylamino)propyl)amino)carbonyl)phenyl)-1-(3-(1-naphthyloxy)propyl)-1H-indole-2-carboxylic acid;
3-(1,1'-biphenyl-2-yl)-1-(3-(1-naphthyloxy)propyl)-1H-indole-2-carboxylic acid;
3-(2-methylphenyl)-1-(3-(2-naphthyloxy)propyl)-1H-indole-2-carboxylic acid;
3-(2-methylphenyl)-1-(3-(5,6,7,8-tetrahydronaphthalen-1-yloxy)propyl)-1H-indole-2-carboxylic acid;
3-(3-methylphenyl)-1-(3-(1-naphthyloxy)propyl)-1H-indole-2-carboxylic acid;
3-(3-chlorophenyl)-1-(3-(1-naphthyloxy)propyl)-1H-indole-2-carboxylic acid;
1-(3-(1-naphthyloxy)propyl)-3-phenyl-1H-indole-2-carboxylic acid;
1-(3-(1-naphthyloxy)propyl)-3-(2-(trifluoromethyl)phenyl)-1H-indole-2-carboxylic acid;
1-(3-(1-naphthyloxy)propyl)-3-(3-(trifluoromethyl)phenyl)-1H-indole-2-carboxylic acid;
1-(3-(1-naphthyloxy)propyl)-3-(4-(trifluoromethyl)phenyl)-1H-indole-2-carboxylic acid;
1-(3-(1-naphthyloxy)propyl)-3-(4-(trifluoromethoxy)phenyl)-1H-indole-2-carboxylic acid;
3-(2,3-dimethylphenyl)-1-(3-(1-naphthyloxy)propyl)-1H-indole-2-carboxylic acid;
3-(2,5-dimethylphenyl)-1-(3-(1-naphthyloxy)propyl)-1H-indole-2-carboxylic acid;
3-(3,4-dimethylphenyl)-1-(3-(1-naphthyloxy)propyl)-1H-indole-2-carboxylic acid;
3-(3,5-dimethylphenyl)-1-(3-(1-naphthyloxy)propyl)-1H-indole-2-carboxylic acid;
3-(2,5-dimethoxyphenyl)-1-(3-(1-naphthyloxy)propyl)-1H-indole-2-carboxylic acid;
3-(3,4-dimethoxyphenyl)-1-(3-(1-naphthyloxy)propyl)-1H-indole-2-carboxylic acid;
3-(2-methylphenyl)-1-(4-(1-naphthyloxy)butyl)-1H-indole-2-carboxylic acid;
3-(2-methylphenyl)-1-(4-(2-naphthyloxy)butyl)-1H-indole-2-carboxylic acid;
1-(4-(2,3-dichlorophenoxy)butyl)-3-(2-methylphenyl)-1H-indole-2-carboxylic acid;
1-(2-(2,4-dichlorophenoxy)ethyl)-3-(2-methylphenyl)-1H-indole-2-carboxylic acid;
1-(3-(2,4-dichlorophenoxy)propyl)-3-(2-methylphenyl)-1H-indole-2-carboxylic acid;
1-(4-(2,4-dichlorophenoxy)butyl)-3-(2-methylphenyl)-1H-indole-2-carboxylic acid;
3-benzyl-1-(3-(1-naphthyloxy)propyl)-1H-indole-2-carboxylic acid;
3-(2-methylbenzyl)-1-(3-(1-naphthyloxy)propyl)-1H-indole-2-carboxylic acid;
3-(3-methylbenzyl)-1-(3-(1-naphthyloxy)propyl)-1H-indole-2-carboxylic acid;
3-(4-methylbenzyl)-1-(3-(1-naphthyloxy)propyl)-1H-indole-2-carboxylic acid;
3-(2-naphthylmethyl)-1-(3-(1-naphthyloxy)propyl)-1H-indole-2-carboxylic acid;
1-(3-(1-naphthyloxy)propyl)-3-(2-phenylethyl)-1H-indole-2-carboxylic acid;
1-(3-(1-naphthyloxy)propyl)-3-(3-phenylpropyl)-1H-indole-2-carboxylic acid;
3-(2-methylphenyl)-1-(2-(1-naphthyloxy)ethyl)-1H-indole-2-carboxylic acid;
3-(2-methylphenyl)-1-(2-(2-naphthyloxy)ethyl)-1H-indole-2-carboxylic acid;
1-(2-(2,3-dichlorophenoxy)ethyl)-3-(2-methylphenyl)-1H-indole-2-carboxylic acid;
1-(3-(1-naphthyloxy)propyl)-3-((E)-2-phenylvinyl)-1H-indole-2-carboxylic acid;
1-(3-(1-naphthyloxy)propyl)-3-((1E)-3-phenylprop-1-enyl)-1H-indole-2-carboxylic acid;
3-((E)-2-cyclohexylvinyl)-1-(3-(1-naphthyloxy)propyl)-1H-indole-2-carboxylic acid;
1-(3-(1-naphthyloxy)propyl)-3-(3-(piperidin-1-ylcarbonyl)phenyl)-1H-indole-2-carboxylic acid;
3-(4-fluoro-3-(morpholin-4-ylcarbonyl)phenyl)-1-(3-(1-naphthyloxy)propyl)-1H-indole-2-carboxylic acid;
3-(3-(((2-methoxyethyl)amino)carbonyl)phenyl)-1-(3-(1-naphthyloxy)propyl)-1H-indole-2-carboxylic acid;
3-(3-((dimethylamino)sulfonyl)phenyl)-1-(3-(1-naphthyloxy)propyl)-1H-indole-2-carboxylic acid;
3-(3-(morpholin-4-ylmethyl)phenyl)-1-(3-(1-naphthyloxy)propyl)-1H-indole-2-carboxylic acid;
1-(3-(1-naphthyloxy)propyl)-3-piperidin-1-yl-1H-indole-2-carboxylic acid;
3-morpholin-4-yl-1-(3-(1-naphthyloxy)propyl)-1H-indole-2-carboxylic acid;
1-(3-(1-naphthyloxy)propyl)-3-((3-(trifluoromethoxy)phenyl)amino)-1H-indole-2-carboxylic acid;
3-(4-carboxypiperidin-1-yl)-1-(3-(1-naphthyloxy)propyl)-1H-indole-2-carboxylic acid;
3-anilino-4-(2-methylphenyl)-1-(3-(1-naphthyloxy)propyl)-1H-indole-2-carboxylic acid;
3-(3-(1-naphthylthio)cyclohexyl)-1H-indole-2-carboxylic acid;
3-(3-(1-naphthyloxy)cyclohexyl)-1H-indole-2-carboxylic acid;
1-(2-methylbenzyl)-3-(3-(1-naphthyloxy)propyl)-1H-indole-2-carboxylic acid;
1-(2-(dimethylamino)ethyl)-3-(3-(1-naphthyloxy)propyl)-1H-indole-2-carboxylic acid;
1-(3-methylbenzyl)-3-(3-(1-naphthyloxy)propyl)-1H-indole-2-carboxylic acid;
1-(4-methylbenzyl)-3-(3-(1-naphthyloxy)propyl)-1H-indole-2-carboxylic acid;
1-(1,1'-biphenyl-2-ylmethyl)-3-(3-(1-naphthyloxy)propyl)-1H-indole-2-carboxylic acid;
1-(1,1'-biphenyl-3-ylmethyl)-3-(3-(1-naphthyloxy)propyl)-1H-indole-2-carboxylic acid;
1-(1,1'-biphenyl-4-ylmethyl)-3-(3-(1-naphthyloxy)propyl)-1H-indole-2-carboxylic acid;
1-(2,4-dimethylbenzyl)-3-(3-(1-naphthyloxy)propyl)-1H-indole-2-carboxylic acid;
1-(4-carboxybenzyl)-3-(3-(1-naphthyloxy)propyl)-1H-indole-2-carboxylic acid;
1-((2S)-2-methyl-3-(1-naphthyloxy)propyl)-4-(2-methylphenyl)-1H-indole-2-carboxylic acid;
1-((2R)-2-methyl-3-(1-naphthyloxy)propyl)-4-(2-methylphenyl)-1H-indole-2-carboxylic acid;
3-(3-(1-naphthyloxy)propyl)-1-(pyridin-4-ylmethyl)-1H-indole-2-carboxylic acid;
3-(3-(1-naphthyloxy)propyl)-1-(pyridin-2-ylmethyl)-1H-indole-2-carboxylic acid;
1-(4-methoxybenzyl)-3-(2-(1-naphthyloxy)ethoxy)-1H-indole-2-carboxylic acid;
1-(4-methoxybenzyl)-3-(3-(1-naphthyloxy)prop-1-ynyl)-1H-indole-2-carboxylic acid;

4-(2-methylphenyl)-1-(3-(1-naphthyloxy)propyl)-1H-indole-2-carboxylic acid;
4-(2,6-dimethylphenyl)-1-(3-(1-naphthyloxy)propyl)-1H-indole-2-carboxylic acid;
1-(3-(1-naphthyloxy)propyl)-4-(1,3,5-trimethyl-1H-pyrazol-4-yl)-1H-indole-2-carboxylic acid;
1-(3-(1-naphthyloxy)propyl)-4-(2-oxocyclohexyl)-1H-indole-2-carboxylic acid;
4-(2-methylphenyl)-3-(morpholin-4-ylmethyl)-1-(3-(1-naphthyloxy)propyl)-1H-indole-2-carboxylic acid;
4-(2-methylphenyl)-1-(3-(1-naphthyloxy)propyl)-3-(pyrrolidin-1-ylmethyl)-1H-indole-2-carboxylic acid;
3-((dimethylamino)methyl)-4-(2-methylphenyl)-1-(3-(1-naphthyloxy)propyl)-1H-indole-2-carboxylic acid;
3-(((cyclohexylmethyl)amino)methyl)-4-(2-methylphenyl)-1-(3-(1-naphthyloxy)propyl)-1H-indole-2-carboxylic acid;
4-(2-morpholin-4-ylcyclohexyl)-1-(3-(1-naphthyloxy)propyl)-1H-indole-2-carboxylic acid;
4-(2-methylphenyl)-3-((4-methylpiperazin-1-yl)methyl)-1-(3-(1-naphthyloxy)propyl)-1H-indole-2-carboxylic acid;
4-(2-methylphenyl)-1-(3-(1-naphthyloxy)propyl)-3-(piperidin-1-ylmethyl)-1H-indole-2-carboxylic acid;
4-(2-methylphenyl)-3-((4-methylpiperidin-1-yl)methyl)-1-(3-(1-naphthyloxy)propyl)-1H-indole-2-carboxylic acid;
3-((benzyl(methyl)amino)methyl)-4-(2-methylphenyl)-1-(3-(1-naphthyloxy)propyl)-1H-indole-2-carboxylic acid;
4-(2-methylphenyl)-3-((methyl(pyridin-2-ylmethyl)amino)methyl)-1-(3-(1-naphthyloxy)propyl)-1H-indole-2-carboxylic acid;
4-(2-methylphenyl)-3-((methyl(pyridin-3-ylmethyl)amino)methyl)-1-(3-(1-naphthyloxy)propyl)-1H-indole-2-carboxylic acid;
4-(2-methylphenyl)-3-((methyl(pyridin-4-ylmethyl)amino)methyl)-1-(3-(1-naphthyloxy)propyl)-1H-indole-2-carboxylic acid;
4-(2-(4-fluorophenyl)cyclohex-1-en-1-yl)-1-(3-(1-naphthyloxy)propyl)-1H-indole-2-carboxylic acid;
4-(2-methyl-6-nitrophenyl)-1-(3-(1-naphthyloxy)propyl)-1H-indole-2-carboxylic acid;
4-(2-chloro-6-methylphenyl)-1-(3-(1-naphthyloxy)propyl)-1H-indole-2-carboxylic acid;
1-(3-(1-naphthyloxy)propyl)-4-(2-(4-nitrophenyl)cyclohex-1-en-1-yl)-1H-indole-2-carboxylic acid;
4-(2-(3-methoxyphenyl)cyclohex-1-en-1-yl)-1-(3-(1-naphthyloxy)propyl)-1H-indole-2-carboxylic acid;
4-(5-fluoro-2-methyl-3-((methylsulfonyl)methyl)phenyl)-1-(3-(1-naphthyloxy)propyl)-1H-indole-2-carboxylic acid;
4-(2-methylphenyl)-1-(3-(1-naphthyloxy)propyl)-3-phenyl-1H-indole-2-carboxylic acid;
3-bromo-4-(2-methylphenyl)-1-(3-(1-naphthyloxy)propyl)-1H-indole-2-carboxylic acid;
4-(2-methylphenyl)-3-((4-methylphenyl)amino)-1-(3-(1-naphthyloxy)propyl)-1H-indole-2-carboxylic acid;
3-(4-hydroxyphenyl)-4-(2-methylphenyl)-1-(3-(1-naphthyloxy)propyl)-1H-indole-2-carboxylic acid;
3-(3-hydroxyphenyl)-4-(2-methylphenyl)-1-(3-(1-naphthyloxy)propyl)-1H-indole-2-carboxylic acid;
4-(2-methylphenyl)-1-(3-(1-naphthyloxy)propyl)-3-pyridin-4-yl-1H-indole-2-carboxylic acid;
4-(2-methylphenyl)-1-(3-(1-naphthyloxy)propyl)-3-pyridin-3-yl-1H-indole-2-carboxylic acid;
3-cyano-4-(2-methylphenyl)-1-(3-(1-naphthyloxy)propyl)-1H-indole-2-carboxylic acid;
3-bromo-5-fluoro-1-(3-(1-naphthyloxy)propyl)-1H-indole-2-carboxylic acid;
5-(benzyloxy)-1-(3-(1-naphthyloxy)propyl)-3-(2-(trifluoromethyl)phenyl)-1H-indole-2-carboxylic acid;
5-fluoro-3-(2-methylphenyl)-1-(3-(1-naphthyloxy)propyl)-1H-indole-2-carboxylic acid;
5-fluoro-1-(3-(1-naphthyloxy)propyl)-1H-indole-2-carboxylic acid;
5-fluoro-1-(3-(1-naphthyloxy)propyl)-3-(2-(trifluoromethyl)phenyl)-1H-indole-2-carboxylic acid;
5-fluoro-3-(2-isopropylphenyl)-1-(3-(1-naphthyloxy)propyl)-1H-indole-2-carboxylic acid;
4-(2-methylphenyl)-1-(3-(1-naphthyloxy)propyl)-3-((3-(trifluoromethoxy)phenyl)amino)-1H-indole-2-carboxylic acid;
5-(benzyloxy)-1-(3-(1-naphthyloxy)propyl)-3-((3-(trifluoromethoxy)phenyl)amino)-1H-indole-2-carboxylic acid;
5-(benzyloxy)-1-(3-(1-naphthyloxy)propyl)-1H-indole-2-carboxylic acid;
5-(benzyloxy)-3-(2-isopropylphenyl)-1-(3-(1-naphthyloxy)propyl)-1H-indole-2-carboxylic acid;
3-(2-(tert-butoxymethyl)phenyl)-5-fluoro-1-(3-(1-naphthyloxy)propyl)-1H-indole-2-carboxylic acid;
5-fluoro-1-(3-(1-naphthyloxy)propyl)-3-(2-((3-(trifluoromethyl)phenoxy)methyl)phenyl)-1H-indole-2-carboxylic acid;
5-chloro-3-(2-isopropylphenyl)-1-(3-(1-naphthyloxy)propyl)-1H-indole-2-carboxylic acid;
5-chloro-3-(2-methylphenyl)-1-(3-(1-naphthyloxy)propyl)-1H-indole-2-carboxylic acid;
5-hydroxy-3-(2-isopropylphenyl)-1-(3-(5,6,7,8-tetrahydronaphthalen-1-yloxy)propyl)-1H-indole-2-carboxylic acid;
5-hydroxy-3-(2-isopropylphenyl)-1-(3-(1-naphthyloxy)propyl)-1H-indole-2-carboxylic acid;
3-(2-isopropylphenyl)-5-(4-morpholin-4-ylbutoxy)-1-(3-(1-naphthyloxy)propyl)-1H-indole-2-carboxylic acid;
5-fluoro-1-(3-(1-naphthyloxy)propyl)-3-(1,3,5-trimethyl-1H-pyrazol-4-yl)-1H-indole-2-carboxylic acid;
3-(2-isopropylphenyl)-1-(3-(1-naphthyloxy)propyl)-5-phenyl-1H-indole-2-carboxylic acid;
3-(2,6-dimethylphenyl)-5-fluoro-1-(3-(1-naphthyloxy)propyl)-1H-indole-2-carboxylic acid;
3-(2-isopropylphenyl)-1-(3-(1-naphthyloxy)propyl)-1H-indole-2-carboxylic acid;
1-(3-(1-naphthyloxy)propyl)-5-((1E)-pent-1-enyl)-1H-indole-2-carboxylic acid;
3-(2,6-dimethylphenyl)-1-(3-(1-naphthyloxy)propyl)-1H-indole-2-carboxylic acid;
1-(3-(1-naphthyloxy)propyl)-3-(1,3,5-trimethyl-1H-pyrazol-4-yl)-1H-indole-2-carboxylic acid;
3-(2-chlorophenyl)-5-fluoro-1-(3-(1-naphthyloxy)propyl)-1H-indole-2-carboxylic acid;
3-((1E)-5-(dimethylamino)pent-1-enyl)-5-fluoro-1-(3-(1-naphthyloxy)propyl)-1H-indole-2-carboxylic acid;
3-((1E)-6-((2-carboxybenzoyl)amino)hex-1-enyl)-5-fluoro-1-(3-(1-naphthyloxy)propyl)-1H-indole-2-carboxylic acid;
3-((1E)-6-aminohex-1-enyl)-5-fluoro-1-(3-(1-naphthyloxy)propyl)-1H-indole-2-carboxylic acid;
3-(6-aminohexyl)-5-fluoro-1-(3-(1-naphthyloxy)propyl)-1H-indole-2-carboxylic acid;
3-(5-(dimethylamino)pentyl)-5-fluoro-1-(3-(1-naphthyloxy)propyl)-1H-indole-2-carboxylic acid;
6-chloro-1-(3-(1-naphthyloxy)propyl)-1H-indole-2-carboxylic acid;
3-(2-((1E)-5-(dimethylamino)pent-1-enyl)phenyl)-5-fluoro-1-(3-(1-naphthyloxy)propyl)-1H-indole-2-carboxylic acid;

3-(2-(dimethylamino)phenyl)-5-fluoro-1-(3-(1-naphthyloxy)propyl)-1H-indole-2-carboxylic acid;
1-(3-(1-naphthyloxy)propyl)-1H-indole-2-carboxylic acid;
1-methyl-5-(4-(2-methylphenyl)-1-(3-(1-naphthyloxy)propyl)-1H-indol-2-yl)-1H-pyrazol-3-ol;
4-(2-methylphenyl)-1-(3-(1-naphthyloxy)propyl)-2-(1H-tetraazol-5-yl)-1H-indole;
and therapeutically acceptable salts, prodrugs, esters, amides, salts of prodrugs, salts of esters, and salts of amides thereof.

Still another embodiment pertains to compositions comprising an excipient and a therapeutically effective amount of a compound having Formula I.

Still another embodiment pertains to methods for treating mammals having a disease characterized by overexpression or unregulation of Mcl-1 protein comprising administering thereto a therapeutically effective amount of a compound having Formula I.

Still another embodiment comprises methods of treating mammals having a disease characterized by overexpression or unregulation of Mcl-1 protein comprising administering thereto therapeutically effective amounts of a compound having Formula I and one or more than one additional therapeutic agents, with or without also administering radiotherapy thereto.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all combinations herein, that monovalent moieties having more than one atom are attached through their left ends, and that divalent moieties are drawn from left to right.

It is also meant to be understood that a specific embodiment of a variable moiety may be the same or different as another specific embodiment having the same identifier.

The term "alkenyl," as used herein, means monovalent, straight or branched chain hydrocarbon moieties having one or more than one carbon-carbon double bonds, such as $C_2$-alkenyl, $C_3$-alkenyl, $C_4$-alkenyl, $C_5$-alkenyl, $C_6$-alkenyl and the like.

The term "alkenylene," as used herein, means divalent, straight or branched chain hydrocarbon moieties having one or more than one carbon-carbon double bonds, such as $C_2$-alkenylene, $C_3$-alkenylene, $C_4$-alkenylene, $C_5$-alkenylene, $C_6$-alkenylene and the like.

The term "alkyl," as used herein, means monovalent, saturated, straight or branched chain hydrocarbon moieties, such as $C_1$-alkyl, $C_2$-alkyl, $C_3$-alkyl, $C_4$-alkyl, $C_5$-alkyl, $C_6$-alkyl and the like.

The term "alkylene," as used herein, means divalent, saturated, straight or branched chain hydrocarbon moieties, such as $C_1$-alkylene, $C_2$-alkylene, $C_3$-alkylene, $C_4$-alkylene, $C_5$-alkylene, $C_6$-alkylene and the like.

The term "alkynyl," as used herein, means monovalent, straight or branched chain hydrocarbon moieties having one or more than one carbon-carbon triple bonds, such as $C_2$-alkynyl, $C_3$-alkynyl, $C_4$-alkynyl, $C_5$-alkynyl, $C_6$-alkynyl and the like.

The term "alkynylene," as used herein, means divalent, straight or branched chain hydrocarbon moieties having one or more than one carbon-carbon triple bonds, such as $C_2$-alkynylene, $C_3$-alkynylene, $C_4$-alkynylene, $C_5$-alkynylene, $C_6$-alkynylene and the like.

The term "C(O)OH bioisostere, as used herein, means a moiety with a substantially similar physical or chemical property that imparts similar biological properties to the compound having Formula (I). Examples of C(O)OH bioisosteres include monovalent radicals derived from removal of one hydrogen atom from a molecule such as isothiazol-3(2H)-one 1,1-dioxide, isothiazolidin-3-one 1,1-dioxide, 1,2,4-oxadiazol-5(2H)-one, 1,2,5-thiadiazolidin-3-one 1,1-dioxide, 1,2,5-thiadiazol-3-ol, 1,2,4-oxadiazolidine-3,5-dione, 2H-tetraazole and the like.

The term "cycloalkane," as used herein, means saturated cyclic or bicyclic hydrocarbon moieties, such as $C_4$-cycloalkane, $C_5$-cycloalkane, $C_6$-cycloalkane, $C_7$-cycloalkane, $C_8$-cycloalkane, $C_9$-cycloalkane, $C_{10}$-cycloalkane, $C_{11}$-cycloalkane, $C_{12}$-cycloalkane and the like.

The term "cycloalkyl," as used herein, means monovalent, saturated cyclic and bicyclic hydrocarbon moieties, such as $C_3$-cycloalkyl, $C_4$-cycloalkyl, $C_5$-cycloalkyl, $C_6$-cycloalkyl, $C_7$-cycloalkyl, $C_8$-cycloalkyl, $C_9$-cycloalkyl, $C_{10}$-cycloalkyl, $C_{11}$-cycloalkyl, $C_{12}$-cycloalkyl and the like.

The term "cycloalkene," as used herein, means cyclic and bicyclic hydrocarbon moieties having one or more than one carbon-carbon double bonds, such as $C_5$-cycloalkene, $C_6$-cycloalkene, $C_7$-cycloalkene, $C_8$-cycloalkene, $C_9$-cycloalkene, $C_{10}$-cycloalkene, $C_{11}$-cycloalkene, $C_{12}$-cycloalkene and the like.

The term "cycloalkenyl," as used herein, means monovalent, cyclic hydrocarbon moieties having one or more than one carbon-carbon double bonds, such as $C_4$-cycloalkenyl, $C_5$-cycloalkenyl, $C_6$-cycloalkenyl, $C_7$-cycloalkenyl, $C_8$-cycloalkenyl, $C_9$-cycloalkenyl, $C_{10}$-cycloalkenyl, $C_{11}$-cycloalkenyl, $C_{12}$-cycloalkenyl and the like.

The term "heteroarene," as used herein, means furan, imidazole, isothiazole, isoxazole, 1,2,3-oxadiazole, 1,2,5-oxadiazole, 1,3,4-oxadiazole, oxazole, pyrazine, pyrazole, pyridazine, pyridine, pyrimidine, pyrrole, thiazole, 1,3,4-thiadiazole, thiophene, triazine and 1,2,3-triazole.

The term "heteroaryl," as used herein, means furanyl, imidazolyl, isothiazolyl, isoxazolyl, 1,2,3-oxadiazoyl, 1,2,5-oxadiazolyl, 1,3,4-oxadiazolyl, oxazolyl, pyrazinyl, pyrazolyl, pyridazinyl, pyridinyl, pyrimidinyl, pyrrolyl, tetrazolyl, thiazolyl, 1,2,3-thiadiazoyl, 1,2,5-thiadiazolyl, 1,3,4-thiadiazolyl, thiophenyl, triazinyl and 1,2,3-triazolyl.

The term "heterocycloalkane," as used herein, means cycloalkane having one or two or three $CH_2$ moieties replaced with independently selected O, S, S(O), $SO_2$ or NH and one or two CH moieties unreplaced or replaced with N and also means cycloalkane having one or two or three $CH_2$ moieties unreplaced or replaced with independently selected O, S, S(O), $SO_2$ or NH and one or two CH moieties replaced with N.

The term "heterocycloalkene," as used herein, means cycloalkene having one or two or three $CH_2$ moieties replaced with independently selected O, S, S(O), $SO_2$ or NH and one or two CH moieties unreplaced or replaced with N and also means cycloalkene having one or two or three $CH_2$ moieties unreplaced or replaced with independently selected O, S, S(O), $SO_2$ or NH and one or two CH moieties replaced with N.

The term "heterocycloalkyl," as used herein, means cycloalkyl having one or two or three $CH_2$ moieties replaced with independently selected O, S, S(O), $SO_2$ or NH and one or two CH moieties unreplaced or replaced with N and also means cycloalkyl having one or two or three $CH_2$ moieties unreplaced or replaced with independently selected O, S, S(O), $SO_2$ or NH and one or two CH moieties replaced with N.

The term "heterocycloalkenyl," as used herein, means cycloalkenyl having one or two or three $CH_2$ moieties replaced with independently selected O, S, S(O), SO$_2$ or NH and one or two CH moieties unreplaced or replaced with N and also means cycloalkenyl having one or two or three CH$_2$ moieties unreplaced or replaced with independently selected O, S, S(O), SO$_2$ or NH and one or two CH moieties replaced with N.

The term "cyclic moiety," as used herein, means benzene, cycloalkane, cycloalkyl, cycloalkene, cycloalkenyl, heteroarene, heteroaryl, heterocycloalkane, heterocycloalkyl, heterocycloalkene, heterocycloalkenyl, phenyl and spiroalkyl.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures, relative and absolute diastereoisomers and the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention containing NH, C(O)H, C(O)OH, C(O)NH$_2$, OH or SH moieties may have attached thereto prodrug-forming moieties. The prodrug-forming moieties are removed by metabolic processes and release the compounds having the freed NH, C(O)H, C(O)OH, C(O)NH$_2$, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having Formula I, produced by in vitro or in vivo metabolic processes, may also have utility for treating diseases caused or exacerbated by overexpressed or unregulated Mcl-1 protein.

Certain precursor compounds of compounds having Formula I may be metabolized in vitro or in vivo to form compounds having Formula I and may thereby also have utility for treating diseases caused or exacerbated by overexpressed or unregulated Mcl-1 protein.

Compounds having Formula I may exist as acid addition salts, basic addition salts or zwitterions. Salts of compounds having Formula I are prepared during their isolation or following their purification. Acid addition salts are those derived from the reaction of a compound having Formula I with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having Formula I are meant to be embraced by this invention. Basic addition salts of compounds are those derived from the reaction of the compounds having Formula I with the bicarbonate, carbonate, hydroxide or phosphate of cations such as lithium, sodium, potassium, calcium and magnesium.

Compounds having Formula I may be administered, for example, bucally, ophthalmically, orally, osmotically, parenterally (intramuscularly, intraperintoneally intrasternally, intravenously, subcutaneously), rectally, topically, transdermally and vaginally.

Therapeutically effective amounts of a compound having Formula I depend on recipient of treatment, disease treated and severity thereof, composition comprising it, time of administration, route of administration, duration of treatment, potency, rate of clearance and whether or not another drug is co-administered. The amount of a compound having Formula I used to make a composition to be administered daily to a patient in a single dose or in divided doses is from about 0.001 to about 200 mg/kg body weight. Single dose compositions contain these amounts or a combination of submultiples thereof.

Compounds having Formula I may be administered with or without an excipient. Excipients include, for example, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Compounds having Formula I may be radiolabeled with a radioactive isotope such as carbon (i.e. $^{13}$C), hydrogen (i.e. $^{3}$H), nitrogen (i.e. $^{15}$N), phosphorus (i.e. $^{32}$P), sulfur (i.e. $^{35}$S), iodide (i.e. $^{125}$I) and the like. Radioactive isotopes may be incorporated into the compounds having Formula I by reacting the same and a radioactive derivitizing agent or by incorporating a radiolabeled intermediate into their syntheses. The radiolabeled compounds of Formula I are useful for both prognostic and diagnostic applications and for in vivo and in vitro imaging.

Compounds having Formula I may be incorporated into devices such as, but not limited to, arterio-venous grafts, billiary stents, by-pass grafts, catheters, central nervous system shunts, coronary stents, drug delivery balloons, peripheral stents and ureteural stents, each of which may be used in areas such as, but not limited to, the vasculature for introduction of a compound having Formula I into selected tissues or organs in the body. One measure of the effectiveness of compounds having Formula I is reduction or elimination of device-associated thrombi and complications associated therewith.

Compounds having Formula I can used as a radiosensitizers which enhance the efficacy of radiotherapy. Examples of radiotherapy include, but are not limited to, external beam radiotherapy, teletherapy, brachtherapy and sealed and unsealed source radiotherapy.

Excipients for preparation of compositions comprising a compound having Formula I to be administered orally include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water and mixtures thereof. Excipients for preparation of compositions comprising a compound having Formula I to be administered ophthalmically or orally include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound having Formula I to be administered osmotically include, for example, chlorofluoro-hydrocarbons, ethanol, water and mixtures thereof. Excipients for preparation of compositions comprising a compound having Formula I to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound having Formula I to be administered rectally or vaginally include, for example, cocoa butter, polyethylene glycol, wax and mixtures thereof.

Assay (Fam)-NoxaCF (6-FAM)-GELEVEFATQLRRFGD-KLNF-amide) (SEQ. ID NO. 1) was made on a 433A automated synthesizer (Applied Biosystems, Foster City, Calif.) using standard Fastmoc™ deprotection/coupling cycles with 0.25 mmol MBHA Rink amide resin (SynPep, Dublin, Calif.). Cartridges containing $N^{\alpha}$-Fmoc-amino acids (1 mmol) with side-chain protection (Arg: 2,2,5,7,8-pentamethylchroman-6-sulfonyl; Asp and Glu: tert-butyl ester; Asn, Cys, Gln, and His: trityl; Lys and Trp: tert-butyloxycarbonyl; Ser, Thr, and Tyr: tert-butyl ether were activated with O-benzotriazol-1-yl-N,N,N',N'-tetramethyluronium hexafluorophosphate (1 mmol), 1-hydroxybenzotriazole (1 mmol) and diisopropylethylamine (2 mmol) in N-methylpyrrolidone (NMP). The activated amino acid was coupled for 30 minutes following removal of the N-terminal Fmoc group with 20% piperidine in NMP. Labeling was accomplished by suspending the resin-bound, N-terminally deprotected side-chain protected peptide resin (0.04 mmol) and 6-carboxyfluorescein-NHS ester (57 mg) in anhydrous dimethylformamide (2 mL) containing 0.02 mL diisopropylethylamine (DIEA) and shaking at ambient temperature overnight. The resin was drained, washed 3 times with 1:1 dichloromethane/methanol and dried. The labeled resin was cleaved and deprotected by mixing with TFA:water:thioanisole:phenol:3,6-dioxa-1,8-octanedithiol:triisopropylsilane, 80:5:5:5:2.5:2.5 for 3 hours at ambient temperature. Following evaporation under reduced pressure, the crude peptide was recovered by precipitation with ether. The product was purified on a preparative HPLC running Unipoint® analysis software (Gilson, Inc., Middleton, Wis.) on a 25 mm×200 mm radial compression column containing Delta-Pak® $C_{18}$ packing (Waters, Inc., Taunton, Mass.) with a flow rate of 20 mL/min. The peptides were eluted with a linear gradient of 0.1% TFA/water and acetonitrile. Fractions containing the product were combined and lyophilized. The purity of the final products were confirmed by reverse-phase analytical HPLC on a Hewlett-Packard 1050 series system with diode-array and fluorescence detection (Agilent Technologies, Palo Alto, Calif.) eluted with a linear gradient of 0.1% trifluoroacetic acid/water and acetonitrile on a 4.6×250 mm YMC ODS-AQ, 5 μm, 120 Å column (Waters Inc.) to give the product (45.6 mg) as a yellow powder following lyophilization. The identity of the product was confirmed by matrix-assisted laser desorption ionization mass spectrography (MALDI-MS) on a Voyager DE-PRO (Applied Biosystems), m/z 1470.00 and 1448.01 (M+H)⁺.

A fluorescence polarization assay was used for $IC_{50}$ determination of representative compounds having Formula I against recombinant Mcl-1 protein. Compounds were series diluted in DMSO starting at 10 μM and transferred (5 μL) into a 96 well plate. Then, 120 μL of a mixture containing 10 nM fluorescent Noxa BH3 peptide and 80 nM Mcl-1 protein was added to each well. For each assay, free peptide controls (fluorescent peptide only) and bound peptide controls (fluorescent peptide in the presence of Mcl-1) were included on each assay plate. The plate was mixed on a shaker for 1 minute and incubated at room temperature for an additional 15 minutes. The polarization (in mP) was measured at room temperature with excitation wavelength at 485 nm and emission wavelength at 530 nm using an Analyst (LJL, Molecular Dynamic, Sunnyvale, Calif.). The percentage inhibition was calculated by % inhibition=100×(1−(mP−mP$_f$)/(mP$_b$−mP$_f$)) in which mP$_f$ is the free peptide control and mP$_b$ is the bound peptide control. Based on percentage of inhibition, the $IC_{50}$ (inhibitor concentration at which 50% of bound peptide is displaced), obtained by fitting the inhibition data using Prism 3.0 software (Graphpad Software Inc, San Diego, Calif.). The results are shown in TABLE 1.

TABLE 1

$IC_{50}$'s (in μM) For Representative Compounds Having Formula I For Inhibition of Mcl-1 Protein

| | | | | |
|---|---|---|---|---|
| <0.030 | <0.030 | <0.030 | <0.030 | 0.031 |
| 0.033 | 0.034 | 0.037 | 0.039 | 0.045 |
| 0.055 | 0.059 | 0.064 | 0.066 | 0.069 |
| 0.070 | 0.073 | 0.075 | 0.078 | 0.079 |
| 0.085 | 0.085 | 0.088 | 0.090 | 0.092 |
| 0.097 | 0.099 | 0.102 | 0.104 | 0.109 |
| 0.109 | 0.114 | 0.126 | 0.131 | 0.135 |
| 0.137 | 0.142 | 0.143 | 0.144 | 0.146 |
| 0.149 | 0.150 | 0.158 | 0.169 | 0.169 |
| 0.191 | 0.204 | 0.212 | 0.219 | 0.222 |
| 0.223 | 0.233 | 0.237 | 0.252 | 0.252 |
| 0.256 | 0.272 | 0.281 | 0.285 | 0.286 |
| 0.292 | 0.306 | 0.326 | 0.332 | 0.337 |
| 0.337 | 0.346 | 0.346 | 0.351 | 0.351 |
| 0.366 | 0.380 | 0.387 | 0.391 | 0.414 |
| 0.416 | 0.418 | 0.440 | 0.445 | 0.453 |
| 0.504 | 0.507 | 0.507 | 0.509 | 0.522 |
| 0.528 | 0.530 | 0.542 | 0.549 | 0.554 |
| 0.555 | 0.558 | 0.570 | 0.600 | 0.604 |
| 0.621 | 0.630 | 0.637 | 0.661 | 0.666 |
| 0.674 | 0.709 | 0.731 | 0.759 | 0.764 |
| 0.777 | 0.798 | 0.800 | 0.829 | 0.840 |
| 0.881 | 0.889 | 0.897 | 0.908 | 0.933 |
| 0.973 | 1.022 | 1.046 | 1.140 | 1.150 |
| 1.205 | 1.248 | 1.260 | 1.410 | 1.446 |
| 1.471 | 1.765 | 1.830 | 1.879 | 1.961 |
| 2.069 | 2.072 | 2.299 | 2.316 | 2.418 |
| 2.453 | 2.826 | 3.033 | 3.133 | 3.459 |
| 3.483 | 3.517 | 3.627 | 3.801 | 4.048 |
| 4.237 | 4.588 | 4.746 | 5.095 | 5.298 |
| 5.396 | 5.576 | 5.886 | 6.170 | 6.934 |
| 6.949 | 7.296 | 7.377 | 9.644 | 9.911 |
| 10.138 | | | | |

These data demonstrate the utility of representative compounds having Formula I as inhibitors of the activity of Mcl-1 protein.

These data demonstrate the utility of representative compounds having Formula I as inhibitors of the activity of Mcl-1 protein.

Accordingly, compounds having Formula I are expected to have utility in treatment of diseases during which anti-apopotic Mcl-1 is expressed and also utility in treatment of diseases in which anti-apoptotic family protein members having close structural homology to Mcl-1 such as, for example, Bcl-$X_L$ protein, Bcl-2 protein and Bcl-w protein are expressed.

Overexpression of Mcl-1 correlates with resistance to chemotherapy, clinical outcome, disease progression, overall prognosis or a combination thereof in various hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, cervical cancer, chondrosarcoma, chordoma, choriocarcinoma, chronic leukemia, chronic lymphocytic leukemia, chronic myelocytic (granulocytic) leukemia, chronic myeogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphagioendothelio-sarcoma, lymphangiosarcoma, lymphoblastic leukemia, lymphoma (lymphoma, including Diffuse Large B-cell lymphoma, follicular lymphomaHodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, testicular cancer (including germ cell testicular cancer) thyroid cancer, Waldenström's macroglobulinemia, testicular tumors, uterine cancer, Wilms' tumor and the like.

It is also expected that compounds having Formula I would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Involvement of Mcl-1 in acute lymphoblastic leukemia is reported in Blood 1998, 91, 991-1000.

Involvement of Mcl-1 in acute myelogenous leukemia is also reported in Blood 1998, 91, 991-1000.

Involvement of Mcl-1 in cervical cancer is reported in Cancer Letters (Shannon, Ireland) 2002, 180, 63-68.

Involvement of Mcl-1 in chronic lymphocytic leukemia is reported in Journal of the National Cancer Institute 2004, 96, 673-682 and Immunology 2005, 114, 441-449.

Involvement of Mcl-1 in colorectal cancer, is reported in Annals of oncology: Official Journal of the European Society for Medical Oncology/ESMO 2001, 12, 779-785.

Involvement of Mcl-1 in gastric carcinoma, is reported in Gastric Cancer 2004, 7, 78-84.

Involvement of Mcl-1 in gestational trophobalstic disease is reported in Cancer 2005, 103, 268-276.

Involvement of Mcl-1 in glioblastoma is reported in Journal of Neurology, Neurosurgery, and Psychiatry 1999, 67, 763-768.

Involvement of Mcl-1 in head and neck cancer is reported in Archives of Otolaryngology-Head and Neck Surgery 1999, 125, 417-422.

Involvement of Mcl-1 in lung cancer is reported in Pathology Oncology Research: POR 1999, 5, 179-186.

Involvement of Mcl-1 in mesothioloma, is reported in Clinical Cancer Research 1999, 5, 3508-3515.

Involvement of Mcl-1 in multiple myeloma is reported in European Journal of Immunology 2004, 34, 3156-3164.

Involvement of Mcl-1 in non-Hodgkin's lymphoma is reported in British Journal of Haematology 2002, 116, 158-161.

Involvement of Mcl-1 in oligodenroglioma is reported in Cancer (New York) 1999, 86, 1832-1839.

Involvement of Mcl-1 in ovarian cancer is reported in Journal of Clinical Oncology: Official Journal of the American Society of Clinical Oncology 2000, 18, 3775-3781.

Involvement of Mcl-1 in pancreatic cancer is reported in Oncology 2002, 62, 354-362.

Involvement of Mcl-1 in peripheral T-cell lymphoma is reported in Journal of Pathology 2003, 200, 240-248.

Compounds having Formula I are expected to be useful when used with alkylating agents, angiogenesis inhibitors, antibodies, antimetabolites, antimitotics, antiproliferatives, aurora kinase inhibitors, Bcl-2 family protein (for example, Bcl-xL, Bcl-2, Bcl-w, Bfl-1) inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, intercalating antibiotics, kinase inhibitors, mammalian target of rapomycin inhibitors, mitogen-activated extracellular signal-regulated kinase inhibitors, non-steroidal anti-inflammatory drugs (NSAID's), platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Alkylating agents include altretamine, AMD-473, AP-5280, apaziquone, bendamustine, brostallicin, busulfan, carboquone, carmustine (BCNU), chlorambucil, Cloretazine™ (VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Aurora kinase inhibitors include AZD-1152, MLN-8054, VX-680 and the like.

Bcl protein family member inhibitors include AT-101 ((-) gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl) benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFr immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), Herceptin® (trastuzumab), TYKERB® (lapatinib), OMNITARG® (2C4, petuzumab), TAK-165, GW-572016 (ionafamib), GW-282974, EKB-569, PI-166, dHER2 (HER2 vaccine), APC-8024 (HER-2 vaccine), anti-HER/2neu bispecific antibody, B7.her21gG3, ASHER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB®, NCS-683664, PU24FCl, PU-3, radicicol, SNX-2112, STA-9090 VER49009 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam) ibuprofin cream, ALEVE® and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™, axitinib (AG-13736), AZD-2171, CP-547,632, IM-862, Macugen (pegaptamib), NEXAVAR® (sorafenib, BAY43-9006), pazopanib (GW-786034), (PTK-787, ZK-222584), SUTENT® (sunitinib, SU-11248), VEGF trap, vatalanib, ZACTIMA™ (vandetanib, ZD-6474) and the like.

Antimetabolites include ALIMTA® (premetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR, enocitabine, ethnylcytidine, fludarabine, hydroxyurea, 5-fluorouracil (5-FU) alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosate, pelitrexol, pentostatin, raltitrexed, Ribavirin, triapine, trimetrexate, S-1, tiazofurin, tegafur, TS-1, vidarabine, UFT and the like.

Antibiotics include intercalating antibiotics aclarubicin, actinomycin D, amrubicin, annamycin, adriamycin, BLENOXANE® (bleomycin), daunorubicin, CAELYX® or MYOCET® (doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FEMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE™ (interferon gamma-1b), interferon gamma-n1, combinations thereof and the like. Other agents include ALFAFERONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanoma vaccine, mitumomab, molgramostim, MYLOTARG™ (gemtuzumab ozogamicin), NEUPOGEN® (filgrastim), Onco VAC-CL, OvaRex® (oregovomab), pemtumomab (Y-muHMFG1), PROVENGE®, sargaramostim, sizofilan, teceleukin, TheraCys®, ubenimex, VIRULIZIN®, Z-100, WF-10, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881, vinflunine, ZK-EPO and the like.

Compounds of the present invention are also intended to be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having Formula I may be combined with other chemotherapeutic agents such as ABRAXANE™ (ABI-007), ABT-100 (farnesyl transferase inhibitor), ADVEXIN®, ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotne), AVE-8062, BEC2 (mitumomab), cachectin or cachexin (tumor necrosis factor), canvaxin (vaccine), CeaVac™ (cancer vaccine), CELEUK® (celmoleukin), CEPLENE® (histamine dihydrochloride), CERVARIX™ (human papillomavirus vaccine), CHOP® (C: CYTOXAN® (cyclophosphamide); H: ADRIAMYCIN (hydroxydoxorubicin); O: Vincristine (ONCOVIN®); P: prednisone), CyPat™, combrestatin A4P, DAB(389)EGF or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906, GARDASIL® (quadrivalent human papillomavirus (Types 6, 11, 16, 18) recombinant vaccine), gastrimmune, genasense, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), OncoVAX (IL-2 Vaccine), ORATHECIN™ (rubitecan), OSIDEM® (antibody-based cell drug), OvaRex® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), Taxoprexin® (DHA-paclitaxel), TELCYTA™ (TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFerade™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS™ (trabectedin), ZD-6126, ZINECARD® (dexrazoxane), zometa (zolendronic acid), zorubicin and the like.

It is also expected that compounds having Formula I would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like (commonly-owned U.S. application Ser. No. 10/988,338), Cancer Res., 2000, 60, 6101-10); and autoimmune disorders include, acquired immunodeficiency disease syndrome, autoimmune lymphoproliferative syndrome, hemolytic anemia, inflammatory diseases, thrombocytopenia and the like (Current Allergy and Asthma Reports 2003, 3:378-384; Br. J. Haematol. 2000 September; 110(3): 584-90; Blood 2000 Feb. 15; 95(4):1283-92; and New England Journal of Medicine 2004 September; 351(14): 1409-1418).

Compounds having Formula I may be made by synthetic chemical processes, examples of which are shown hereinbelow. It is meant to be understood that the order of the steps in the processes may be varied, that reagents, solvents and reaction conditions may be substituted for those specifically mentioned, and that vulnerable moieties such as C(O)OH, C(O) and C(O)H, NH, C(O)NH$_2$, OH and SH moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

A discussion protecting groups is provided in T. H. Greene and P. G. M. Wuts, Protective Groups in Organic Synthesis, 3rd Ed., John Wiley & Sons, New York (1999).

The following abbreviations have the meanings indicated. ADDP means 1,1'-(azodicarbonyl)dipiperidine; AD-mix-β means a mixture of (DHQD)$_2$PHAL, K$_3$Fe(CN)$_6$, K$_2$CO$_3$ and K$_2$SO$_4$); 9-BBN means 9-borabicyclo(3.3.1)nonane; (DHQD)$_2$PHAL means hydroquinidine 1,4-phthalazinediyl diethyl ether; DBU means 1,8-diazabicyclo(5.4.0)undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)butane; dppe means 1,2-bis(diphenylphosphino)ethane; dppf means 1,1'-bis(diphenylphosphino)ferrocene; d means 1,1-bis(diphenylphosphino)methane; EDAC means 1-(3-dimethylaminopropyl)-3-ethylcarbodiimide; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; MP-BH$_3$ means macroporus triethylammonium methylpolystyrene cyanoborohydride; PyBOP means benzotriazol-1-yloxytripyrrolidinophosphonium hexafluorophosphate; TEA means triethylamine; TFA means trifluoroacetic acid; THF means tetrahydrofuran; NCS means N-chlorosuccinimide; NMM means N-methylmorpholine; NMP means N-methylpyrrolidine and PPh$_3$ means triphenylphosphine.

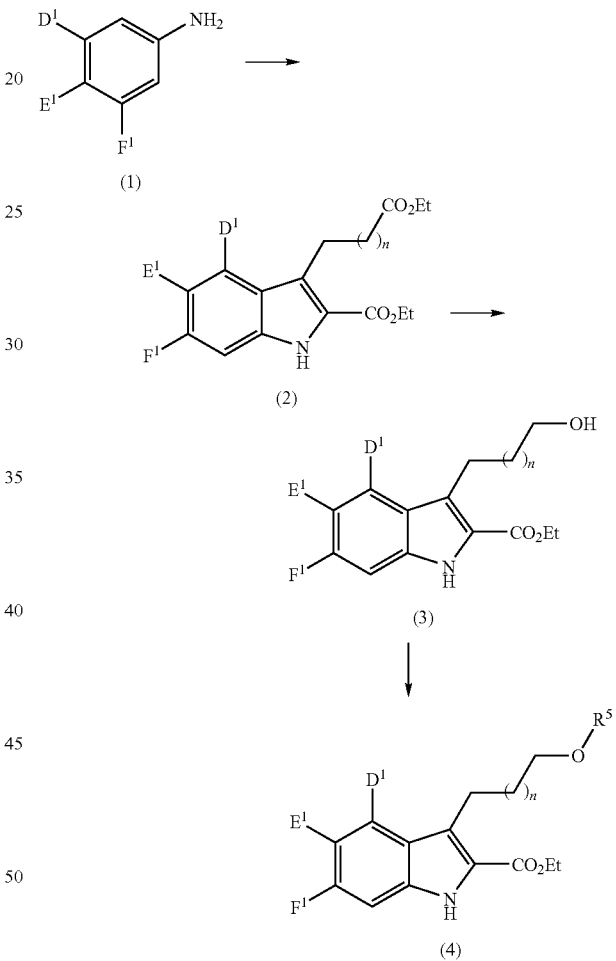

As shown in SCHEME 1, compounds of Formula (1) can be converted to compounds of Formula (2) by reacting the former with sodium nitrate and an aqueous acid followed by the addition of aqueous sodium acetate and an appropriate 2-oxocycloalkylester.

Examples of acids include hydrochloric acid and the like.

Examples of appropriate 2-oxocycloalkylesters include ethyl 2-oxocyclohexanecarboxylate, ethyl 2-oxocyclopentanecarboxylate and the like.

The reaction is initially conducted at about 0° C., over about 30 minutes to about one hour, and then warmed to between about 15° C. and 25° C. for about one to four hours, in water.

Compounds of Formula (2) can be converted to compounds of Formula (3) by reacting the former with a solution of borane.

The reaction is typically conducted at ambient temperature over about 8 hours to about 20 hours in a solvent such as but not limited to THF.

Compounds of Formula (3) can be converted to compounds of Formula (4) by reacting the former with $R^5OH$, triphenylphosphine, and a reagent such as but not limited to DEAD or TBAD.

The addition is typically conducted below room temperature before warming to ambient temperature for about 8-72 hours in a solvent such as but not limited to THF.

Introduction of moieties represented by $D^1$, $E^1$ and $F^1$ can be accomplished by reacting substituted anilines of Formula (1) as shown in SCHEME (1). Alternatively, bromoanilines of Formula (1) can be reacted as shown in SCHEME (1) and then subsequently reacted using methods described in the literature (such as those described in Palladium Reagents And Catalysts: New Perspectives For The 21st Century, By J. Tsuji, John Wiley & Sons, Ltd., Chichester, 2004, 1-670) and known by those skilled in the art for palladium catalyzed carbon cross coupling reactions.

Compounds of Formula (5) can be converted to compounds of Formula (6) by reacting the former with a base.

Examples of bases include lithium hydroxide, sodium hydroxide, potassium hydroxide and the like.

The reaction is typically conducted over about 1 hour to about 48 hours, between about 0° C. and 35° C., in solvents such as water, methanol, ethanol, isopropanol, mixtures thereof and the like.

Compounds of Formula (4), wherein $B^1$ is H, can be converted to compounds of Formula (6) by reacting the former with a base.

Examples of bases include lithium hydroxide, sodium hydroxide, potassium hydroxide and the like.

The reaction is typically conducted over about 1 hour to about 48 hours, between about 0° C. and 35° C., in solvents such as water, methanol, ethanol, isopropanol, mixtures thereof and the like.

SCHEME 2

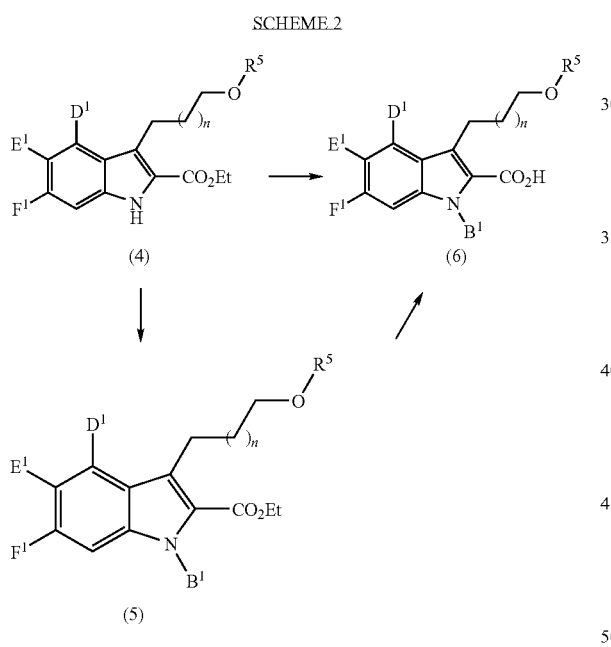

As shown in SCHEME 2, compounds of Formula (4) can be converted to compounds of Formula (5) by reacting the former with a base followed by an appropriate compound of Formula $B^1Br$ (5a) or $B^1Cl$ (5b).

Examples of a base include sodium hydride, potassium carbonate and the like.

Examples of appropriate compounds of Formula (5a) include 1-(3-bromopropoxy)naphthalene and the like.

Examples of appropriate compounds of Formula (5b) include 2-chloro-1-morpholinoethanone and the like.

The reaction is typically conducted at or below ambient temperature for about 15 minutes to one hour during the addition of the base, and then from about 20° C. to 80° C. for about one to eight hours after the addition of the compound of Formula (5a) or (5b) in a solvent such as but not limited to DMF.

SCHEME 3

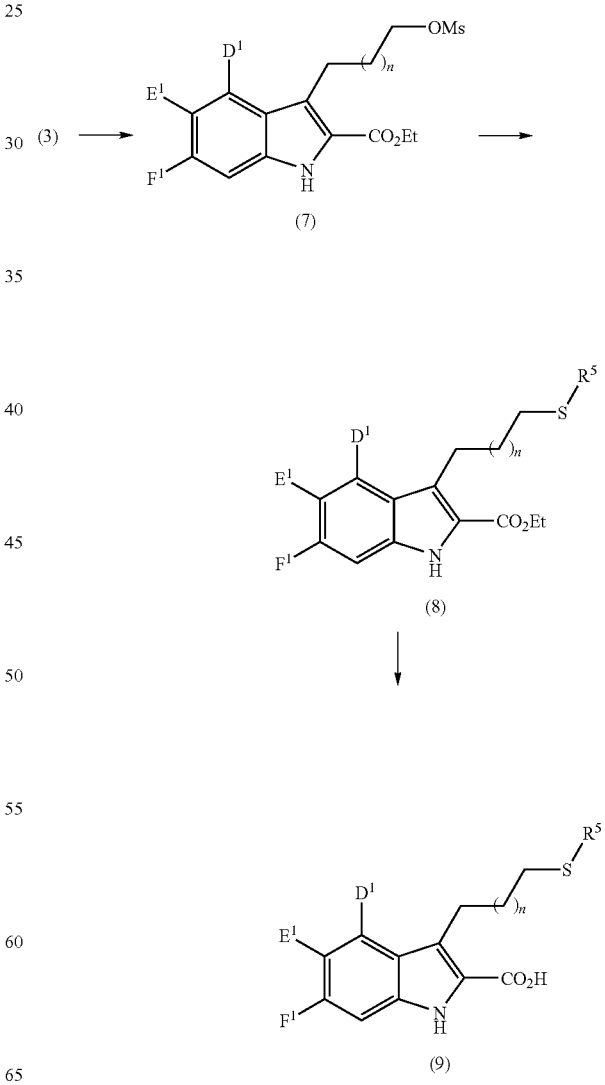

As shown in SCHEME 3, compounds of Formula (3) can be converted to compounds of Formula (7) by reacting the former with a base followed by methanesulfonyl chloride.

Examples of bases include TEA, pyridine and the like.

The reaction is typically conducted over about 30 minutes to about three hours, between about 0° C. and 20° C., in acetonitrile.

Compounds of Formula (7) can be converted to compounds of Formula (8) by reacting the former with a compound of Formula R⁵SH, and a base.

Examples of bases include potassium carbonate and sodium carbonate.

The reaction is typically conducted over one to five days between about 50° C. and 100° C., in a solvent such as but not limited to acetonitrile.

Compounds of Formula (8) can be converted to compounds of Formula (9) as described in SCHEME 2 for the conversion of compounds of Formula (4) to compounds of Formula (6).

SCHEME 4

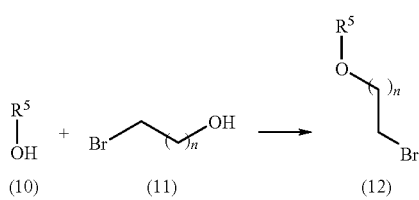

As shown in SCHEME 4, compounds of Formula (10) can be converted to compounds of Formula (12) by reacting the former with compounds of Formula (11), triphenylphosphine, and a reagent such as but not limited to DEAD or TBAD.

The addition may be conducted below room temperature before warming to ambient temperature for about 8-72 hours in a solvent such as but not limited to THF.

SCHEME 5

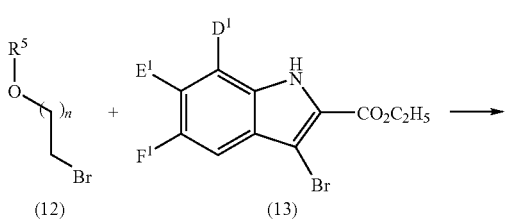

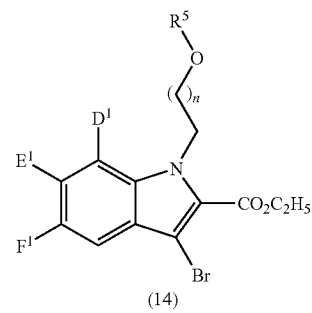

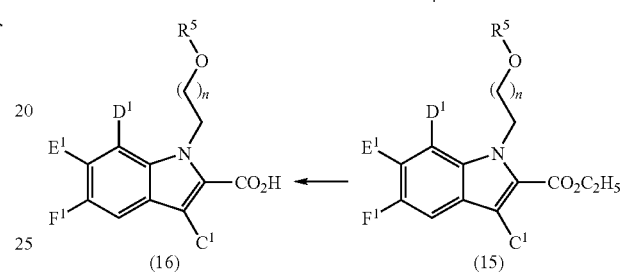

As shown in SCHEME 5, compounds of Formula (12) can be converted to compounds of Formula (14) by reacting the former, a compound of Formula (13) and a base.

Examples of bases include sodium hydride and potassium carbonate.

The reaction is typically conducted at or below ambient temperature for about 15 minutes to one hour during the addition of the base, and then from about 20° C. to 80° C. for about one to eight hours after the addition of the compound of Formula (13) in a solvent such as but not limited to DMF.

Compounds of Formula (14) can be converted to compounds of Formula (15) using methods described in the literature (such as those described in Palladium Reagents And Catalysts: New Perspectives For The 21st Century, By J. Tsuji, John Wiley & Sons, Ltd., Chichester, 2004, 1-670) and known by those skilled in the art for palladium catalyzed carbon cross coupling reactions.

Compounds of Formula (15) can be converted to compounds of Formula (16) as described in SCHEME 2 for the conversion of compounds of Formula (4) to compounds of Formula (6).

SCHEME 6

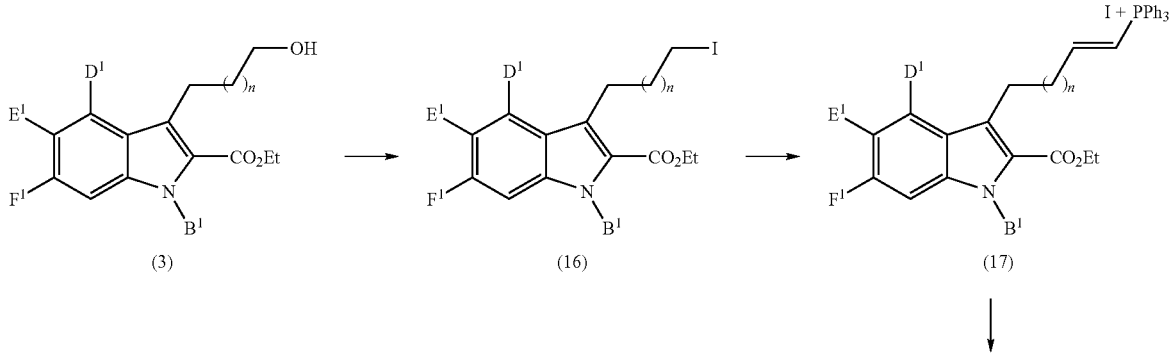

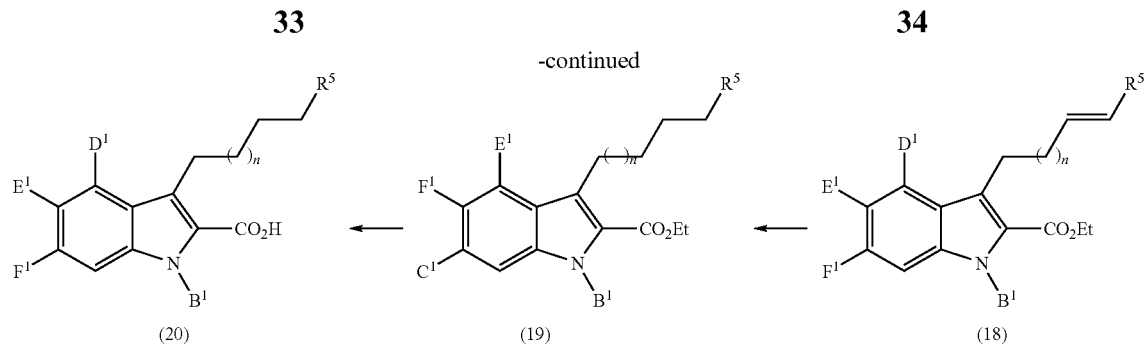

(20)  (19)  (18)

As shown in SCHEME 6, compounds of Formula (3) can be converted to compounds of Formula (16) by reacting the former, iodine, triphenyphosphine and imidazole, followed by a base.

Examples of bases include sodium carbonate and the like.

The reaction is typically conducted from about −10° C. to about 10° C. for about 15 minutes to one hour and then continued for an additional 30 minutes to one hour after addition of the base, in a solvent such as but not limited to dichloromethane.

Compounds of Formula (16) can be converted to compounds of Formula (17) by reacting the former and triphenyphosphine.

The reaction is typically conducted over about 8 to about 48 hours at reflux, in a solvent such as but not limited to acetonitrile or dichloromethane.

Compounds of Formula (17) can be converted to compounds of Formula (18) by reacting the former, a base, and a compound of Formula $R^5C(O)H$.

Examples of bases include sodium hydride and n-butyllithium.

The reaction is initially conducted over about one hour at about 60° C. to about 100° C. after the addition of the base and then cooled to about 10° C. to about 25° C. and treated with a compounds of Formula (17). After about 10 minutes to about 20 minutes, the compound of Formula $R^5C(O)H$ is added and the mixture is again heated at about 60° C. to about 100° C. for about one to eight hours.

Compounds of Formula (18) can be converted to compounds of Formula (19) by reacting the former with a hydrogen source and a catalyst.

Examples of hydrogen sources include hydrazine and hydrogen gas.

Examples of catalysts include Pd/C and Raney Nickel and the like.

Temperature and pressure vary depending on the hydrogenation method and the substrates employed. Typical solvents include methanol, ethanol, ethyl acetate, and the like.

Compounds of Formula (19) can be converted to compounds of Formula (20) as described in SCHEME 2 for the conversion of compounds of Formula (4) to compounds of Formula (6).

SCHEME 7

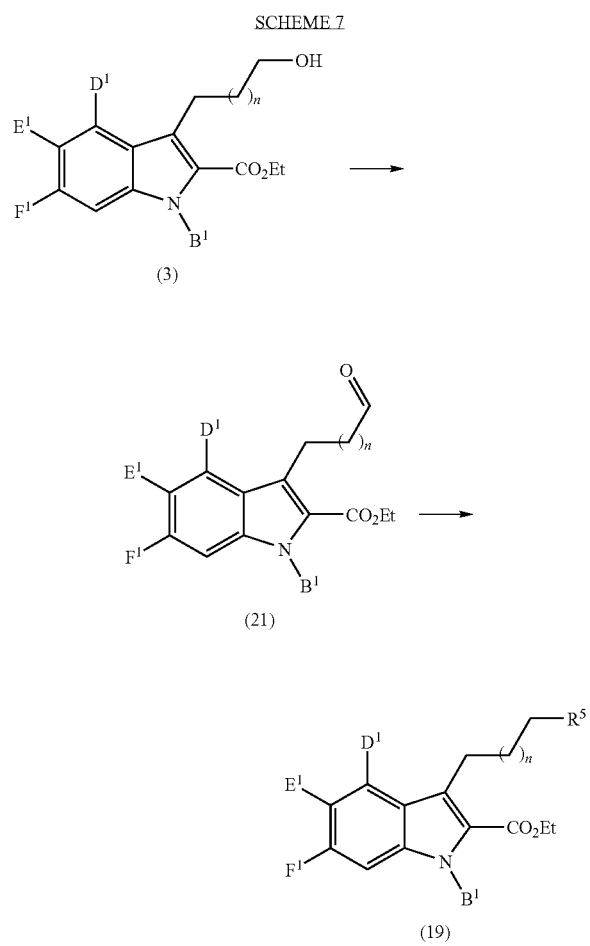

(3)

(21)

(19)

As shown in SCHEME 7, compounds of Formula (3) can be converted to compounds of Formula (21) by reacting the former, DMSO, a base, and a dehydration agent.

Examples of bases include triethylamine, diisopropylamine, and the like.

Examples of dehydration agents include oxalyl chloride, trifluoroacetic anhydride, and pyridine sulfate.

The reaction is typically conducted over about one to about eight hours at about −60° C. to about 0° C. depending on the substrate and method employed.

The following examples are presented to provide what is believed to be the most useful and readily understood description of procedures and conceptual aspects of this invention.

Example 1

3-(3-cyclohexylpropyl)-1H-indole-2-carboxylic acid

Example 2

3-(4-cyclohexylbutyl)-1H-indole-2-carboxylic acid

Example 3A ethyl 3-(3-hydroxypropyl)-1H-indole-2-carboxylate

To a mixture of ethyl 3-(3-ethoxy-3-oxopropyl)-1H-indole-2-carboxylate (2.82 g) in THF (40 mL) was added IM borane-THF (40 mL). The mixture was stirred at room temperature for 16 hours, quenched with methanol (100 mL) and concentrated. The concentrate was purified by flash column chromatography on silica gel with 5-25% ethyl acetate/hexanes.

Example 3B ethyl 3-(3-(3-chlorophenoxy)propyl)-1H-indole-2-carboxylate

A mixture of 3-chlorophenol (0.050 g), EXAMPLE 3A (0.052 g), di-tert-butyl azidicarboxylate (0.086 g) and triphenylphosphine (0.1 g) in THF (2.5 mL) was stirred at room temperature for 24 hours and concentrated. The concentrate was purified by reverse phase HPLC (Zorbax SB, C-18, 30% to 100% acetonitrile/water/0.1% trifluoroacetic acid).

Example 3C 3-(3-(3-chlorophenoxy)propyl)-1H-indole-2-carboxylic acid

A mixture of EXAMPLE 3B (0.035 mg) and LiOH (0.1 g) in methanol/water (1:1, 5 mL) was heated at 15° C. under microwave (CEM Discover) conditions (70 W) for 10 minutes. The reaction mixture was concentrated, diluted with water (2 mL), treated with 5 MHCl, and extracted with ethyl acetate. The extract was dried ($Na_2SO_4$), filtered and concentrated. The concentrate was purified by reverse phase HPLC (Zorbax SB, C-18, 20% to 100% acetonitrile/water/0.1% trifluoroacetic acid). $^1$H NMR (400 MHz, DMSO-$d_6$) δ 12.88 (brs, 1H), 11.40 (s, 1H), 7.63 (d, 1H), 7.39 (d, 1H), 7.24 (m, 2H), 6.92 (m, 4H), 3.97 (t, 2H), 3.20 (t, 2H), 2.05 (m, 2H).

Example 4A ethyl 3-(3-(3-(trifluoromethyl)phenoxy)propyl)-1H-indole-2-carboxylate This example was prepared by replacing 3-(trifluoromethyl)phenol for 3-chlorophenol in EXAMPLE 3B.

Example 4B 3-(3-(3-(trifluoromethyl)phenoxy)propyl)-1H-indole-2-carboxylic acid This example was prepared by replacing EXAMPLE 4A for EXAMPLE 3B in EXAMPLE 3C. $^1$H NMR (400 MHz, DMSO-$d_6$) δ 12.88 (brs, 1H), 11.40 (s, 1H), 7.63 (d, 1H), 7.49 (t, 1H), 7.39 (d, 1H), 7.22 (m, 4H), 6.98 (t, 1H), 4.04 (t, 2H), 3.21 (t, 2H), 2.07 (m, 2H).

Example 5A ethyl 3-(3-(naphthalen-1-yloxy)propyl)-1H-indole-2-carboxylate

This example was prepared by replacing 1-naphthol for 3-chlorophenol in EXAMPLE 3B.

Example 5B 3-(3-(naphthalen-1-yloxy)propyl)-1H-indole-2-carboxylic acid

This example was prepared by substituting EXAMPLE 5A for EXAMPLE 3B in EXAMPLE 3C. $^1$H NMR (500 MHz, DMSO-$d_6$) δ 12.96 (brs, 1H), 11.44 (s, 1H), 8.24 (d, 1H), 7.86 (d, 1H), 7.66 (d, 1H), 7.52 (m, 2H), 7.41 (m, 3H), 7.21 (t, 1H), 6.96 (t, 1H), 6.87 (d, 1H), 4.16 (t, 2H), 3.33 (m, 2H), 2.20 (m, 2H).

Example 6A ethyl 3-(3-(2-benzylphenoxy)propyl)-1H-indole-2-carboxylate

This example was prepared by substituting 2-benzylphenol for 3-chlorophenol in EXAMPLE 3B.

Example 6B 3-(3-(2-benzylphenoxy)propyl)-1H-indole-2-carboxylic acid

This example was prepared by substituting EXAMPLE 6A for EXAMPLE 3B in EXAMPLE 3C. $^1$H NMR (500 MHz, DMSO-$d_6$) δ 12.92 (brs, 1H), 11.40 (s, 1H), 7.50 (d, 1H), 7.38 (d, 1H), 7.22 (m, 5H), 7.13 (m, 3H), 6.95 (t, 1H), 6.85 (m, 2H), 3.95 (m, 4H), 3.18 (t, 2H), 2.04 (m, 2H).

Example 7A ethyl 3-(3-(2,3-dihydro-1H-inden-5-yloxy)propyl)-1H-indole-2-carboxylate This example was prepared by substituting 2,3-dihydro-1H-inden-5-ol for 3-chlorophenol in EXAMPLE 3B.

Example 7B 3-(3-(2,3-dihydro-1H-inden-5-yloxy)propyl)-1H-indole-2-carboxylic acid This example was prepared by substituting EXAMPLE 7A for EXAMPLE 3B in EXAMPLE 3C. $^1$H NMR (500 MHz, DMSO-$d_6$) δ 12.90 (brs, 1H), 11.41 (s, 1H), 7.63 (d, 1H), 7.39 (d, 1H), 7.21 (t, 1H), 7.07 (d, 1H), 7.00 (t, 1H), 6.74 (s, 1H), 6.64 (dd, 1H), 3.90 (t, 2H), 3.19 (t, 2H), 2.77 (m, 4H), 2.00 (m, 4H).

Example 8A ethyl 3-(3-(3-methylnaphthalen-1-yloxy)propyl)-1H-indole-2-carboxylate This example was prepared by substituting 3-methylnaphthalen-1-ol for 3-chlorophenol in EXAMPLE 3B.

Example 8B 3-(3-(3-methylnaphthalen-1-yloxy)propyl)-1H-indole-2-carboxylic acid This example was prepared by substituting EXAMPLE 8A for EXAMPLE 3B in EXAMPLE 3C. $^1$H NMR (500 MHz, DMSO-$d_6$) δ 12.91 (brs, 1H), 11.43 (s, 1H), 8.00 (d, 1H), 7.86 (d, 1H), 7.71 (d, 1H), 7.59 (d, 1H), 7.44 (m, 3H), 7.34 (d, 1H), 7.24 (t, 1H), 7.05 (t, 1H), 3.97 (t, 2H), 2.37 (s, 3H), 2.21 (m, 2H).

Example 9A ethyl 3-(3-(2-methylnaphthalen-1-yloxy)propyl)-1H-indole-2-carboxylate This example was prepared by substituting 2-methylnaphthalen-1-ol for 3-chlorophenol in EXAMPLE 3B.

Example 9B 3-(3-((2-methyl-1-naphthyl)oxy)propyl)-1H-indole-2-carboxylic acid This example was prepared by substituting EXAMPLE 9A for EXAMPLE 3B in EXAMPLE 3C. $^1$H NMR (500 MHz, DMSO-$d_6$) δ 12.89 (br. s, 1H), 11.4 (s, 1H), 8.00 (d, 1H), 7.86 (d, 1H), 7.70 (d, 1H), 7.59 (d, 1H), 7.45 (m, 3H), 7.34 (d, 1H), 7.5 (m, 1H), 7.05 (t, 1H), 3.97 (t, 2H), 2.37 (s, 3H), 2.15-2.26 (m, 2H).

Example 10A ethyl 3-(3-(methylsulfonyloxy)propyl)-1H-indole-2-carboxylate

To a mixture of EXAMPLE 3A (0.125 g) and triethylamine (0.21 mL) in acetonitrile (3 mL) at 0-5° C. was added methanesulfonyl chloride (0.0404 mL). After 30 minutes, the mixture was concentrated, and the concentrate was purified by flash chromatography on silica gel with 0-30% ethyl acetate/hexanes.

Example 10B ethyl 3-(3-(naphthalen-1-ylthio)propyl)-1H-indole-2-carboxylate

A mixture of EXAMPLE 10A (42 mg), naphthalene thiol (45 mg), and potassium carbonate (36 mg) in acetonitrile (2 mL) was heated at 80° C. for 3 days. The reaction mixture was poured into water, extracted with dichloromethane and purified by flash chromatography on silica gel with 0-20% ethyl acetate in hexanes.

Example 10C 3-(3-(1-naphthylthio)propyl)-1H-indole-2-carboxylic acid

This example was prepared by substituting EXAMPLE 10B for EXAMPLE 3B in EXAMPLE 3C. $^1$H NMR (300 MHz, DMSO-$d_6$) δ 12.92 (s, 1H), 11.42 (s, 1H), 8.11-8.32 (m, 1H), 7.85-8.03 (m, 1H), 7.77 (d, 1H), 7.50-7.67 (m, 2H), 7.32-7.50 (m, 2H), 7.21 (t, 1H), 6.98 (t, 1H), 3.12-3.26 (m, 2H), 3.06 (t, 2H), 1.85-2.05 (m, 2H).

Example 11A ethyl 5-bromo-3-(3-ethoxy-3-oxopropyl)-1H-indole-2-carboxylate

To a mixture of 4-bromoaniline (3.44 g) in 5M aqueous HCl (12 mL) at 0° C. was added 2.5M NaNO$_2$ (1.38 g) in water (20 mL). After the addition, 4.5M sodium acetate (9.23 g) in water (25 mL) was added, followed by 2-oxo-cyclopentanecarboxylic acid ethyl ester (3 mL). The mixture was stirred at 0° C. for 15 minutes, warmed to 19° C. over two hours, and extracted with dichloromethane. The extract was dried (MgSO$_4$), filtered and concentrated. The concentrate was dissolved in 10% H$_2$SO$_4$ in ethanol (22 mL) and refluxed overnight, cooled to room temperature, quenched with water (0.4 L), and filtered.

Example 11B ethyl 5-bromo-3-(3-hydroxypropyl)-1H-indole-2-carboxylate

This example was prepared by substituting EXAMPLE 11A for ethyl 3-(3-ethoxy-3-oxopropyl)-1H-indole-2-carboxylate in EXAMPLE 3A.

Example 11C ethyl 5-bromo-(3-(3-(naphthalen-1-yloxy)propyl))-1H-indole-2-carboxylate This example was prepared by substituting 1-naphthol for 3-chlorophenol and EXAMPLE 11B for EXAMPLE 3A in EXAMPLE 3B.

Example 11D 5-bromo-(3-(3-(naphthalen-1-yloxy)propyl))-1H-indole-2-carboxylic Acid This example was prepared by substituting EXAMPLE 11C for EXAMPLE 3B in EXAMPLE 3C. $^1$H NMR (400 MHz, DMSO-$d_6$) δ 13.14 (brs, 1H), 11.63 (s, 1H), 8.23 (m, 1H), 7.85 (m, 2H), 7.49 (m, 3H), 7.33 (m, 3H), 6.86 (d, 1H), 4.15 (t, 2H), 2.19 (m, 2H).

Example 12

3-(3-(1-naphthyloxy)propyl)-5-((1E)-3-phenylprop-1-enyl)-1H-indole-2-carboxylic Acid A mixture of EXAMPLE 11C (45.2 mg), (E)-3-phenylprop-1-enylboronic acid (21.1 mg), bis(triphenylphosphine)palladium(II) dichloride (catalytic), and 2M LiOH (0.3 mL) in 7/2/3 dimethoxyethane/ethanol/H$_2$O (2 mL) was heated under microwave (CEM Discover) conditions at 150° C. for 30 minutes. The mixture was quenched with 1 MHCl (0.4 mL) and extracted with ethyl acetate. The extract was dried (MgSO$_4$), filtered, and concentrated. The cruconcentrate was purified by reverse phase HPLC (Zorbax SB-C18, 20-100% acetonitrile/water/0.1% trifluoroacetic acid). $^1$H NMR (500 MHz, DMSO-$d_6$) δ 12.95 (brs, 1H), 11.44 (s, 1H), 8.34 (d, 1H), 7.88 (d, 1H), 7.54 (m, 2H), 7.44 (m, 2H), 7.31 (m, 5H), 7.18 (m, 3H), 6.83 (d, 1H), 6.00 (m, 2H), 4.08 (t, 2H), 2.21 (m, 2H).

Example 13

5-((E)-2-cyclohexylvinyl)-3-(3-(1-naphthyloxy)propyl)-1H-indole-2-carboxylic acid This example was prepared by substituting (E)-2-cyclohexylvinylboronic acid for (E)-3-phenylprop-1-enylboronic acid in EXAMPLE 12. $^1$H NMR (500 MHz, DMSO-$d_6$) δ 12.95 (brs, 1H), 11.42 (s, 1H), 8.36 (m, 1H), 7.88 (m, 1H), 7.56 (m, 2H), 7.43 (m, 2H), 7.34 (m, 1H), 7.26 (m, 2H), 6.81 (d, 1H), 5.80 (m, 2H), 4.07 (t, 2H), 2.21 (t, 2H), 1.85 (m, 1H), 1.62 (m, 5H), 1.20 (m, 3H), 0.92 (m, 2H).

Example 14

3-(3-(1-naphthyloxy)propyl)-5-((E)-2-phenylvinyl)-1H-indole-2-carboxylic acid

This example was prepared by substituting (E)-styrylboronic acid for (E)-3-phenylprop-1-enylboronic acid in EXAMPLE 12. $^1$H NMR (400 MHz, DMSO-$d_6$) δ 13.03 (br. s, 1H), 11.56 (s, 1H), 8.39 (m, 1H), 7.92 (m, 1H), 7.58 (m, 4H), 7.43 (d, 1H), 7.28 (m, 7H), 6.92 (d, 1H), 6.84 (d, 1H), 6.68 (d, 1H), 4.10 (t, 2H), 3.39 (t, 2H), 2.25 (m, 2H).

Example 15

5-(4-fluorophenyl)-3-(3-(1-naphthyloxy)propyl)-1H-indole-2-carboxylic acid

This example was prepared by substituting 4-fluoro-phenylboronic acid for (E)-3-phenylprop-1-enylboronic acid in EXAMPLE 12. $^1$H NMR (500 MHz, DMSO-$d_6$) δ 13.05 (brs, 1H), 11.56 (s, 1H), 8.33 (d, 1H), 7.92 (d, 1H), 7.71 (s, 1H), 7.50 (m, 5H), 7.35 (t, 1H), 7.20 (m, 2H), 6.96 (m, 2H), 6.85 (d, 1H), 4.11 (t, 2H), 3.40 (t, 2H), 2.25 (m, 2H).

Example 16

3-(3-(1-naphthyloxy)propyl)-5-(2-phenylethyl)-1H-indole-2-carboxylic acid

A mixture of EXAMPLE 14 (0.005 g), cyclohexene (0.5 mL), Pd/C (catalytic) in ethanol (4 mL) was heated at 130° C. (270 W) in a microwave (CEM Discover) for 10 minutes. The reaction mixture was filtered and the filtrate was concentrated. The concentrate was purified by preparative reverse phase HPLC (Zorbax SB, C-18, 20% to 100% acetonitrile/water/0.1% trifluoroacetic acid) to afford the title compound. $^1$H NMR (500 MHz, DMSO-$d_6$) δ 12.88 (brs, 1H), 11.32 (s, 1H), 8.34 (m, 1H), 7.84 (m, 1H), 7.53 (m, 2H), 7.42 (d, 1H), 7.34 (m, 2H), 7.23 (m, 3H), 7.13 (m, 1H), 7.01 (m, 3H), 6.84 (d, 1H), 4.08 (t, 2H), 2.56 (s, 4H), 2.19 (m, 2H).

Example 17

3-(3-((7-methyl-2,3-dihydro-1H-inden-4-yl)oxy)propyl)-1H-indole-2-carboxylic acid

Example 17A

This example was prepared by substituting 7-methyl-2,3-dihydro-1H-inden-4-ol for 3-chlorophenol in EXAMPLE 3B.

Example 17B 3-(3-((7-methyl-2,3-dihydro-1H-inden-4-yl)oxy)propyl)-1H-indole-2-carboxylic acid This example was prepared by substituting EXAMPLE 17A for EXAMPLE 3B in EXAMPLE 3C. $^1$H NMR (500 MHz, CHLOROFORM-d) δ 8.72 (s, 1H), 7.73 (d, 1H), 7.36 (m, 2H), 7.14 (t, 1H), 6.87 (d, 1H), 6.55 (d, 1H), 4.03 (t, 2H), 3.34 (t, 2H), 2.95 (t, 2H), 2.84 (t, 2H), 2.19 (m, 5H), 2.09 (m, 2H).

Example 18A ethyl 3-(3-(5,6,7,8-tetrahydronaphthalen-1-yloxy)propyl)-1H-indole-2-carboxylate This example was prepared by substituting 5,6,7,8-tetrahydronaphthalen-1-ol for 3-chlorophenol in EXAMPLE 3B.

Example 18B 3-(3-(5,6,7,8-tetrahydronaphthalen-1-yloxy)propyl)-1H-indole-2-carboxylic acid This example was prepared by substituting EXAMPLE 18A for EXAMPLE 3B in EXAMPLE 3C. $^1$H NMR (500 MHz, CHLOROFORM-d) δ 8.75 (s, 1H), 7.73 (d, 1H), 7.38 (m, 2H), 7.14 (t, 1H), 7.01 (t, 1H), 6.68 (d, 1H), 6.60 (d, 1H), 4.03 (t, 2H), 3.37 (t, 2H), 2.76 (m, 4H), 2.22 (m, 2H), 1.80 (m, 4H).

Example 19A ethyl 4-bromo-3-(3-ethoxy-3-oxopropyl)-1H-indole-2-carboxylate

This example was prepared by substituting 3-bromoaniline for 4-bromoaniline in EXAMPLE 1A.

Example 19B ethyl 4-bromo-3-(3-hydroxypropyl)-1H-indole-2-carboxylate

This example was prepared by substituting EXAMPLE 19A for ethyl 3-(3-ethoxy-3-oxopropyl)-1H-indole-2-carboxylate in EXAMPLE 3A.

Example 19C ethyl 4-bromo-(3-(3-(naphthalen-1-yloxy)propyl))-1H-indole-2-carboxylate This example was prepared by substituting 1-naphthol for 3-chlorophenol and EXAMPLE 19B for EXAMPLE 3A in EXAMPLE 3B.

Example 19D 4-(4-fluorophenyl)-3-(3-(1-naphthyloxy)propyl)-1H-indole-2-carboxylic acid This example was prepared by substituting 4-fluoro-phenylboronic acid for (E)-3-phenylprop-1-enylboronic acid and EXAMPLE 19C for EXAMPLE 11C in EXAMPLE 12. $^1$H NMR (500 MHz, CHLOROFORM-d) δ 8.76 (s, 1H), 7.73 (d, 1H), 7.38 (m, 2H), 7.14 (t, 1H), 7.02 (t, 1H), 6.68 (d, 1H), 6.59 (d, 1H), 4.02 (t, 2H), 3.37 (t, 2H), 2.75 (m, 4H), 2.22 (m, 2H), 1.80 (m, 4H).

Example 20A ethyl 6-bromo-3-(3-ethoxy-3-oxopropyl)-1H-indole-2-carboxylate

This example was prepared by substituting 3-bromoaniline for 4-bromoaniline in EXAMPLE 1A.

Example 20B ethyl 6-bromo-3-(3-hydroxypropyl)-1H-indole-2-carboxylate

This example was prepared by substituting EXAMPLE 20A for ethyl 3-(3-ethoxy-3-oxopropyl)-1H-indole-2-carboxylate in EXAMPLE 3A.

Example 20C ethyl 6-bromo-3-(3-(naphthalen-1-yloxy)propyl))-1H-indole-2-carboxylate This example was prepared by substituting 1-naphthol for 3-chlorophenol and EXAMPLE 20B for EXAMPLE 3A in EXAMPLE 3B.

Example 20D 3-(3-(1-naphthyloxy)propyl)-6-((E)-2-phenylvinyl)-1H-indole-2-carboxylic acid This example was prepared by substituting (E)-styrylboronic acid for (E)-3-phenylprop-1-enylboronic acid and EXAMPLE 20C for EXAMPLE 11C in EXAMPLE 12. $^1$H NMR (500 MHz, DMSO-d$_6$) δ 12.98 (brs, 1H), 11.53 (s, 1H), 8.24 (m, 1H), 7.86 (m, 1H), 7.64 (m, 3H), 7.53 (m, 3H), 7.45 (m, 1H), 7.36 (m, 5H), 7.21 (m, 2H), 6.88 (d, 1H), 4.17 (t, 2H), 2.21 (m, 2H).

Example 21

3-(3-(1-naphthyloxy)propyl)-6-((1 E)-3-phenylprop-1-enyl)-1H-indole-2-carboxylic acid This example was prepared by substituting EXAMPLE 20C for EXAMPLE 11C in EXAMPLE 12. $^1$H NMR (500 MHz, DMSO-d$_6$) δ 12.94 (brs, 1H), 11.39 (s, 1H), 8.21 (d, 1H), 7.86 (d, 1H), 7.54 (m, 3H), 7.44 (m, 1H), 7.32 (m, 6H), 7.21 (m, 1H), 7.12 (d, 1H), 6.87 (d, 1H), 6.55 (d, 1H), 6.37 (m, 1H), 4.14 (t, 2H), 3.54 (d, 2H), 2.19 (m, 2H).

Example 22

3-(3-(1-naphthyloxy)propyl)-4-((1 E)-3-phenylprop-1-enyl)-1H-indole-2-carboxylic acid This example was prepared by substituting EXAMPLE 19C for EXAMPLE 11C in EXAMPLE 12. $^1$H NMR (500 MHz, DMSO-d$_6$) δ 13.01 (brs, 1H), 11.49 (s, 1H), 8.19 (m, 1H), 7.81 (m, 1H), 7.33 (m, 13H), 6.91 (d, 1H), 6.32 (m, 1H), 4.14 (t, 2H), 3.55 (m, 2H), 3.45 (m, 2H), 2.12 (m, 2H).

Example 23

6-(3-(benzyloxy)phenyl)-3-(3-(1-naphthyloxy)propyl)-1H-indole-2-carboxylic acid

This example was prepared by substituting 3-(benzyloxy)phenylboronic acid for (E)-3-phenylprop-1-enylboronic acid and EXAMPLE 20C for EXAMPLE 11C in EXAMPLE 12. $^1$H NMR (500 MHz, DMSO-d$_6$) δ 13.03 (s, 1H), 11.52 (s, 1H), 8.24 (m, 1H), 7.86 (s, 1H), 7.73 (d, 1H), 7.60 (s, 1H), 7.35 (m, 13H), 7.01 (m, 1H), 6.88 (d, 1H), 5.18 (s, 2H), 4.18 (t, 2H), 2.24 (m, 2H).

Example 24

4-(3-(benzyloxy)phenyl)-3-(3-(1-naphthyloxy)propyl)-1H-indole-2-carboxylic acid

This example was prepared by substituting 3-(benzyloxy)phenylboronic acid for (E)-3-phenylprop-1-enylboronic acid and EXAMPLE 19C for EXAMPLE 11C in EXAMPLE 12. $^1$H NMR (500 MHz, DMSO-d$_6$) δ 12.98 (brs, 1H), 11.62 (s, 1H), 8.03 (d, 1H), 7.83 (d, 1H), 7.47 (m, 4H), 7.34 (m, 4H), 7.24 (m, 4H), 7.03 (m, 3H), 6.83 (d, 1H), 6.70 (d, 1H), 5.07 (s, 2H), 3.65 (m, 2H), 2.84 (m, 2H), 1.72 (m, 2H).

Example 25A ethyl 5-bromo-3-(4-ethoxy-4-oxobutyl)-1H-indole-2-carboxylate

This example was prepared by substituting ethyl 2-oxocyclohexanecarboxylate for ethyl 2-oxocyclopentanecarboxylate in EXAMPLE 11A.

Example 25B ethyl 5-bromo-3-(4-hydroxybutyl)-1H-indole-2-carboxylate

This example was prepared by substituting EXAMPLE 25A for ethyl 3-(3-ethoxy-3-oxopropyl)-1H-indole-2-carboxylate in EXAMPLE 3A.

Example 25C ethyl 5-bromo-3-(4-(naphthalen-1-yloxy)butyl)-1H-indole-2-carboxylate This example was prepared by substituting 1-naphthol for 3-chlorophenol and EXAMPLE 25B for EXAMPLE 3A in EXAMPLE 3B.

Example 25D 5-bromo-3-(4-(1-naphthyloxy)butyl)-1H-indole-2-carboxylic acid

This example was prepared by substituting EXAMPLE 25C for EXAMPLE 3B in EXAMPLE 3C. $^1$H NMR (500 MHz, DMSO-d$_6$) δ 13.11 (brs, 1H), 11.61 (s, 1H), 8.09 (d, 1H), 7.89 (s, 1H), 7.84 (d, 1H), 7.47 (m, 3H), 7.36 (m, 3H), 6.93 (d, 1H), 4.16 (m, 2H), 3.16 (m, 2H), 1.88 (m, 4H).

Example 26A ethyl 1-methyl-3-(3-(naphthalen-1-yloxy)propyl)-1H-indole-2-carboxylate To a mixture of 60% oily NaH (20 mg) in DMF (5 mL) was added EXAMPLE 5A (0.1 g). After stirring at room temperature for 30 minutes, CH$_3$I (0.1 mL) was added, and the mixture was stirred for 16 hours. Water and dichloromethane were added to the mixture, and the extract was separated and concentrated.

Example 26B 1-methyl-3-(3-(1-naphthyloxy)propyl)-1H-indole-2-carboxylic acid

This example was prepared by substituting EXAMPLE 26A for EXAMPLE 3B in EXAMPLE 3C. $^1$H NMR (500 MHz, DMSO-d$_6$) δ 13.12 (brs, 1H), 8.20 (d, 1H), 7.86 (d, 1H), 7.69 (d, 1H), 7.52 (m, 3H), 7.44 (d, 1H), 7.37 (t, 1H), 7.30 (t, 1H), 7.00 (t, 1H), 6.87 (d, 1H), 4.15 (t, 2H), 3.96 (s, 3H), 2.19 (m, 2H).

Example 27

3-(3-(1-naphthyloxy)propyl)-6-phenyl-1H-indole-2-carboxylic acid

This example was prepared by substituting phenylboronic acid for (E)-3-phenylprop-1-enylboronic acid and EXAMPLE 20C for EXAMPLE 11C in EXAMPLE 12. $^1$H NMR (500 MHz, DMSO-d$_6$) δ 13.00 (brs, 1H), 11.65 (s, 1H), 8.01 (d, 1H), 7.83 (d, 1H), 7.43 (m, 10H), 7.28 (m, 1H), 6.83 (d, 1H), 6.70 (d, 1H), 3.65 (t, 2H), 2.88 (m, 2H), 1.67 (m, 2H).

Example 28

6-(2-methylphenyl)-3-(3-(1-naphthyloxy)propyl)-1H-indole-2-carboxylic acid

This example was prepared by substituting 2-methylphenylboronic acid for (E)-3-phenylprop-1-enylboronic acid and EXAMPLE 20C for EXAMPLE 11C in EXAMPLE 12. $^1$H NMR (500 MHz, DMSO-d$_6$) δ 12.97 (brs, 1H), 11.62 (s, 1H), 8.03 (d, 1H), 7.83 (d, 1H), 7.37 (m, 10H), 6.72 (m, 2H), 3.60 (m, 2H), 2.91 (m, 1H), 2.42 (m, 1H), 1.99 (s, 3H), 1.66 (m, 2H).

Example 29

6-(3-methylphenyl)-3-(3-(1-naphthyloxy)propyl)-1H-indole-2-carboxylic acid

This example was prepared by substituting 3-methylphenylboronic acid for (E)-3-phenylprop-1-enylboronic acid and EXAMPLE 20C for EXAMPLE 11C in EXAMPLE 12. $^1$H NMR (500 MHz, DMSO-d$_6$) δ 12.99 (brs, 1H), 11.64 (s, 1H), 8.01 (d, 1H), 7.83 (d, 1H), 7.35 (m, 10H), 6.82 (d, 1H), 6.72 (d, 1H), 3.67 (m, 2H), 2.85 (m, 2H), 2.30 (s, 3H), 1.74 (m, 2H).

Example 30

6-(4-methylphenyl)-3-(3-(1-naphthyloxy)propyl)-1H-indole-2-carboxylic acid

This example was prepared by substituting 4-methylphenylboronic acid for (E)-3-phenylprop-1-enylboronic acid and EXAMPLE 20C for EXAMPLE 11C in EXAMPLE 12. $^1$H NMR (500 MHz, DMSO-d$_6$) δ 12.98 (s, 1H), 11.61 (s, 1H), 8.00 (d, 1H), 7.83 (d, 1H), 7.36 (m, 10H), 6.80 (d, 1H), 6.70 (d, 1H), 3.63 (t, 2H), 2.90 (m, 2H), 2.29 (s, 3H), 1.69 (m, 2H).

Example 31A 1-(3-bromopropoxy)naphthalene

A mixture of 1-naphthol (3.45 g), 3-bromopropanol (1.75 mL), di-t-butyl-azo-dicarboxylate (5.52 g) and triphenylphosphine (6.28 g) in THF (30 mL) was stirred at room temperature for 16 hours and concentrated. The concentrate was diluted with ethyl acetate, washed with water and brine and dried (MgSO$_4$), filtered, and concentrated. The concentrate was purified by silica gel chromatography with 0-7% ethyl acetate/hexane.

Example 31B ethyl 3-bromo-1H-indole-2-carboxylate

A mixture of ethyl-2-indole carboxylate (1.89 g) and N-bromosuccinimide (1.77 g) in THF (30 mL) was stirred at room temperature for 1 hour. The mixture was poured into water (150 mL) and filtered. The filtrant was washed with THF, dried under vacuum at 60° C., and recrystallized from ethyl acetate/hexanes.

Example 31C ethyl 3-bromo-1-(3-(naphthalen-1-yloxy)propyl)-1H-indole-2-carboxylate EXAMPLE 31B (0.58 g) was added to a mixture of NaH (0.112 g) in DMF (5 mL). The mixture was stirred for 30 minutes, treated with EXAMPLE 31A (0.532 g) in DMF (3 mL), stirred at 80° C. for 1 hour, quenched with saturated NH$_4$Cl, and extracted with ethyl acetate. The extract was washed with water, and brine and dried (MgSO$_4$), filtered, and concentrated. The concentrate was purified by silica gel chromatography with 0-7% ethyl acetate/hexanes.

Example 31D ethyl 1-(3-(naphthalen-1-yloxy)propyl)-3-ortho-tolyl-1H-indole-2-carboxylate A mixture of EXAMPLE 31C (90 mg), ortho-tolboronic acid (54 mg), tris(dibenzylideneacetone)dipalladium(0) (18 mg), tri-tert-butylphosphine tetrafluoroborate (5.8 mg), CsF (90 mg) in THF (2 mL) was stirred at room temperature for 16 hours, diluted with ethyl acetate and was washed with water and brine. The combine extract was dried (MgSO$_4$), filtered, and concentrated.

Example 31E 3-(2-methylphenyl)-1-(3-(1-naphthyloxy)propyl)-1H-indole-2-carboxylic acid A mixture of EXAMPLE 31D in 1N LiOH:dioxane (0.5 mL: 2 mL) was heated under microwave conditions (CEM Discover) at 130° C. for 30 minutes. The mixture was quenched with 1NHCl aqueous mixture (0.5 mL) and extracted with ethyl acetate. The extract was dried ($Na_2SO_4$), filtered, and concentrated. The concentrate was purified by reverse phase HPLC (Zorbax SB-C18, 20-100% acetonitrile/water/0.1% trifluoroacetic acid). $^1$H NMR (400 MHz, DMSO-$d_6$) δ 12.73 (bs, 1H), 8.23 (d, 1H), 7.87 (d, 1H), 7.66 (d, 1H), 7.52 (m, 3H), 7.38 (t, 1H), 7.26 (m, 4H), 7.12 (m, 2H), 7.04 (m, 1H), 6.87 (d, 2H), 4.91 (t, 2H), 4.19 (t, 2H), 2.38 (m, 2H), 2.01 (s, 3H).

Example 32A ethyl 3-(naphthalen-1-yl)-1-(3-(naphthalen-1-yloxy)propyl)-1H-indole-2-carboxylate This example was prepared by substituting ortho-tolylboronic acid with 1-naphthaleneboronic acid in EXAMPLE 31D.

Example 32B 3-(1-naphthyl)-1-(3-(1-naphthyloxy)propyl)-1H-indole-2-carboxylic acid This example was prepared by substituting EXAMPLE 31D with EXAMPLE 32A in EXAMPLE 31E. $^1$H NMR (400 MHz, DMSO-$d_6$) δ 12.61 (bs, 1H), 8.22 (d, 1H), 7.96 (m, 2H), 7.87 (d, 1H), 7.74 (d, 1H), 7.48 (m, 8H), 7.31 (m, 1H), 7.25 (m, 1H), 7.02 (m, 2H), 6.91 (d, 1H), 4.98 (t, 2H), 4.25 (t, 2H), 2.45 (m, 2H).

Example 33A ethyl 3-(3-(3-(dimethylamino)propylcarbamoyl)phenyl)-1-(3-(naphthalen-1-yloxy)propyl)-1H-indole-2-carboxylate This example was prepared by substituting ortho-tolylboronic acid with N-(3-(N',N'-dimethylamino)propyl)benzamide-3-boronic acid pinacol ester in EXAMPLE 31D.

Example 33B 3-(3-(((3-(dimethylamino)propyl)amino)carbonyl)phenyl)-1-(3-(1-naphthyloxy)propyl)-1H-indole-2-carboxylic acid This example was prepared by substituting EXAMPLE 31D with EXAMPLE 33A in EXAMPLE 31E. $^1$H NMR (400 MHz, DMSO-$d_6$) δ 12.06 (bs, 1H), 8.64 (t, 1H), 8.25 (d, 1H), 7.93 (s, 1H), 7.86 (m, 2H), 7.70 (d, 1H), 7.53 (m, 5H), 7.39 (m, 2H), 7.27 (m, 1H), 7.11 (m, 1H), 6.89 (d, 1H), 4.89 (t, 2H), 4.20 (t, 2H), 3.10 (t, 2H), 2.78 (s, 6H), 2.38 (m, 2H), 1.88 (m, 2H).

Example 34A ethyl 3-(biphenyl-2-yl)-1-(3-(naphthalen-1-yloxy)propyl)-1H-indole-2-carboxylate This example was prepared by substituting ortho-tolylboronic acid with 2-biphenylboronic acid in EXAMPLE 31D.

Example 34B 3-(1,1'-biphenyl-2-yl)-1-(3-(1-naphthyloxy)propyl)-1H-indole-2-carboxylic acid This example was prepared by substituting EXAMPLE 31D with EXAMPLE 34A in EXAMPLE 31E. $^1$H NMR (400 MHz, DMSO-$d_6$) δ 12.68 (br, 1H), 8.24 (d, 1H), 7.86 (d, 1H), 7.52 (m, 3H), 7.38 (m, 6H), 7.08 (m, 7H), 6.93 (m, 1H), 6.76 (d, 1H), 4.78 (m, 2H), 4.00 (m, 2H), 2.22 (m, 2H).

Example 35A 2-(3-bromopropoxy)naphthalene

This example was prepared by substituting 1-naphthol with 2-naphthol in EXAMPLE 31A.

Example 35B ethyl 3-bromo-1-(3-(naphthalen-2-yloxy)propyl)-1H-indole-2-carboxylate This example was prepared by substituting EXAMPLE 31A with EXAMPLE 35A in EXAMPLE 31C.

Example 35C ethyl 1-(3-(naphthalen-2-yloxy)propyl)-3-ortho-tolyl-1H-indole-2-carboxylate This example was prepared by substituting EXAMPLE 31C with EXAMPLE 35B in EXAMPLE 31D.

Example 35D 3-(2-methylphenyl)-1-(3-(2-naphthyloxy)propyl)-1H-indole-2-carboxylic acid This example was prepared by substituting EXAMPLE 31D with EXAMPLE 35C in EXAMPLE 31E. $^1$H NMR (400 MHz, DMSO-$d_6$) δ 12.69 (br, 1H), 7.82 (m, 2H), 7.73 (d, 1H), 7.66 (d, 1H), 7.44 (m, 1H), 7.33 (m, 1H), 7.21 (m, 7H), 7.09 (m, 1H), 7.04 (m, 1H), 4.84 (t, 2H), 4.07 (t, 2H), 2.30 (m 2H), 2.01 (s, 3H).

Example 36A 5-(3-bromopropoxy)-1,2,3,4-tetrahydronaphthalene

This example was prepared by substituting 1-naphthol with 5,6,7,8-tetrahydro-1-naphthol in EXAMPLE 31A.

Example 36B ethyl 3-bromo-1-(3-(5,6,7,8-tetrahydronaphthalen-1-yloxy)propyl)-1H-indole-2-carboxylate This example was prepared by substituting EXAMPLE 31A with EXAMPLE 36A in EXAMPLE 31C.

Example 36C ethyl 1-(3-(5,6,7,8-tetrahydronaphthalen-1-yloxy)propyl)-3-ortho-tolyl-1H-indole-2-carboxylate This example was prepared by substituting EXAMPLE 3°C. with EXAMPLE 36B in EXAMPLE 31D.

Example 36D 3-(2-methylphenyl)-1-(3-(5,6,7,8-tetrahydronaphthalen-1-yloxy)propyl)-1H-indole-2-carboxylic acid This example was prepared by substituting EXAMPLE 31D with EXAMPLE 36C in EXAMPLE 31E. $^1$H NMR (400 MHz, DMSO-$d_6$) δ 12.69 (br, 1H), 7.62 (d, 1H), 7.29 (m, 4H), 7.09 (m, 3H), 6.98 (m, 1H), 6.64 (m, 2H), 4.79 (t, 2H), 3.96 (t, 2H), 2.68 (m 2H), 2.61 (t, 2H), 2.23 (m, 2H), 2.02 (s, 3H), 1.71 (m, 4H).

Example 37A ethyl 1-(3-(naphthalen-1-yloxy)propyl)-3-m-tolyl-1H-indole-2-carboxylate This example was prepared by substituting ortho-tolylboronic acid with m-tolylboronic acid in EXAMPLE 31D.

Example 37B 3-(3-methylphenyl)-1-(3-(1-naphthyloxy)propyl)-1H-indole-2-carboxylic acid This example was prepared by substituting EXAMPLE 31D with EXAMPLE 37A in EXAMPLE 31E. $^1$H NMR (400 MHz, DMSO-$d_6$) δ 12.95 (br, 1H), 8.21 (d, 1H), 7.87 (d, 1H), 7.66 (d, 1H), 7.50 (m, 4H), 7.38 (m, 1H), 7.31 (m, 1H), 7.24 (m, 1H), 7.19 (s, 1H), 7.16 (m, 2H), 7.09 (m, 1H), 6.88 (d, 1H), 4.85 (t, 2H), 4.19 (t, 2H), 2.37 (m 2H), 2.35 (s, 3H).

Example 38A ethyl 3-(3-chlorophenyl)-1-(3-(naphthalen-1-yloxy)propyl)-1H-indole-2-carboxylate This example was prepared by substituting ortho-tolylboronic acid with 3-chlorophenylboronic acid in EXAMPLE 31D.

Example 38B 3-(3-chlorophenyl)-1-(3-(1-naphthyloxy)propyl)-1H-indole-2-carboxylic acid This example was prepared by substituting EXAMPLE 31D with EXAMPLE 38A in EXAMPLE 31E. $^1$H NMR (400 MHz, DMSO-$d_6$) δ 13.11 (br, 1H), 8.17 (d, 1H), 7.87 (d, 1H), 7.69 (d, 1H), 7.45 (m, 8H), 7.25 (m, 2H), 7.12 (m, 1H), 6.88 (d, 1H), 4.88 (t, 2H), 4.20 (t, 2H), 2.38 (m, 2H).

Example 39A ethyl 1-(3-(naphthalen-1-yloxy)propyl)-3-phenyl-1H-indole-2-carboxylate This example was prepared by substituting ortho-tolylboronic acid with phenylboronic acid in EXAMPLE 31D.

Example 39B 1-(3-(1-naphthyloxy)propyl)-3-phenyl-1H-indole-2-carboxylic acid This example was prepared by substituting EXAMPLE 31D with EXAMPLE 39A in EXAMPLE 31E. $^1$H NMR (400 MHz, DMSO-$d_6$) δ 12.99 (br, 1H), 8.24 (d, 1H), 7.87 (d, 1H), 7.66 (d, 1H), 7.52 (m, 2H), 7.40 (m, 7H), 7.24 (m, 2H), 7.09 (m, 1H), 6.88 (d, 1H), 4.86 (t, 2H), 4.20 (t, 2H), 2.37 (m, 2H).

Example 40A ethyl 1-(3-(naphthalen-1-yloxy)propyl)-3-(2-(trifluoromethyl)phenyl)-1H-indole-2-carboxylate This example was prepared by substituting ortho-tolylboronic acid with 2-(trifluoromethyl)phenylboronic acid in EXAMPLE 31D.

Example 40B 1-(3-(1-naphthyloxy)propyl)-3-(2-(trifluoromethyl)phenyl)-1H-indole-2-carboxylic acid This example was prepared by substituting EXAMPLE 31D with EXAMPLE 40A in EXAMPLE 31E. $^1$H NMR (400 MHz, DMSO-$d_6$) δ 12.75 (br, 1H), 8.24 (d, 1H), 7.87 (d, 1H), 7.82 (d, 1H), 7.69 (m, 2H), 7.60 (m, 1H), 7.52 (m, 3H), 7.36 (m, 2H), 7.24 (m, 1H), 7.06 (m, 2H), 6.88 (d, 1H), 4.92 (t, 2H), 4.17 (t, 2H), 2.36 (m, 2H).

Example 41A ethyl 1-(3-(naphthalen-1-yloxy)propyl)-3-(3-(trifluoromethyl)phenyl)-1H-indole-2-carboxylate This example was prepared by substituting ortho-tolylboronic acid with 3-(trifluoromethyl)phenylboronic acid in EXAMPLE 31D.

Example 41B 1-(3-(1-naphthyloxy)propyl)-3-(3-(trifluoromethyl)phenyl)-1H-indole-2-carboxylic acid This example was prepared by substituting EXAMPLE 31D with EXAMPLE 41A in EXAMPLE 31E. $^1$H NMR (400 MHz, DMSO-$d_6$) δ 13.13 (br, 1H), 8.16 (d, 1H), 7.87 (d, 1H), 7.70 (m, 5H), 7.48 (m, 3H), 7.38 (m, 2H), 7.28 (m, 1H), 7.13 (m, 1H), 6.88 (d, 1H), 4.90 (t, 2H), 4.21 (t, 2H), 2.39 (m, 2H).

Example 42A ethyl 1-(3-(naphthalen-1-yloxy)propyl)-3-(4-(trifluoromethyl)phenyl)-1H-indole-2-carboxylate This example was prepared by substituting ortho-tolylboronic acid with 4-(trifluoromethyl)phenylboronic acid in EXAMPLE 31D.

Example 42B 1-(3-(1-naphthyloxy)propyl)-3-(4-(trifluoromethyl)phenyl)-1H-indole-2-carboxylic acid This example was prepared by substituting EXAMPLE 31D with EXAMPLE 42A in EXAMPLE 31E. $^1$H NMR (400 MHz, DMSO-$d_6$) δ 13.16 (br, 1H), 8.21 (d, 1H), 7.87 (d, 1H), 7.78 (d, 2H), 7.70 (d, 1H), 7.63 (d, 2H), 7.50 (m, 4H), 7.39 (m, 1H), 7.27 (m, 1H), 7.13 (m, 1H), 6.88 (d, 1H), 4.90 (t, 2H), 4.21 (t, 2H), 2.39 (m, 2H).

Example 43A ethyl 1-(3-(naphthalen-1-yloxy)propyl)-3-(4-(trifluoromethoxy)phenyl)-1H-indole-2-carboxylate This example was prepared by substituting ortho-tolylboronic acid with 4-(trifluoromethoxyphenylboronic acid in EXAMPLE 31D.

Example 43B 1-(3-(1-naphthyloxy)propyl)-3-(4-(trifluoromethoxy)phenyl)-1H-indole-2-carboxylic acid This example was prepared by substituting EXAMPLE 31D with EXAMPLE 43A in EXAMPLE 31E. $^1$H NMR (400 MHz, DMSO-$d_6$) δ 13.09 (br, 1H), 8.22 (d, 1H), 7.87 (d, 1H), 7.70 (m, 5H), 7.53 (m, 4H), 7.43 (m, 5H), 7.26 (m, 1H), 7.13 (m, 1H), 6.88 (d, 1H), 4.88 (t, 2H), 4.21 (t, 2H), 2.38 (m, 2H).

Example 44A ethyl 3-(2,3-dimethylphenyl)-1-(3-(naphthalen-1-yloxy)propyl)-1H-indole-2-carboxylate This example was prepared by substituting ortho-tolylboronic acid with 2,3-dimethylphenylboronic acid in EXAMPLE 31D.

Example 44B 3-(2,3-dimethylphenyl)-1-(3-(1-naphthyloxy)propyl)-1H-indole-2-carboxylic acid This example was prepared by substituting EXAMPLE 31D with EXAMPLE 44A in EXAMPLE 31E. $^1$H NMR (400 MHz, DMSO-$d_6$) δ 12.67 (br, 1H), 8.24 (d, 1H), 7.87 (d, 1H), 7.66 (d, 1H), 7.53 (m, 3H), 7.38 (m, 1H), 7.23 (m, 1H), 7.15 (m, 1H), 7.10 (m, 2H), 7.03 (m, 1H), 6.99 (d, 1H), 6.88 (d, 1H), 4.90 (t, 2H), 4.19 (t, 2H), 2.38 (m, 2H), 2.29 (s, 3H), 1.93 (s, 3H).

Example 45A ethyl 3-(2,5-dimethylphenyl)-1-(3-(naphthalen-1-yloxy)propyl)-1H-indole-2-carboxylate This example was prepared by substituting ortho-tolylboronic acid with 2,5-dimethylphenylboronic acid in EXAMPLE 31D.

Example 45B 3-(2,5-dimethylphenyl)-1-(3-(1-naphthyloxy)propyl)-1H-indole-2-carboxylic acid This example was prepared by substituting EXAMPLE 31D with EXAMPLE 45A in EXAMPLE 31E. $^1$H NMR (400 MHz, DMSO-$d_6$) δ 12.69 (br, 1H), 8.19 (d, 1H), 7.87 (d, 1H), 7.66 (d, 1H), 7.49 (m, 3H), 7.38 (m, 1H), 7.23 (m, 1H), 7.15 (m, 1H), 7.07 (m, 3H), 6.93 (d, 1H), 6.88 (d, 1H), 4.90 (t, 2H), 4.19 (t, 2H), 2.38 (m, 2H), 2.27 (s, 3H), 1.96 (s, 3H).

Example 46A ethyl 3-(3,4-dimethylphenyl)-1-(3-(naphthalen-1-yloxy)propyl)-1H-indole-2-carboxylate This example was prepared by substituting ortho-tolylboronic acid with 3,4-dimethylphenylboronic acid in EXAMPLE 31D.

Example 46B 3-(3,4-dimethylphenyl)-1-(3-(1-naphthyloxy)propyl)-1H-indole-2-carboxylic acid This example was prepared by substituting EXAMPLE 31D with EXAMPLE 46A in EXAMPLE 31E. $^1$H NMR (400 MHz, DMSO-$d_6$) δ 12.89 (br, 1H), 8.22 (d, 1H), 7.87 (d, 1H), 7.64 (d, 1H), 7.45 (m, 5H), 7.22 (m, 1H), 7.17 (m, 2H), 7.07 (m, 2H), 6.88 (d, 1H), 4.84 (t, 2H), 4.19 (t, 2H), 2.36 (m, 2H), 2.27 (s, 3H), 2.25 (s, 3H).

Example 47A ethyl 3-(3,5-dimethylphenyl)-1-(3-(naphthalen-1-yloxy)propyl)-1H-indole-2-carboxylate This example was prepared by substituting ortho-tolylboronic acid with 3,5-dimethylphenylboronic acid in EXAMPLE 31D.

Example 47B 3-(3,5-dimethylphenyl)-1-(3-(1-naphthyloxy)propyl)-1H-indole-2-carboxylic acid This example was prepared by substituting EXAMPLE 31D with EXAMPLE 47A in EXAMPLE 31E. $^1$H NMR (400 MHz, DMSO-$d_6$) δ 12.92 (br, 1H), 8.19 (d, 1H), 7.87 (d, 1H), 7.64 (d, 1H), 7.48 (m, 5H), 7.23 (m, 1H), 7.08 (m, 1H), 6.97 (s, 3H), 6.87 (d, 1H), 4.84 (t, 2H), 4.19 (t, 2H), 2.36 (m, 2H), 2.31 (s, 3H).

Example 48A ethyl 3-(2,5-dimethoxyphenyl)-1-(3-(naphthalen-1-yloxy)propyl)-1H-indole-2-carboxylate This example was prepared by substituting ortho-tolylboronic acid with 2,5-dimethoxyphenylboronic acid in EXAMPLE 31D.

Example 48B 3-(2,5-dimethoxyphenyl)-1-(3-(1-naphthyloxy)propyl)-1H-indole-2-carboxylic acid This example was prepared by substituting EXAMPLE 31D with EXAMPLE 48A in EXAMPLE 31E. $^1$H NMR (400 MHz, DMSO-$d_6$) δ 12.73 (br, 1H), 8.26 (m, 1H), 7.88 (m, 1H), 7.64 (d, 1H), 7.53 (m, 3H), 7.35 (m, 2H), 7.22 (m, 1H), 7.08 (m, 1H), 6.97 (d, 1H), 6.89 (m, 2H), 6.83 (d, 1H), 4.84 (t, 2H), 4.19 (t, 2H), 3.72 (s, 3H), 3.60 (s, 3H), 2.35 (m, 2H).

Example 49A ethyl 3-(3,4-dimethoxyphenyl)-1-(3-(naphthalen-1-yloxy)propyl)-1H-indole-2-carboxylate This example was prepared by substituting ortho-tolylboronic acid with 3,4-dimethoxyphenylboronic acid in EXAMPLE 31D.

Example 49B 3-(3,4-dimethoxyphenyl)-1-(3-(1-naphthyloxy)propyl)-1H-indole-2-carboxylic acid This example was prepared by substituting EXAMPLE 31D with EXAMPLE 49A in EXAMPLE 31E. $^1$H NMR (400 MHz, DMSO-$d_6$) δ 12.95 (br, 1H), 8.23 (m, 1H), 7.88 (m, 1H), 7.64 (d, 1H), 7.50 (m, 4H), 7.38 (m, 1H), 7.23 (m, 1H), 7.08 (m, 1H), 7.02 (d, 1H), 6.97 (d, 1H), 6.94 (dd, 1H), 6.88 (d, 1H), 4.84 (t, 2H), 4.19 (t, 2H), 3.81 (s, 3H), 3.74 (s, 3H), 2.35 (m, 2H).

Example 50A 1-(4-bromobutoxy)naphthalene

This example was prepared by substituting 3-bromopropanol with 4-bromobutanol in EXAMPLE 31A.

Example 50B ethyl 3-ortho-tolyl-1H-indole-2-carboxylate

A mixture of EXAMPLE 31B (1.08 g), ortho-tolylboronic acid (1.1 g), (1,1'-bis(diphenylphosphino)ferrocene)dichloropalladium(II) (140 mg) in dimethoxyethane:2N aqueous Na$_2$CO$_3$ (25 mL:5 mL) was stirred under nitrogen at 80° C. for 16 hours, diluted with ethyl acetate and was washed with water and brine. The organic phase was dried (MgSO$_4$), filtered, and concentrated. The concentrate was purified by flash chromatography on silica gel with 0-10% ethyl acetate/hexanes.

Example 50C ethyl 1-(4-(naphthalen-1-yloxy)butyl)-3-ortho-tolyl-1H-indole-2-carboxylate This example was prepared by substituting EXAMPLE 31A with EXAMPLE 50A and substituting EXAMPLE 31B with EXAMPLE 50B in EXAMPLE 31C.

Example 50D 3-(2-methylphenyl)-1-(4-(1-naphthyloxy)butyl)-1H-indole-2-carboxylic acid This example was prepared by substituting EXAMPLE 31D with EXAMPLE 50C in EXAMPLE 31E. $^1$H NMR (400 MHz, DMSO-$d_6$) δ 12.69 (br, 1H), 8.09 (d, 1H), 7.85 (d, 1H), 7.64 (d, 1H), 7.47 (m, 3H), 7.38 (m, 1H), 7.26 (m, 4H), 7.16 (m, 1H), 7.09 (m, 2H), 6.91 (d, 1H), 4.75 (t, 2H), 4.16 (t, 2H), 2.02 (m, 5H), 1.86 (m, 2H).

Example 51A 2-(4-bromobutoxy)naphthalene

This example was prepared by substituting 3-bromopropanol with 4-bromobutanol and substituting 1-naphthol with 2-naphthol in EXAMPLE 31A.

Example 51B ethyl 1-(4-(naphthalen-2-yloxy)butyl)-3-ortho-tolyl-1H-indole-2-carboxylate This example was prepared by substituting EXAMPLE 31A with EXAMPLE 51A and substituting EXAMPLE 31B with EXAMPLE 50B in EXAMPLE 31C.

Example 51C 3-(2-methylphenyl)-1-(4-(2-naphthyloxy)butyl)-1H-indole-2-carboxylic acid This example was prepared by substituting EXAMPLE 31D with EXAMPLE 51B in EXAMPLE 31E. $^1$H NMR (400 MHz, DMSO-$d_6$) δ 12.69 (br, 1H), 7.79 (m, 3H), 7.69 (d, 1H), 7.44 (m, 1H), 7.32 (m, 5H), 7.21 (m, 1H), 7.11 (m, 4H), 4.72 (t, 2H), 4.10 (t, 2H), 2.02 (s, 3H), 1.96 (m, 2H), 1.80 (m, 2H).

Example 52A 1-(4-bromobutoxy)-2,3-dichlorobenzene

This example was prepared by substituting 3-bromopropanol with 4-bromobutanol and substituting 1-naphthol with 2,3-dichlorophenol in EXAMPLE 31A.

Example 52B ethyl 1-(4-(2,3-dichlorophenoxy)butyl)-3-ortho-tolyl-1H-indole-2-carboxylate This example was prepared by substituting EXAMPLE 31A with EXAMPLE 52A and substituting EXAMPLE 31B with EXAMPLE 50B in EXAMPLE 31C.

Example 52C 1-(4-(2,3-dichlorophenoxy)butyl)-3-(2-methylphenyl)-1H-indole-2-carboxylic acid This example was prepared by substituting EXAMPLE 31D with EXAMPLE 52B in EXAMPLE 31E. $^1$H NMR (400 MHz, DMSO-$d_6$) δ 12.66 (br, 1H), 7.67 (d, 1H), 7.34 (m, 1H), 7.26 (m, 4H), 7.18 (dd, 1H), 7.14 (m, 1H), 7.08 (m, 3H), 4.71 (t, 2H), 4.10 (t, 2H), 2.01 (s, 3H), 1.95 (m, 2H), 1.76 (m, 2H).

Example 53A ethyl 1-(2-(2,4-dichlorophenoxy)ethyl)-3-o-tolyl-1H-indole-2-carboxylate This example was prepared by substituting EXAMPLE 31A with 1-(2-bromoethoxy)-2,4-dichlorobenzene and substituting EXAMPLE 31B with EXAMPLE 50B in EXAMPLE 31C.

Example 53B 1-(2-(2,4-dichlorophenoxy)ethyl)-3-(2-methylphenyl)-1H-indole-2-carboxylic acid This example was prepared by substituting EXAMPLE 31D with EXAMPLE 53A in EXAMPLE 31E. $^1$H NMR (400 MHz, DMSO-$d_6$) δ 12.68 (br, 1H), 7.75 (d, 1H), 7.49 (d, 1H), 7.35 (m, 1H), 7.28 (m, 3H), 7.22 (m, 1H), 7.14 (m, 2H), 7.07 (d, 2H), 5.07 (t, 2H), 4.45 (t, 2H), 2.01 (s, 3H).

Example 54A ethyl 1-(3-(2,4-dichlorophenoxy)propyl)-3-ortho-tolyl-1H-indole-2-carboxylate This example was prepared by substituting EXAMPLE 31A with 1-(3-bromopropoxy)-2,4-dichlorobenzene and EXAMPLE 31B with EXAMPLE 50B in EXAMPLE 31C.

Example 54B 1-(3-(2,4-dichlorophenoxy)propyl)-3-(2-methylphenyl)-1H-indole-2-carboxylic acid This example was prepared by substituting EXAMPLE 31D with EXAMPLE 54A in EXAMPLE 31E. $^1$H NMR (400 MHz, DMSO-$d_6$) δ 12.68 (br, 1H), 7.64 (d, 1H), 7.59 (d, 1H), 7.35 (dd, 1H), 7.26 (m, 4H), 7.15 (m, 1H), 7.06 (m, 3H), 4.78 (t, 2H), 4.05 (t, 2H), 2.27 (m, 2H), 2.01 (s, 3H).

Example 55

1-(4-(2,4-dichlorophenoxy)butyl)-3-(2-methylphenyl)-1H-indole-2-carboxylic acid

Example 55A ethyl 1-(4-(2,4-dichlorophenoxy)butyl)-3-ortho-tolyl-1H-indole-2-carboxylate This example was prepared by substituting EXAMPLE 31A with 1-(4-bromobutyoxy)-2,4-dichlorobenzene and substituting EXAMPLE 31B with EXAMPLE 50B in EXAMPLE 31C.

Example 55B 1-(4-(2,4-dichlorophenoxy)butyl)-3-(2-methylphenyl)-1H-indole-2-carboxylic acid This example was prepared by substituting EXAMPLE 31D with EXAMPLE 55A in EXAMPLE 31E. $^1$H NMR (400 MHz, DMSO-$d_6$) δ 12.68 (br, 1H), 7.64 (d, 1H), 7.54 (d, 1H), 7.33 (m, 2H), 7.24 (m, 3H), 7.11 (m, 4H), 4.70 (t, 2H), 4.07 (t, 2H), 2.01 (s, 3H), 1.94 (m, 2H), 1.74 (m, 2H).

Example 56A ethyl 3-benzyl-1-(3-(naphthalen-1-yloxy)propyl)-1H-indole-2-carboxylate A mixture of EXAMPLE 31C (100 mg), 0.5M benzyl zinc(II) bromide in THF (1.32 mL) and (1,1'-bis(diphenylphosphino)ferrocene)dichloropalladium(II) (18 mg) in THF (2 mL) was stirred at 60° C. for 16 hours. The mixture was diluted with ethyl acetate, and the organic phase was washed with water and brine and dried (MgSO$_4$), filtered, and concentrated. The concentrate was purified by flash chromatography on silica gel with 0-8% ethyl acetate/hexanes.

Example 56B 3-benzyl-1-(3-(1-naphthyloxy)propyl)-1H-indole-2-carboxylic acid

This example was prepared by substituting EXAMPLE 31D with EXAMPLE 56A in EXAMPLE 31E. $^1$H NMR (400 MHz, DMSO-$d_6$) δ 13.34 (br, 1H), 8.24 (d, 1H), 7.87 (m, 1H), 7.64 (d, 1H), 7.52 (m, 3H), 7.46 (d, 1H), 7.37 (m, 1H), 7.22 (m, 5H), 7.11 (m, 1H), 7.03 (m, 1H), 6.85 (d, 1H), 4.84 (t, 2H), 4.46 (s, 2H), 4.13 (t, 2H), 2.31 (m, 2H).

Example 57A ethyl 3-(2-methylbenzyl)-1-(3-(naphthalen-1-yloxy)propyl)-1H-indole-2-carboxylate This example was prepared by substituting benzylzinc(II) bromide with (2-methylbenzyl)zinc(II) bromide in EXAMPLE 56A.

Example 57B 3-(2-methylbenzyl)-1-(3-(1-naphthyloxy)propyl)-1H-indole-2-carboxylic acid This example was prepared by substituting EXAMPLE 31D with EXAMPLE 57A in EXAMPLE 31E. $^1$H NMR (400

MHz, DMSO-d$_6$) δ 13.11 (br, 1H), 8.24 (d, 1H), 7.87 (m, 1H), 7.61 (d, 1H), 7.52 (m, 2H), 7.46 (m, 1H), 7.37 (m, 2H), 7.16 (m, 2H), 7.02 (m, 2H), 6.92 (m, 1H), 6.86 (d, 1H), 6.66 (d, 1H), 4.88 (t, 2H), 4.40 (s, 2H), 4.13 (t, 2H), 2.38 (s, 3H), 2.34 (m, 2H).

Example 58A ethyl 3-(3-methylbenzyl)-1-(3-(naphthalen-1-yloxy)propyl)-1H-indole-2-carboxylate This example was prepared by substituting benzyl zinc(II) bromide with (3-methylbenzyl)zinc(II) bromide in EXAMPLE 56A.

Example 58B 3-(3-methylbenzyl)-1-(3-(1-naphthyloxy)propyl)-1H-indole-2-carboxylic acid This example was prepared by substituting EXAMPLE 31D with EXAMPLE 58A in EXAMPLE 31E. $^1$H NMR (400 MHz, DMSO-d$_6$) δ 13.24 (br, 1H), 8.24 (d, 1H), 7.87 (m, 1H), 7.62 (d, 1H), 7.52 (m, 3H), 7.46 (m, 1H), 7.37 (m, 1H), 7.16 (m, 1H), 7.03 (m, 4H), 6.92 (d, 1H), 6.85 (d, 1H), 4.84 (t, 2H), 4.40 (s, 2H), 4.13 (t, 2H), 2.31 (m, 2H), 2.20 (s, 3H).

Example 59A ethyl 3-(4-methylbenzyl)-1-(3-(naphthalen-1-yloxy)propyl)-1H-indole-2-carboxylate This example was prepared by substituting benzylzinc(II) bromide with (4-methylbenzyl)zinc(II) bromide in EXAMPLE 56A.

Example 59B 3-(4-methylbenzyl)-1-(3-(1-naphthyloxy)propyl)-1H-indole-2-carboxylic acid This example was prepared by substituting EXAMPLE 31D with EXAMPLE 59A in EXAMPLE 31E. $^1$H NMR (400 MHz, DMSO-d$_6$) δ 13.23 (br, 1H), 8.24 (m, 1H), 7.87 (m, 1H), 7.62 (d, 1H), 7.52 (m, 3H), 7.46 (m, 1H), 7.37 (m, 1H), 7.16 (m, 1H), 7.11 (d, 1H), 7.01 (m, 3H), 6.85 (d, 1H), 4.84 (t, 2H), 4.41 (s, 2H), 4.13 (t, 2H), 2.31 (m, 2H), 2.20 (s, 3H).

Example 60A ethyl 1-(3-(naphthalen-1-yloxy)propyl)-3-(naphthalen-2-ylmethyl)-1H-indole-2-carboxylate This example was prepared by substituting benzylzinc(II) bromide with (naphthalen-2-ylmethyl)zinc(II) bromide in EXAMPLE 56A.

Example 60B 3-(2-naphthylmethyl)-1-(3-(1-naphthyloxy)propyl)-1H-indole-2-carboxylic acid This example was prepared by substituting EXAMPLE 31D with EXAMPLE 60A in EXAMPLE 31E. $^1$H NMR (400 MHz, DMSO-d$_6$) δ 13.30 (br, 1H), 8.25 (m, 1H), 7.87 (m, 1H), 7.80 (m, 1H), 7.74 (m, 3H), 7.67 (d, 1H), 7.59 (d, 1H), 7.52 (m, 2H), 7.41 (m, 5H), 7.18 (m, 1H), 7.02 (m 1H), 6.85 (d, 1H), 4.86 (t, 2H), 4.64 (s, 2H), 4.14 (t, 2H), 2.33 (m, 2H).

Example 61

1-(3-(1-naphthyloxy)propyl)-3-(2-phenylethyl)-1H-indole-2-carboxylic acid

A mixture of EXAMPLE 66 (18 mg), cyclohexene (0.5 mL), Pd/C (10%, 5 mg) in ethanol (2 mL) was heated under microwave conditions (CEM Discover) at 110° C. for 20 minutes, filtered and concentrated. The product was purified by preparative reverse phase HPLC (Zorbax SB, C-18, 20% to 100% acetonitrile/water/0.1% trifluoroacetic acid). $^1$H NMR (400 MHz, DMSO-d$_6$) δ 13.15 (br, 1H), 8.23 (m, 1H), 7.87 (m, 1H), 7.68 (m, 1H), 7.53 (m, 3H), 7.45 (d, 1H), 7.37 (m, 1H), 7.26 (m, 4H), 7.18 (m, 2H), 7.06 (m 1H), 6.85 (d, 1H), 4.83 (t, 2H), 4.12 (t, 2H), 3.30 (t, 2H), 2.83 (t, 2H), 2.33 (m, 2H).

Example 62

1-(3-(1-naphthyloxy)propyl)-3-(3-phenylpropyl)-1H-indole-2-carboxylic acid

This example was prepared by substituting EXAMPLE 66 with EXAMPLE 67 in EXAMPLE 61. $^1$H NMR (400 MHz, DMSO-d$_6$) δ 13.07 (br, 1H), 8.23 (d, 1H), 7.87 (m, 1H), 7.59 (d, 1H), 7.55 (m, 3H), 7.44 (m, 1H), 7.35 (m, 1H), 7.26 (m, 2H), 7.18 (m, 4H), 7.06 (m 1H), 6.82 (d, 1H), 4.83 (t, 2H), 4.12 (t, 2H), 3.08 (t, 2H), 2.65 (t, 2H), 2.29 (m, 2H), 1.88 (m, 2H).

Example 63A 1-(2-bromoethoxy)naphthalene

This example was prepared by substituting 3-bromopropanol with 2-bromoethanol in EXAMPLE 31A.

Example 63B ethyl 1-(2-(naphthalen-1-yloxy)ethyl)-3-ortho-tolyl-1H-indole-2-carboxylate This example was prepared by substituting EXAMPLE 31A with EXAMPLE 63A and substituting EXAMPLE 31B with EXAMPLE 50B in EXAMPLE 31C.

Example 63C 3-(2-methylphenyl)-1-(2-(1-naphthyloxy)ethyl)-1H-indole-2-carboxylic acid This example was prepared by substituting EXAMPLE 31D with EXAMPLE 63B in EXAMPLE 31. $^1$H NMR (400 MHz, DMSO-d$_6$) δ 12.82 (br, 1H), 7.88 (m, 2H), 7.79 (d, 1H), 7.43 (m, 3H), 7.33 (m, 4H), 7.21 (m, 1H), 7.12 (m, 3H), 6.94 (d, 1H), 5.22 (m, 2H), 4.50 (m, 2H), 1.95 (s, 3H).

Example 64A 2-(2-bromoethoxy)naphthalene

This example was prepared by substituting 1-naphthol with 2-naphthol and substituting 3-bromopropanol with 2-bromoethanol in EXAMPLE 31A.

Example 64B ethyl 1-(2-(naphthalen-2-yloxy)ethyl)-3-ortho-tolyl-1H-indole-2-carboxylate This example was prepared by substituting EXAMPLE 31A with EXAMPLE 64A and substituting EXAMPLE 31B with EXAMPLE 50B in EXAMPLE 31C.

Example 64C 3-(2-methylphenyl)-1-(2-(2-naphthyloxy)ethyl)-1H-indole-2-carboxylic acid This example was prepared by substituting EXAMPLE 31D with EXAMPLE 64B in EXAMPLE 31. $^1$H NMR (400 MHz, DMSO-$d_6$) δ 12.77 (br, 1H), 7.78 (m, 4H), 7.43 (m, 1H), 7.37 (m, 1H), 7.29 (m, 4H), 7.21 (m, 1H), 7.14 (m 1H), 7.09 (m, 2H), 7.02 (dd, 1H), 5.08 (m, 2H), 4.45 (m, 2H), 1.99 (s, 3H).

Example 65A 1-(2-bromoethoxy)-2,3-dichlorobenzene

This example was prepared by substituting 1-naphthol with 2,3-dichlorophenol and substituting 3-bromopropanol with 2-bromoethanol in EXAMPLE 31A.

Example 65B ethyl 1-(2-(2,3-dichlorophenoxy)ethyl)-3-ortho-tolyl-1H-indole-2-carboxylate This example was prepared by substituting EXAMPLE 31A with EXAMPLE 65A and substituting EXAMPLE 31B with EXAMPLE 50B in EXAMPLE 31C.

Example 65C 1-(2-(2,3-dichlorophenoxy)ethyl)-3-(2-methylphenyl)-1H-indole-2-carboxylic acid This example was prepared by substituting EXAMPLE 31D with EXAMPLE 65B in EXAMPLE 31. $^1$H NMR (400 MHz, DMSO-$d_6$) δ 12.68 (br, 1H), 7.75 (d, 1H), 7.35 (m, 1H), 7.24 (m, 4H), 7.13 (m 3H), 7.09 (d, 2H), 5.08 (m, 2H), 4.48 (m, 2H), 2.01 (s, 3H).

Example 66

1-(3-(1-naphthyloxy)propyl)-3-((E)-2-phenylvinyl)-1H-indole-2-carboxylic acid

A mixture of EXAMPLE 31C (100 mg), (E)-styrylboronic acid (39 mg), and bis(triphenylphosphine)palladium(II) dichloride (8 mg) in 7:3:3 dimethoxyethane:ethanol: 1N aqueous LiOH (2 mL) was heated under microwave conditions (CEM Discover) at 130° C. for 30 minutes The mixture was quenched with 1 NHCl and extracted with ethyl acetate. The extract was dried ($Na_2SO_4$), filtered, and concentrated. The concentrate was purified by reverse phase HPLC (Zorbax SB-C18, 20-100% acetonitrile/water/0.1% trifluoroacetic acid) to afford the title compound. $^1$H NMR (400 MHz, DMSO-$d_6$) δ 13.59 (br, 1H), 8.24 (m, 1H), 8.15 (d, 1H), 7.94 (m, 1H), 7.87 (m, 1H), 7.69 (d, 1H), 7.59 (m, 2H), 7.53 (m, 2H), 7.46 (m, 1H), 7.40 (m, 3H), 7.28 (m, 3H), 7.21 (m 1H), 6.87 (d, 1H), 4.87 (t, 2H), 4.17 (t, 2H), 2.34 (m, 2H).

Example 67

1-(3-(1-naphthyloxy)propyl)-3-((1E)-3-phenylprop-1-enyl)-1H-indole-2-carboxylic acid This example was prepared by substituting (E)-styrylboronic acid with (E)-3-phenylprop-1-enylboronic acid in EXAMPLE 66. $^1$H NMR (400 MHz, DMSO-$d_6$) δ 13.37 (br, 1H), 8.22 (d, 1H), 7.87 (m, 2H), 7.61 (d, 1H), 7.51 (m, 2H), 7.45 (m, 1H), 7.35 (m, 5H), 7.20 (m, 3H), 7.10 (m, 1H), 6.85 (d, 1H), 6.45 (m, 1H), 4.81 (t, 2H), 4.13 (t, 2H), 3.59 (d, 2H), 2.30 (m, 2H).

Example 68

3-((E)-2-cyclohexylvinyl)-1-(3-(1-naphthyloxy)propyl)-1H-indole-2-carboxylic acid This example was prepared by substituting (E)-styrylboronic acid with (E)-2-cyclohexylvinylboronic acid in EXAMPLE 66. $^1$H NMR (400 MHz, DMSO-$d_6$) δ 13.30 (br, 1H), 8.23 (m, 1H), 7.91 (d, 1H), 7.87 (m, 1H), 7.60 (d, 1H), 7.52 (m, 2H), 7.45 (d, 1H), 7.37 (t, 1H), 7.21 (t, 1H), 7.12 (t, 1H), 7.07 (dd, 1H), 6.85 (d, 1H), 6.25 (dd, 1H), 4.81 (t, 2H), 4.13 (t, 2H), 2.29 (m, 2H), 2.17 (m, 1H), 1.81 (m, 2H), 1.75 (m, 2H), 1.65 (m, 1H), 1.33 (m, 2H), 1.22 (m, 3H).

Example 69

1-(3-(1-naphthyloxy)propyl)-3-(3-(piperidin-1-ylcarbonyl)phenyl)-1H-indole-2-carboxylic acid This example was prepared by substituting (E)-styrylboronic acid with 3-(piperidine-1-carbonyl)phenylboronic acid in EXAMPLE 66. $^1$H NMR (400 MHz, DMSO-$d_6$) δ 13.04 (br, 1H), 8.19 (d, 1H), 7.86 (d, 1H), 7.68 (d, 1H), 7.44 (m, 9H), 7.26 (t, 1H), 7.11 (t, 1H), 6.88 (d, 1H), 4.88 (t, 2H), 4.20 (t, 2H), 3.57 (br, 4H), 2.38 (m, 2H), 1.61 (br, 2H), 1.50 (br, 4H).

Example 70

3-(4-fluoro-3-(morpholin-4-ylcarbonyl)phenyl)-1-(3-(1-naphthyloxy)propyl)-1H-indole-2-carboxylic acid This example was prepared by substituting (E)-styrylboronic acid with 4-fluoro-3-(morpholine-4-carbonyl)phenylboronic acid in EXAMPLE 66. $^1$H NMR (400 MHz, DMSO-$d_6$) δ 13.06 (br, 1H), 8.18 (d, 1H), 7.86 (m, 1H), 7.69 (d, 1H), 7.45 (m, 8H), 7.27 (m, 1H), 7.12 (t, 1H), 6.88 (d, 1H), 4.89 (t, 2H), 4.20 (t, 2H), 3.66 (s, 4H), 3.56 (br, 2H), 3.31 (br, 2H), 2.38 (m, 2H).

Example 71

3-(3-(((2-methoxyethyl)amino)carbonyl)phenyl)-1-(3-(1-naphthyloxy)propyl)-1H-indole-2-carboxylic acid This example was prepared by substituting (E)-styrylboronic acid with 3-(2-methoxyethylcarbamoyl)phenylboronic acid in EXAMPLE 66. $^1$H NMR (400 MHz, DMSO-$d_6$) δ 13.01 (br, 1H), 8.52 (t, 1H), 8.25 (m, 1H), 7.93 (s, 1H), 7.86

(m, 2H), 7.68 (d, 1H), 7.49 (m, 6H), 7.25 (m, 1H), 7.11 (t, 1H), 6.89 (d, 1H), 4.89 (t, 2H), 4.20 (t, 2H), 3.46 (m, 4H), 3.26 (s, 3H), 2.38 (m, 2H).

Example 72

3-(3-((dimethylamino)sulfonyl)phenyl)-1-(3-(1-naphthyloxy)propyl)-1H-indole-2-carboxylic acid This example was prepared by substituting (E)-styrylboronic acid with 3-(N,N-dimethylsulfamoyl)phenylboronic acid in EXAMPLE 66. $^1$H NMR (400 MHz, DMSO-$d_6$) δ 13.20 (br, 1H), 8.20 (m, 1H), 7.87 (m, 1H), 7.73 (m, 5H), 7.47 (m, 5H), 7.28 (m, 1H), 7.17 (m, 1H), 6.87 (m, 1H), 4.89 (m, 2H), 4.18 (m, 2H), 2.66 (s, 6H), 2.40 (m, 2H).

Example 73

3-(3-(morpholin-4-ylmethyl)phenyl)-1-(3-(1-naphthyloxy)propyl)-1H-indole-2-carboxylic acid This example was prepared by substituting (E)-styrylboronic acid with 4-(3-(4,4,5,5-tetramethyl-1,3,2-dioxaborolan-2-yl)benzyl)morpholine in EXAMPLE 66. $^1$H NMR (400 MHz, DMSO-$d_6$) δ 10.01 (br, 1H), 8.24 (m, 1H), 7.88 (m, 1H), 7.70 (d, 1H), 7.53 (m, 8H), 7.39 (t, 1H), 7.28 (m, 1H), 7.13 (t, 1H), 6.89 (d, 1H), 4.90 (t, 2H), 4.42 (s, 2H), 4.20 (t, 2H), 3.98 (br, 2H), 3.65 (br, 2H), 3.29 (br, 2H), 3.14 (br, 2H), 2.38 (m, 2H).

Example 74A ethyl 1-(3-(naphthalen-1-yloxy)propyl)-3-(piperidin-1-yl)-1H-indole-2-carboxylate A mixture of EXAMPLE 31C (100 mg), piperidine (57 mg), tris(dibenzylideneacetone)dipalladium(0) (20 mg), 2,2'-bis(diphenylphosphino)-1,1'-binaphthyl (26 mg) and $Cs_2CO_3$ (216 mg) in toluene (2 mL) was heated at 100° C. for 48 hours. The mixture was diluted with ethyl acetate and was washed with water and brine. The organic phase was dried ($Na_2SO_4$) filtered, and concentrated. The concentrate was purified by flash chromatography on silica gel with 0-10% ethyl acetate/hexanes.

Example 74B 1-(3-(1-naphthyloxy)propyl)-3-piperidin-1-yl-1H-indole-2-carboxylic acid A mixture of EXAMPLE 74A (30 mg) in 1N aqueous LiOH/methanol/THF (1 mL/1 mL/1 mL) was stirred at room temperature overnight. The reaction mixture was acidified with 1 NHCl (1 mL), and extracted with ethyl acetate. The organic phase was dried ($Na_2SO_4$) filtered, and concentrated. The concentrate was purified by reverse phase HPLC (Zorbax SB-C18, 20-100% acetonitrile/water/0.1% trifluoroacetic acid). $^1$H NMR (400 MHz, DMSO-$d_6$) δ 16.82 (s, 1H), 8.08 (d, 1H), 7.96 (d, 1H), 7.85 (d, 1H), 7.69 (d, 1H), 7.48 (m, 3H), 7.36 (t, 1H), 7.24 (m, 1H), 7.13 (t, 1H), 6.83 (t, 1H), 4.89 (t, 2H), 4.16 (t, 2H), 3.24 (br, 4H), 2.33 (m, 2H), 1.70 (br, 6H).

Example 75A ethyl 3-morpholino-1-(3-(naphthalen-1-yloxy)propyl)-1H-indole-2-carboxylate This example was prepared by substituting piperidine with morpholine in EXAMPLE 74A.

Example 75B 3-morpholin-4-yl-1-(3-(1-naphthyloxy)propyl)-1H-indole-2-carboxylic acid This example was prepared by substituting EXAMPLE 74A with EXAMPLE 75A in EXAMPLE 74B. $^1$H NMR (400 MHz, DMSO-$d_6$) δ 15.74 (s, 1H), 8.10 (d, 1H), 7.93 (d, 1H), 7.85 (m, 1H), 7.71 (d, 1H), 7.50 (m, 2H), 7.44 (d, 1H), 7.36 (t, 1H), 7.25 (m, 1H), 7.14 (m, 1H), 6.84 (d, 1H), 4.89 (t, 2H), 4.16 (t, 2H), 3.81 (t, 4H), 3.26 (t, 4H), 2.33 (m, 2H).

Example 76A ethyl 1-(3-(naphthalen-1-yloxy)propyl)-3-(3-(trifluoromethoxy)phenylamino)-1H-indole-2-carboxylate This example was prepared by substituting piperidine with 3-(trifluoromethoxy)aniline in EXAMPLE 74A.

Example 76B 1-(3-(1-naphthyloxy)propyl)-3-((3-(trifluoromethoxy)phenyl)amino)-1H-indole-2-carboxylic acid This example was prepared by substituting EXAMPLE 74A with EXAMPLE 76A in EXAMPLE 74B. $^1$H NMR (400 MHz, DMSO-$d_6$) δ 13.23 (br, 1H), 8.24 (m, 1H), 8.08 (br, 1H), 7.87 (m, 1H), 7.64 (d, 1H), 7.52 (m, 2H), 7.46 (d, 2H), 7.37 (t, 1H), 7.28 (d, 1H), 7.20 (m, 2H), 7.00 (t, 1H), 6.85 (d, 1H), 6.74 (m, 2H), 6.63 (d, 1H), 4.85 (t, 2H), 4.15 (t, 2H), 2.32 (m, 2H).

Example 77A ethyl 3-(4-(methoxycarbonyl)piperidin-1-yl)-1-(3-(naphthalen-1-yloxy)propyl)-1H-indole-2-carboxylate This example was prepared by replacing piperidine with methyl piperidine-4-carboxylate in EXAMPLE 74A.

Example 77B 3-(4-carboxypiperidin-1-yl)-1-(3-(1-naphthyloxy)propyl)-1H-indole-2-carboxylic acid This example was prepared by replacing EXAMPLE 74A with EXAMPLE 77A in EXAMPLE 74B. $^1$H NMR (400 MHz, DMSO-$d_6$) δ 16.42 (s, 1H), 12.39 (s, 1H), 8.08 (d, 1H), 7.94 (d, 1H), 7.85 (m, 1H), 7.70 (d, 1H), 7.48 (m, 3H), 7.36 (t, 1H), 7.25 (m, 1H), 7.13 (t, 1H), 6.83 (d, 1H), 4.89 (t, 2H), 4.15 (t, 2H), 3.42 (m, 2H), 3.13 (m, 2H), 2.69 (m, 1H), 2.33 (m, 2H), 2.05 (m, 2H), 1.72 (m, 2H).

Example 79

3-anilino-4-(2-methylphenyl)-1-(3-(1-naphthyloxy)propyl)-1H-indole-2-carboxylic acid Example 79A methyl 1-(3-(naphthalen-1-yloxy)propyl)-3-(phenylamino)-4-o-tolyl-1H-indole-2-carboxylate A mixture of EXAMPLE 126C (42 mg, 0.079 mmol), aniline (8.71 μl, 0.095 mmol), xantphos (4.14 mg, 7.15 μmol), diacetoxypalladium (1.071 mg, 4.77 μmol) and dioxane (2 ml) was heated at 160° C. under microwave condition for 30 min. The precipitate was filtered off and the filtrate concentrated. The residue was purified by flash chromatography, eluting with 1/1 dichloromethane/hexane to provide the desired product.

Example 79B 3-anilino-4-(2-methylphenyl)-1-(3-(1-naphthyloxy) propyl)-1H-indole-2-carboxylic acid A mixture EXAMPLE 79A (34.1 mg) and sodium hydroxide (0.252 ml) in tetrahydrofuran (1 ml) and methanol (1.000 ml) was stirred overnight and acidified with HCl. The resulting mixture was concentrated and the residue purified by RPHPLC (mobile phase: 10%-100% acetonitrile in 0.1% TFA aqueous solution during 60 min) on a C18 column. $^1$H NMR (400 MHz, dimethyl sulfoxide-$D_6$) δ 13.11 (s, 1H), 8.21-8.31 (m, 1H), 7.86-7.90 (m, 1H), 7.65 (d, J=7.98 Hz, 1H), 7.49-7.57 (m, 2H), 7.44-7.49 (m, 1H), 7.36-7.42 (m, 1H), 7.26 (dd, J=8.29, 7.06 Hz, 1H), 6.92-7.00 (m, 1H), 6.80-6.91 (m, 4H), 6.70-6.78 (m, 3H), 6.63 (s, 1H), 6.46 (t, J=7.21 Hz, 1H), 6.06 (d, J=7.67 Hz, 2H), 4.75-5.07 (m, 2H), 4.20 (t, J=5.68 Hz, 2H), 2.39 (t, J=6.14 Hz, 2H), 1.87 (s, 3H).

Example 80

3-(3-(1-naphthylthio)cyclohexyl)-1H-indole-2-carboxylic acid

Example 80A ethyl 3-(3-oxocyclohexyl)-1H-indole-2-carboxylate

Ethyl 1H-indole-2-carboxylate (2.953 g) and cyclohex-2-enone (1.004 mL) were added to acetonitrile (50 mL). Bismuth (III) trifluoromethanesulfonate (341 mg) was added, and the solution was heated at 65° C. for two days. The solution was cooled, concentrated, and purified by flash column chromatography on silica gel with 10% increasing to 20% ethyl acetate in hexanes to provide the title compound.

Example 80B ethyl 3-(3-hydroxycyclohexyl)-1H-indole-2-carboxylate

EXAMPLE 80A (931 mg) was added to methanol (20 mL), cooled to 0° C., and treated with sodium borohydride (247 mg). The solution was mixed at 0° C. for one hour, quenched with 1 MHCl, and extracted with 70% ethyl acetate (in hexanes). The solution was dried with brine and anhydrous sodium sulfate. After filtration, the solvent was removed under vacuum to provide the title compound.

Example 80C ethyl 3-(3-(naphthalen-1-ylthio)cyclohexyl)-1H-indole-2-carboxylate 1,1'-(azodicarbonyl)-dipiperidine (188 mg) was added to tetrahydrofuran (5 mL), cooled to 0° C., and treated with trimethylphosphine (1M in toluene, 0.746 mL). The solution was mixed at 0° C. for 15 minutes. Naphthalene-1-thiol (120 mg) was added followed by EXAMPLE 80B (195 mg). The solution was allowed to warm to ambient temperature and mix overnight. The solution was concentrated and purified by flash column chromatography on silica gel with 10% ethyl acetate in hexanes to provide the title compound.

Example 80D 3-(3-(1-naphthylthio)cyclohexyl)-1H-indole-2-carboxylic acid

EXAMPLE 80C (64 mg) was dissolved in tetrahydrofuran (1 mL), water (0.33 mL), and methanol (0.33 mL). Lithium hydroxide monohydrate (31 mg) was added, and the solution was mixed at ambient temperature overnight. The solution was made slightly acidic using 1 MHCl, extracted with ethyl acetate, and dried with anhydrous sodium sulfate. After filtration, the solvent was removed under vacuum to provide the title compound. $^1$H NMR (300 MHz, dimethyl sulfoxide-$d_6$) δ 12.95 (broad s, 1H), 11.35 (s, 1H), 8.52 (d, 1H), 7.94 (dd, 1H), 7.84 (dd, 1H), 7.81 (d, 1H), 7.64-7.52 (m, 3H), 7.46 (dd, 1H), 7.38 (d, 1H), 7.17 (td, 1H), 6.97 (td, 1H), 4.33 (m, 1H), 3.85 (broad s, 1H), 2.07-1.86 (m, 5H), 1.83-1.65 (m, 3H).

Example 81

3-(3-(1-naphthyloxy)cyclohexyl)-1H-indole-2-carboxylic acid

Example 81A ethyl 3-(3-(naphthalen-1-yloxy)cyclohexyl)-1H-indole-2-carboxylate

The title compound was prepared by substituting diethyl azodicarboxylate, triphenylphosphine, and naphthalene-1-ol for 1,1'-(azodicarbonyl)-dipiperidine, trimethylphosphine, and naphthalene-1-thiol, respectively, in EXAMPLE 80C.

Example 81B 3-(3-(1-naphthyloxy)cyclohexyl)-1H-indole-2-carboxylic acid

The title compound was prepared by substituting EXAMPLE 81A for EXAMPLE 80C in EXAMPLE 80D. $^1$H NMR (300 MHz, dimethyl sulfoxide-$d_6$) δ 12.94 (broad s, 1H), 11.34 (s, 1H), 8.47 (m, 1H), 7.89-7.83 (m, 2H), 7.54 (t, 2H), 7.46-7.36 (m, 3H), 7.20 (t, 1H), 7.00 (m, 2H), 5.06 (broad s, 1H), 4.54 (tt, 1H), 2.44 (td, 1H), 2.21-2.08 (m, 4H), 1.83-1.75 (m, 3H).

Example 88

1-(2-methylbenzyl)-3-(3-(1-naphthyloxy)propyl)-1H-indole-2-carboxylic acid $^1$H NMR (300 MHz, dimethyl sulfoxide-$d_6$) δ 13.06 (s, 1H), 8.18-8.25 (m, 1H), 7.84-7.90 (m, 1H), 7.78 (d, J=7.80 Hz, 1H), 7.48-7.55 (m, 2H), 7.43-7.48 (m, 1H), 7.34-7.41 (m, 2H), 7.24 (t, J=7.63 Hz, 1H), 7.18 (d, J=7.46 Hz, 1H), 6.99-7.09 (m, 2H), 6.87 (t, J=7.46 Hz, 2H), 5.92 (d, J=7.46 Hz, 1H), 5.78 (s, 2H), 4.20 (t, J=6.10 Hz, 2H), 3.39 (t, J=7.5 Hz, 2H), 2.40 (s, 3H), 2.20-2.29 (m, J=1.70 Hz, 2H).

Example 89

1-(2-(dimethylamino)ethyl)-3-(3-(1-naphthyloxy) propyl)-1H-indole-2-carboxylic acid $^1$H NMR (300 MHz, dimethyl sulfoxide-$d_6$) δ 13.04 (bs, 1H), 8.18-8.25 (m, 1H), 7.81-7.91 (m, 1H), 7.68 (d, J=7.9 Hz, 1H), 7.48-7.58 (m, 3H), 7.45 (d, J=7.9 Hz, 1H), 7.34-7.42 (m, 1H), 7.27 (t, J=7.7 Hz, 1H), 7.00 (t, J=7.5 Hz, 1H), 6.88 (d, J=6.3 Hz, 1H), 4.79 (s, 1H), 4.56 (t, J=5.9 Hz, 2H), 4.17 (t, J=6.1 Hz, 2H), 3.66 (t, J=5.8 Hz, 2H), 2.10-2.25 (m, 2H).

Example 90

1-(3-methylbenzyl)-3-(3-(1-naphthyloxy)propyl)-1H-indole-2-carboxylic acid $^1$H NMR (300 MHz, dimethyl sulfoxide-$d_6$) δ 13.17 (s, 1H), 8.14-8.28 (m, 1H), 7.79-7.93 (m, 1H), 7.74 (d, J=7.8 Hz, 1H), 7.42-7.57 (m, 3H), 7.34-7.40 (m, 1H), 7.26 (t, J=7.6 Hz, 1H), 7.10 (t, J=7.5 Hz, 1H), 6.96-7.06 (m, 2H), 6.83-6.91 (m, 2H), 6.71 (d, J=7.5 Hz, 1H), 5.79 (s, 2H), 4.17 (t, J=6.1 Hz, 2H), 3.33-3.41 (m, 2H), 2.24 (s, 2H), 2.19 (s, 3H).

Example 91

1-(4-methylbenzyl)-3-(3-(1-naphthyloxy)propyl)-1H-indole-2-carboxylic acid $^1$H NMR (300 MHz, dimethyl sulfoxide-$d_6$) δ 13.14 (s, 1H), 8.10-8.28 (m, 1H), 7.79-7.95 (m, 1H), 7.73 (d, J=7.9 Hz, 1H), 7.41-7.57 (m, 4H), 7.33-7.41 (m, 1H), 7.25 (t, J=7.5 Hz, 1H), 7.02 (t, J=7.7 Hz, 4H), 6.88 (t, J=7.9 Hz, 4H), 5.77 (s, 2H), 4.17 (t, J=6.1 Hz, 2H), 3.32-3.39 (m, 2H), 2.21-2.25 (m, 2H), 2.20 (s, 3H).

Example 92

1-(1,1'-biphenyl-2-ylmethyl)-3-(3-(1-naphthyloxy)propyl)-1H-indole-2-carboxylic acid $^1$H NMR (300 MHz, dimethyl sulfoxide-$d_6$) δ 13.04 (s, 1H), 8.09-8.25 (m, 1H), 7.81-7.90 (m, 1H), 7.76 (d, J=8.1 Hz, 1H), 7.41-7.56 (m, 8H), 7.33-7.41 (m, 1H), 7.18-7.31 (m, 4H), 6.99-7.13 (m, 2H), 6.87 (d, J=6.8 Hz, 1H), 6.17 (d, J=7.8 Hz, 1H), 5.71 (s, 2H), 4.18 (t, J=6.1 Hz, 2H), 3.33-3.41 (m, 2H), 2.15-2.28 (m, 2H).

Example 93

1-(1,1'-biphenyl-3-ylmethyl)-3-(3-(1-naphthyloxy)propyl)-1H-indole-2-carboxylic acid $^1$H NMR (300 MHz, dimethyl sulfoxide-$d_6$) δ 13.12 (s, 1H), 8.11-8.34 (m, 1H), 7.80-7.92 (m, 1H), 7.74 (d, J=8.1 Hz, 1H), 7.20-7.61 (m, 15H), 7.02 (t, J=7.5 Hz, 1H), 6.94 (d, J=7.5 Hz, 1H), 6.85 (d, J=6.8 Hz, 1H), 5.91 (s, 2H), 4.18 (t, J=6.1 Hz, 2H), 3.31-3.46 (m, 2H), 2.12-2.34 (m, 2H).

Example 94

1-(1,1'-biphenyl-4-ylmethyl)-3-(3-(1-naphthyloxy)propyl)-1H-indole-2-carboxylic acid $^1$H NMR (300 MHz, dimethyl sulfoxide-$d_6$) δ 13.20 (s, 1H), 8.13-8.30 (m, 1H), 7.80-7.94 (m, 1H), 7.68-7.81 (m, 1H), 7.22-7.60 (m, 14H), 6.95-7.13 (m, 3H), 6.88 (d, J=6.4 Hz, 1H), 5.88 (s, 2H), 4.19 (t, J=6.1 Hz, 2H), 3.38 (t, J=7.5 Hz, 2H), 2.15-2.32 (m, 2H).

Example 95

1-(2,4-dimethylbenzyl)-3-(3-(1-naphthyloxy)propyl)-1H-indole-2-carboxylic acid $^1$H NMR (300 MHz, dimethyl sulfoxide-$d_6$) δ 13.03 (s, 1H), 8.18-8.29 (m, 1H), 7.81-7.93 (m, 1H), 7.77 (d, J=7.8 Hz, 1H), 7.31-7.60 (m, 5H), 7.17-7.29 (m, 1H), 6.94-7.09 (m, 2H), 6.88 (d, J=6.4 Hz, 1H), 6.66 (d, J=7.8 Hz, 1H), 5.84 (d, J=7.8 Hz, 1H), 5.73 (s, 2H), 4.19 (t, J=6.1 Hz, 2H), 3.38 (t, J=7.5 Hz, 2H), 2.35 (s, 3H), 2.18-2.32 (m, 2H), 2.16 (s, 3H).

Example 96

1-(4-carboxybenzyl)-3-(3-(1-naphthyloxy)propyl)-1H-indole-2-carboxylic acid $^1$H NMR (300 MHz, dimethyl sulfoxide-$d_6$) δ 13.04 (s, 1H), 12.93 (s, 1H), 8.06-8.30 (m, 1H), 7.69-7.94 (m, 4H), 7.43-7.58 (m, 4H), 7.33-7.41 (m, 1H), 7.27 (t, J=7.1 Hz, 1H), 6.97-7.12 (m, 3H), 6.88 (d, J=6.8 Hz, 1H), 5.89 (s, 2H), 4.18 (t, J=5.9 Hz, 2H), 3.34-3.44 (m, 2H), 2.13-2.32 (m, 2H).

Example 97

1-((2S)-2-methyl-3-(1-naphthyloxy)propyl)-4-(2-methylphenyl)-1H-indole-2-carboxylic acid $^1$H NMR (300 MHz, dimethyl sulfoxide-$d_6$) δ 12.91 (s, 1H), 8.06-8.31 (m, 1H), 7.77-7.95 (m, 1H), 7.64 (d, J=8.7 Hz, 1H), 7.42-7.59 (m, 3H), 7.18-7.43 (m, 5H), 6.97 (d, J=6.7 Hz, 1H), 6.71-6.89 (m, 2H), 4.82-4.95 (m, 1H), 4.66-4.83 (m, 1H), 3.97-4.13 (m, 2H), 2.59-2.78 (m, 1H), 1.98-2.15 (m, 3H), 1.07 (d, J=6.7 Hz, 3H).

Example 98

1-((2R)-2-methyl-3-(1-naphthyloxy)propyl)-4-(2-methylphenyl)-1H-indole-2-carboxylic acid $^1$H NMR (300 MHz, dimethyl sulfoxide-$d_6$) δ 12.91 (s, 1H), 8.06-8.31 (m, 1H), 7.77-7.95 (m, 1H), 7.64 (d, J=8.7 Hz, 1H), 7.42-7.59 (m, 3H), 7.18-7.43 (m, 5H), 6.97 (d, J=6.7 Hz, 1H), 6.71-6.89 (m, 2H), 4.82-4.95 (m, 1H), 4.66-4.83 (m, 1H), 3.97-4.13 (m, 2H), 2.59-2.78 (m, 1H), 1.98-2.15 (m, 3H), 1.07 (d, J=6.7 Hz, 3H).

Example 99

3-(3-(1-naphthyloxy)propyl)-1-(pyridin-4-ylmethyl)-1H-indole-2-carboxylic acid $^1$H NMR (500 MHz, dimethyl sulfoxide-$d_6$) δ 13.30 (br. s, 1H) 8.61-8.69 (m, 2H) 8.19 (d, 1H) 7.78-7.90 (m, 2H) 7.26-7.57 (m, 8H) 7.10 (t, 1H) 6.89 (d, 1H) 6.02 (s, 2H) 4.21 (t, 2H) 3.40 (t, 2H) 2.21-2.29 (m, 2H).

Example 100

3-(3-(1-naphthyloxy)propyl)-1-(pyridin-2-ylmethyl)-1H-indole-2-carboxylic acid $^1$H NMR (500 MHz, dimethyl sulfoxide-$d_6$) δ 8.51-8.57 (m, 1H) 8.17-8.23 (m, 1H) 7.84-7.89 (m, 1H) 7.71-7.79 (m, 2H) 7.42-7.57 (m, 4H) 7.38 (t, 1H) 7.24-7.35 (m, 2H) 7.06 (t, 1H) 6.89 (d, 1H) 6.77 (d, 1H) 5.91 (s, 2H) 4.19 (t, 2H) 3.38 (t, 2H) 2.19-2.30 (m, 2H).

Example 101

1-(4-methoxybenzyl)-3-(2-(1-naphthyloxy)ethoxy)-1H-indole-2-carboxylic acid

Example 101A ethyl 3-bromo-1H-indole-2-carboxylate

To a stirred solution of ethyl 1H-indole-2-carboxylate (9.45 g) in tetrahydrofuran (100 mL) was added N-bromosuccinimide (8.89 g, 50 mmol). The mixture was stirred at room temperature for 1 hour. The mixture was concentrated under vacuum and the residue was dissolved with water (100 ml) and diethyl ether (300 ml). The organic layer was washed with water brine and dried over $Na_2SO_4$. After filtration, concentration of solvent afforded the title compound.

Example 101B ethyl 3-bromo-1-(4-methoxybenzyl)-1H-indole-2-carboxylate

To a solution of EXAMPLE 101A (5.9 g) in N,N-dimethylformamide (50 mL) was added 1-(bromomethyl)-4-methoxybenzene (4.85 g) and $Cs_2CO_3$ (25 g). The mixture was stirred overnight at room temperature. The mixture was diluted with ether (300 mL) and water (200 mL). The aqueous layer was extracted with ether twice. The combined extracts were washed with water (×3), brine and dried over $Na_2SO_4$. Concentration of the solvent gave EXAMPLE 101B.

Example 101C ethyl 1-(4-methoxybenzyl)-3-(2-(naphthalen-1-yloxy)ethoxy)-1H-indole-2-carboxylate To a solution of EXAMPLE 101B (388 mg) and 2-(naphthalen-1-yloxy)ethanol (188 mg) in toluene (3 ml) was added 1,1'-binaphthyl-2-yldi-tert-butylphosphine (7.5 mg), palladium(II) acetate (5 mg) and $Cs_2CO_3$ (488 mg). The mixture was purged with argon and stirred at room temperature and then heated at 80° C. overnight. After this time the mixture was diluted with ethyl acetate (200 mL) and washed with water, brine and dried over $Na_2SO_4$. After concentration of the solvent, the residue was loaded on a silica gel column and eluted with 5% ethyl acetate in hexane to give EXAMPLE 101C.

Example 101D 1-(4-methoxybenzyl)-3-(2-(1-naphthyloxy)ethoxy)-1H-indole-2-carboxylic acid To a solution of EXAMPLE 101C (80 mg) in tetrahydrofuran (2 ml), methanol (1 ml) and water (1 ml) was added LiOH (100 mg). The mixture was stirred at room temperature overnight. The mixture was then acidified with 5% HCl and extracted with ethyl acetate (200 ml). The organic layer was washed with water, brine and dried over $Na_2SO_4$. After concentration of the solvent, the residue was dissolved in DMSO/methanol (1:1, 1.5 ml) and purified via reverse phase HPLC. $^1$H NMR (500 MHz, dimethyl sulfoxide-$d_6$) δ 12.99 (m, 1H), 8.01 (m, 1H), 7.86 (m, 1H), 7.73 (m, 1H), 7.46 (m, 6H), 7.27 (m, 1H), 6.98 (m, 3H), 6.74 (m, 2H), 5.70 (s, 2H), 4.64 (m, 2H), 4.48 (m, 2H), 3.67 (s, 3H).

Example 102

1-(4-methoxybenzyl)-3-(3-(1-naphthyloxy)prop-1-ynyl)-1H-indole-2-carboxylic acid

Example 102A ethyl 1-(4-methoxybenzyl)-3-(3-(naphthalen-1-yloxy)prop-1-ynyl)-1H-indole-2-carboxylate To a solution of EXAMPLE 101B (3.89 g) in acetonitrile (20 ml) was added $Pd(PhCN)_2Cl_2$ (38 mg), dicyclohexyl(2',4',6'-triisopropylbiphenyl-2-yl)phosphine (143 mg), and $Cs_2CO_3$ (3.91 g). The mixture was purged with argon and stirred at room temperature for 25 minutes. After this time, 1-(prop-2-ynyloxy)naphthalene (2.2 g) was added to the mixture which was purged with argon again. The mixture was then stirred at 80° C. for 3 hours. The mixture was diluted with ethyl acetate (300 ml) and washed with water, brine and dried over $Na_2SO_4$. After filtration, the solvent was concentrated and the residue was loaded on a silica gel column and eluted with 5% ethyl acetate in hexane to give EXAMPLE 102A.

Example 102B 1-(4-methoxybenzyl)-3-(3-(1-naphthyloxy)prop-1-ynyl)-1H-indole-2-carboxylic acid The title compound was prepared via ester hydrolysis as detailed in the procedure for EXAMPLE 110D, substituting EXAMPLE 102A for EXAMPLE 101C. $^1$H NMR (300 MHz, dimethyl sulfoxide-$d_6$) δ 13.57 (m, 1H), 8.20 (m, 1H), 7.90 (m, 1H), 7.57 (m, 6H), 7.25 (m, 3H), 6.98 (d, 2H), 6.80 (d, 2H), 5.78 (s, 2H), 5.36 (s, 2H), 3.66 (s, 3H).

Example 103

4-(2-methylphenyl)-1-(3-(1-naphthyloxy)propyl)-1H-indole-2-carboxylic acid $^1$H NMR (300 MHz, dimethyl sulfoxide-$d_6$) δ 12.92 (m, 1H), 8.26 (m, 1H), 7.87 (m, 1H), 7.65 (m, 1H), 7.38 (m, 9H), 6.98 (m, 1H), 6.89 (m, 1H), 6.78 (s, 1H), 4.91 (m, 2H), 4.19 (m, 2H), 2.37 (m, 2H), 2.09 (s, 3H).

Example 104

4-(2,6-dimethylphenyl)-1-(3-(1-naphthyloxy)propyl)-1H-indole-2-carboxylic acid $^1$H NMR (300 MHz, dimethyl sulfoxide-$d_6$) δ 12.89 (m, 1H), 8.28 (m, 1H), 7.87 (m, 1H), 7.37 (m, 9H), 6.86 (m, 2H), 6.58 (m, 1H), 4.91 (t, 2H), 4.17 (t, 2H), 2.38 (m, 2H), 1.87 (s, 6H).

Example 105

1-(3-(1-naphthyloxy)propyl)-4-(1,3,5-trimethyl-1H-pyrazol-4-yl)-1H-indole-2-carboxylic acid $^1$H NMR (300 MHz, dimethyl sulfoxide-$d_6$) δ 8.25 (m, 1H), 7.88 (m, 1H), 7.41 (m, 6H), 6.91 (m, 4H), 4.89 (m, 2H), 4.20 (m, 2H), 3.76 (s, 3H), 2.35 (m, 2H), 2.10 (s, 3H), 2.01 (s, 3H).

Example 106

1-(3-(1-naphthyloxy)propyl)-4-(2-oxocyclohexyl)-1H-indole-2-carboxylic acid

Example 106A ethyl 4-bromo-1H-indole-2-carboxylate

To a solution of ethyl bromoacetate (42 g) in ethanol (120 mL) was added a solution of NaN$_3$ (25 g) in water (60 ml). The mixture was stirred at reflux for 4 hours. The mixture was concentrated under vacuum and the residue was partitioned between ether (300 mL) and water (200 mL). The aqueous layer was further extracted with ether. The combined extracts were washed with water (×3), brine and dried over Na$_2$SO$_4$. After filtration, careful concentration of solvent gave ethyl azidoacetate (26 g) which was dissolved in ethanol (100 ml) and 2-bromobenzaldehyde (12.5 g) was added to the solution which was then added dropwise to a cooled (−15° C.) solution of sodium ethoxide (prepared from Na (5.2 g) and ethanol (60 ml)). The mixture was stirred at 0° C. for 4 hours before poured into a mixture of ice and saturated aqueous NH$_4$Cl solution. The mixture was filtered and the precipitate was washed with water and dissolved in ethyl acetate and dried over Na$_2$SO$_4$. Concentration of solvent gave crude intermediate, which was dissolved in xylene (100 ml) and added dropwise to refluxing xylene under nitrogen. After the addition, the mixture was stirred at reflux overnight. Concentration of the mixture under vacuum gave the crude product, which was purified by silica gel chromatography (2% ethyl acetate in hexane).

Example 106B ethyl 4-bromo-1-(3-(naphthalen-1-yloxy)propyl)-1H-indole-2-carboxylate To a solution of EXAMPLE 106A (5.5 g) in N,N-dimethylformamide (60 mL) was added 1-(3-bromopropoxy)naphthalene (5.4 g) and Cs$_2$CO$_3$ (22 g). The mixture was stirred overnight at room temperature. The mixture was diluted with ether (300 mL) and water (200 mL). The aqueous layer was extracted with ether twice. The combined extracts were washed with water (×3), brine and dried over Na$_2$SO$_4$. Concentration of the mixture gave crude product, which was purified by flash chromatography (2% ethyl acetate in hexane).

Example 106C ethyl 1-(3-(naphthalen-1-yloxy)propyl)-4-(2-oxocyclohexyl)-1H-indole-2-carboxylate To a solution of EXAMPLE 106B (438 mg) and cyclohexanone (196 mg) in dioxane (3 ml) was added tris(dibenzylideneacetone)dipalladium(0) (5 mg), 4,5-bis(diphenylphosphino)-9,9-dimethylxanthene (Xantphos, 7 mg) and Cs$_2$CO$_3$ (652 mg). The mixture was stirred at 80° C. under nitrogen overnight. After cooling, the reaction mixture was diluted with ethyl acetate and shaken with water. The product was extracted with ether (200 ml×3). The combined organic extracts were washed with water, brine, and dried over Na$_2$SO$_4$. After filtration, concentration of the mixture and flash column purification (3% ethyl acetate in hexane) provided EXAMPLE 106C.

Example 106D 1-(3-(1-naphthyloxy)propyl)-4-(2-oxocyclohexyl)-1H-indole-2-carboxylic acid The title compound was prepared via ester hydrolysis as detailed in the procedure for EXAMPLE 101D, substituting EXAMPLE 106C for EXAMPLE 101C. $^1$H NMR (300 MHz, dimethyl sulfoxide-d$_6$) δ 12.86 (m, 1H), 8.28 (m, 1H), 7.87 (m, 1H), 7.46 (m, 5H), 7.17 (m, 2H), 6.89 (m, 2H), 4.87 (m, 2H), 4.17 (m, 3H), 2.70 (m, 1H), 2.04 (m, 9H).

Example 107

4-(2-methylphenyl)-3-(morpholin-4-ylmethyl)-1-(3-(1-naphthyloxy)propyl)-1H-indole-2-carboxylic acid

Example 107A methyl 4-bromo-3-formyl-1H-indole-2-carboxylate

To a solution of methyl 4-bromo-1H-indole-2-carboxylate (4.09 g) in dichloromethane (60 mL) was added a mixture of POCl$_3$ (3.7 g) and N,N-dimethylformamide (1.76 g). The mixture was stirred at reflux overnight. The mixture was diluted with ethyl acetate (300 mL) and 2M sodium acetate solution in water (200 mL). The mixture was stirred thoroughly for 1 hour. The aqueous layer was extracted with ethyl acetate. The combined extracts were washed with water (×3), brine and dried over Na$_2$SO$_4$. After filtration, concentration of the mixture gave the title compound, which was used in next step without purification.

Example 107B methyl 4-bromo-3-formyl-1-(3-(naphthalen-1-yloxy)propyl)-1H-indole-2-carboxylate To a solution of EXAMPLE 107A (1.76 g) in N,N-dimethylformamide (10 mL) was added 1-(3-bromopropoxy)naphthalene (1.66 g) and Cs$_2$CO$_3$ (6.10 g). The mixture was stirred for 3 days at room temperature. The mixture was diluted with ethyl acetate (300 mL) and water (200 mL). The aqueous layer was extracted with ethyl acetate. The combined organic extracts were washed with water (×3) and brine and dried over Na$_2$SO$_4$. After filtration, concentration of solvent gave crude product, which was purified by column chromatography (5% ethyl acetate in hexane).

Example 107C methyl 3-formyl-1-(3-(naphthalen-1-yloxy)propyl)-4-o-tolyl-1H-indole-2-carboxylate To a mixture of EXAMPLE 107B (0.5 g) and o-tolylboronic acid (175 mg) in tetrahydrofuran (5 ml) was added tris(dibenzylideneacetone)dipalladium(0) (25 mg), tri-t-butyl-phosphonium tetrafluoroborate (16 mg) and CsF (489 mg). The mixture was purged with Argon and stirred at room temperature for 24 hours. The mixture was diluted with ethyl acetate (200 mL) and washed with water and brine and dried over Na₂SO₄. After filtration, concentration of the solvent and column purification (5% ethyl acetate in hexane) provided EXAMPLE 107C.

Example 107D 4-(2-methylphenyl)-3-(morpholin-4-ylmethyl)-1-(3-(1-naphthyloxy)propyl)-1H-indole-2-carboxylic acid To a solution of EXAMPLE 107C (50 mg) in dichloroethane (3 ml) was added sodium triacetoxyborohydride (35 mg) and morpholine (15 mg). The mixture was stirred overnight at room temperature. The reaction mixture was diluted with ethyl acetate (200 ml) and washed with water, brine, and dried over Na₂SO₄. The residue was dissolved in tetrahydrofuran (4 ml), methanol (2 mL) and water (2 ml) and LiOH (100 mg) was added. The mixture was stirred at room temperature overnight. The mixture was concentrated and the residue neutralized with aqueous NH₄Cl and extracted with ethyl acetate (100 mL×3). The combined extracts were dried and concentrated to give crude product, which was purified by RPHPLC. $^1$H NMR (300 MHz, dimethyl sulfoxide-d₆) δ 8.25 (m, 1H), 7.86 (m, 2H), 7.45 (m, 9H), 6.93 (m, 2H), 4.99 (m, 2H), 4.47 (m, 1H), 4.25 (t, 2H), 3.60 (m, 10H), 2.43 (m, 2H), 1.92 (s, 3H).

Example 108

4-(2-methylphenyl)-1-(3-(1-naphthyloxy)propyl)-3-(pyrrolidin-1-ylmethyl)-1H-indole-2-carboxylic acid $^1$H NMR (300 MHz, dimethyl sulfoxide-d₆) δ 8.84 (m, 1H), 8.24 (m, 1H), 7.86 (m, 2H), 7.48 (m, 9H), 6.95 (m, 2H), 4.99 (m, 2H), 4.47 (m, 1H), 4.26 (m, 2H), 2.77 (m, 2H), 2.42 (m, 2H), 1.92 (s, 3H), 1.61 (m, 4H).

Example 109

3-((dimethylamino)methyl)-4-(2-methylphenyl)-1-(3-(1-naphthyloxy)propyl)-1H-indole-2-carboxylic acid $^1$H NMR (300 MHz, dimethyl sulfoxide-d₆) δ 8.58 (m, 1H), 8.27 (m, 1H), 7.84 (m, 2H), 7.44 (m, 9H), 6.93 (m, 2H), 5.00 (m, 2H), 4.37 (m, 1H), 4.24 (m, 2H), 2.40 (m, 6H), 2.15 (m, 3H), 1.92 (s, 3H).

Example 110

3-(((cyclohexylmethyl)amino)methyl)-4-(2-methylphenyl)-1-(3-(1-naphthyloxy)propyl)-1H-indole-2-carboxylic acid $^1$H NMR (300 MHz, dimethyl sulfoxide-d₆) δ 8.35 (m, 2H), 7.90 (m, 1H), 7.77 (m, 1H), 7.43 (m, 9H), 6.93 (m, 2H), 4.95 (m, 2H), 4.22 (m, 3H), 3.17 (m, 2H), 2.36 (m, 2H), 2.20 (m, 1H), 2.06 (m, 1H), 1.91 (m, 3H), 1.56 (m, 4H), 1.18 (m, 3H), 0.76 (m, 2H).

Example 111

4-(2-morpholin-4-ylcyclohexyl)-1-(3-(1-naphthyloxy)propyl)-1H-indole-2-carboxylic acid $^1$H NMR (300 MHz, dimethyl sulfoxide-d₆) δ 9.69 (m, 1H), 8.24 (m, 1H), 7.88 (m, 1H), 7.49 (m, 7H), 7.21 (m, 1H), 6.86 (m, 1H), 4.88 (m, 2H), 4.18 (m, 3H), 4.04 (m, 2H), 3.82 (m, 4H), 2.91 (m, 4H), 2.27 (m, 3H), 1.92 (m, 3H), 1.49 (m, 3H).

Example 112

4-(2-methylphenyl)-3-((4-methylpiperazin-1-yl)methyl)-1-(3-(1-naphthyloxy)propyl)-1H-indole-2-carboxylic acid $^1$H NMR (300 MHz, dimethyl sulfoxide-d₆) δ 8.25 (m, 1H), 7.88 (m, 1H), 7.73 (m, 1H), 7.40 (m, 8H), 6.90 (m, 2H), 6.65 (m, 1H), 4.90 (m, 2H), 4.23 (m, 3H), 3.36 (m, 4H), 2.85 (m, 3H), 2.67 (s, 3H), 2.37 (m, 3H), 1.95 (s, 3H).

Example 113

4-(2-methylphenyl)-1-(3-(1-naphthyloxy)propyl)-3-(piperidin-1-ylmethyl)-1H-indole-2-carboxylic acid $^1$H NMR (300 MHz, dimethyl sulfoxide-d₆) δ 8.26 (m, 1H), 7.86 (m, 2H), 7.45 (m, 10H), 6.93 (m, 2H), 4.97 (m, 2H), 4.46 (m, 1H), 4.25 (m, 2H), 3.72 (m, 2H), 3.10 (m, 3H), 2.40 (m, 2H), 1.92 (s, 3H), 1.35 (m, 6H).

Example 114

4-(2-methylphenyl)-3-((4-methylpiperidin-1-yl)methyl)-1-(3-(1-naphthyloxy)propyl)-1H-indole-2-carboxylic acid $^1$H NMR (300 MHz, dimethyl sulfoxide-d₆) δ 8.27 (m, 1H), 7.86 (m, 2H), 7.44 (m, 8H), 6.95 (m, 2H), 4.98 (m, 2H), 4.44 (m, 1H), 4.24 (m, 2H), 3.70 (m, 2H), 3.18 (m, 2H), 2.40 (m, 2H), 1.91 (s, 3H), 1.36 (m, 8H), 0.79 (m, 3H).

Example 115

3-((benzyl(methyl)amino)methyl)-4-(2-methylphenyl)-1-(3-(1-naphthyloxy)propyl)-1H-indole-2-carboxylic acid $^1$H NMR (300 MHz, dimethyl sulfoxide-d₆) δ 8.23 (m, 1H), 7.83 (m, 2H), 7.45 (m, 10H), 7.19 (m, 5H), 6.91 (m, 2H), 5.01 (m, 2H), 4.24 (m, 2H), 2.37 (m, 3H), 1.95 (m, 2H).

Example 116

4-(2-methylphenyl)-3-((methyl(pyridin-2-ylmethyl)amino)methyl)-1-(3-(1-naphthyloxy)propyl)-1H-indole-2-carboxylic acid $^1$H NMR (300 MHz, dimethyl sulfoxide-d₆) δ 8.57 (m, 1H), 8.23 (m, 1H), 7.84 (m, 3H), 7.47 (m, 8H), 7.24 (m, 4H), 6.91 (m, 2H), 4.94 (m, 2H), 4.24 (m, 2H), 4.12 (m, 2H), 2.37 (m, 4H), 2.12 (s, 3H), 1.88 (s, 3H).

Example 117

4-(2-methylphenyl)-3-((methyl(pyridin-3-ylmethyl)amino)methyl)-1-(3-(1-naphthyloxy)propyl)-1H-indole-2-carboxylic acid $^1$H NMR (300 MHz, dimethyl sulfoxide-d₆) δ 9.32 (m, 1H), 8.78 (m, 1H), 8.69 (m, 1H), 8.25 (m, 1H), 8.01 (m, 1H), 7.89 (m, 1H), 7.80 (m, 1H), 7.66 (m, 1H), 7.43 (m, 6H), 7.20

(m, 4H), 6.93 (m, 2H), 4.98 (m, 2H), 4.28 (m, 2H), 2.39 (m, 2H), 2.00 (s, 3H), 1.86 (s, 3H).

Example 118

4-(2-methylphenyl)-3-((methyl(pyridin-4-ylmethyl)amino)methyl)-1-(3-(1-naphthyloxy)propyl)-1H-indole-2-carboxylic acid $^1$H NMR (300 MHz, dimethyl sulfoxide-$d_6$) δ 8.76 (m, 2H), 8.23 (m, 1H), 7.82 (m, 2H), 7.48 (m, 7H), 7.21 (m, 4H), 6.90 (m, 2H), 4.96 (m, 2H), 4.25 (m, 2H), 2.39 (m, 2H), 2.02 (s, 3H), 1.87 (s, 3H).

Example 119

4-(2-(4-fluorophenyl)cyclohex-1-en-1-yl)-1-(3-(1-naphthyloxy)propyl)-1H-indole-2-carboxylic acid $^1$H NMR (300 MHz, chloroform-d) δ 8.36 (m, 1H), 7.81 (m, 1H), 7.52 (m, 2H), 7.42 (m, 1H), 7.32 (m, 2H), 7.20 (m, 1H), 6.96 (m, 3H), 6.65 (m, 4H), 4.81 (m, 2H), 4.06 (m, 2H), 2.51 (m, 4H), 2.38 (m, 2H), 1.89 (m, 4H).

Example 120

4-(2-methyl-6-nitrophenyl)-1-(3-(1-naphthyloxy)propyl)-1H-indole-2-carboxylic acid $^1$H NMR (300 MHz, chloroform-d) δ 8.39 (m, 1H), 7.80 (m, 2H), 7.49 (m, 7H), 7.29 (m, 1H), 7.03 (s, 1H), 6.92 (m, 1H), 6.72 (m, 1H), 4.92 (m, 2H), 4.15 (m, 2H), 2.50 (m, 2H), 2.07 (s, 3H).

Example 121

4-(2-chloro-6-methylphenyl)-1-(3-(1-naphthyloxy)propyl)-1H-indole-2-carboxylic acid $^1$H NMR (300 MHz, dimethyl sulfoxide-$d_6$) δ 8.28 (m, 1H), 7.88 (m, 1H), 7.65 (m, 1H), 7.40 (m, 8H), 6.89 (m, 2H), 6.63 (s, 1H), 4.90 (m, 2H), 4.20 (m, 2H), 2.38 (m, 2H), 1.94 (s, 3H).

Example 122

1-(3-(1-naphthyloxy)propyl)-4-(2-(4-nitrophenyl)cyclohex-1-en-1-yl)-1H-indole-2-carboxylic acid $^1$H NMR (300 MHz, chloroform-d) δ 8.37 (m, 1H), 7.81 (m, 3H), 7.52 (m, 2H), 7.32 (m, 5H), 7.10 (m, 2H), 6.99 (m, 1H), 6.68 (m, 2H), 4.84 (m, 2H), 4.06 (m, 2H), 2.54 (m, 4H), 2.42 (m, 2H), 1.93 (m, 4H).

Example 123

4-(2-(3-methoxyphenyl)cyclohex-1-en-1-yl)-1-(3-(1-naphthyloxy)propyl)-1H-indole-2-carboxylic acid $^1$H NMR (300 MHz, chloroform-d) δ 8.36 (m, 1H), 7.80 (m, 1H), 7.51 (m, 2H), 7.30 (m, 4H), 7.02 (m, 1H), 6.89 (m, 1H), 6.65 (m, 3H), 6.48 (m, 2H), 4.81 (m, 2H), 4.06 (m, 2H), 3.42 (s, 3H), 2.52 (m, 4H), 2.40 (m, 2H), 1.92 (m, 4H).

Example 124

4-(5-fluoro-2-methyl-3-((methylsulfonyl)methyl)phenyl)-1-(3-(1-naphthyloxy)propyl)-1H-indole-2-carboxylic acid $^1$H NMR (300 MHz, chloroform-d) δ 8.36 (m, 1H), 7.81 (m, 1H), 7.48 (m, 4H), 7.32 (m, 2H), 7.18 (m, 1H), 7.08 (m, 2H), 6.99 (m, 1H), 6.72 (m, 1H), 4.92 (m, 2H), 4.41 (m, 2H), 4.16 (m, 2H), 2.92 (s, 3H), 2.51 (m, 2H), 2.17 (s, 3H).

Example 125

4-(2-methylphenyl)-1-(3-(1-naphthyloxy)propyl)-3-phenyl-1H-indole-2-carboxylic acid A mixture of EXAMPLE 126A (36 mg), phenylboronic acid (12.5 mg), $K_2CO_3$ (1 M, 0.17 ml) and bis(triphenylphosphine)palladium(II) dichloride (7.2 mg) in a mixture of 1,2-dimethoxyethane (2.2 ml), ethanol (0.6 ml) and water (0.9 ml) was heated at 160° C. in a microwave reactor (CEM Discover) for 10 minutes. The reaction mixture was acidified with a diluted trifluoroacetic acid methanol solution (3:1) and concentrated. The residue was suspended in a mixture of dimethyl sulfoxide and methanol (1:1) and filtered. The filtrate was purified by RPHPLC (mobile phase: 10%-100% acetonitrile in 0.1% TFA aqueous solution during 60 min) on a C18 column to provide the desired product. $^1$H NMR (500 MHz, dimethyl sulfoxide-$d_6$) δ 8.26-8.31 (m, 1H), 7.82-7.94 (m, 1H), 7.69 (d, J=7.93 Hz, 1H), 7.50-7.58 (m, 2H), 7.46-7.49 (m, 1H), 7.41 (t, J=7.93 Hz, 1H), 7.30 (dd, J=8.39, 7.17 Hz, 1H), 6.87-6.94 (m, 3H), 6.78-6.87 (m, 7H), 6.72 (d, J=7.63 Hz, 1H), 4.76-5.00 (m, 2H), 4.25 (t, J=5.80 Hz, 2H), 2.38-2.45 (m, 2H), 1.73 (s, 3H).

Example 126

3-bromo-4-(2-methylphenyl)-1-(3-(1-naphthyloxy)propyl)-1H-indole-2-carboxylic acid

Example 126A methyl 4-o-tolyl-1H-indole-2-carboxylate

A mixture of 4-bromo-1H-indole (1.5 g) and o-tolylboronic acid (1.135 g) in dioxane (20 ml) was added tri-(t-butyl)phosphonium tetrafluoroborate (0.101 g), tris(dibenzylideneacetone)dipalladium(0) (0.159 g) and CsF (3.17 g). The reaction mixture was immediately purged with nitrogen, and 2 ml of methanol was added. The resulting mixture was stirred at room temperature for 3 hours and concentrated. The residue was purified by flash chromatography, eluting with dichloromethane to provide the desired product.

Example 126B methyl 3-bromo-4-o-tolyl-1H-indole-2-carboxylate

To a solution of EXAMPLE 126A (205 mg) in dichloromethane (5 ml) and tetrahydrofuran (5 ml) at 0° C. was added dropwise N-bromosuccinimide (144 mg) in tetrahydrofuran (3 ml). The mixture was stirred while the ice bath slowly reached room temperature. The reaction mixture was concentrated and the residue was dissolved in dichloromethane and purified by flash chromatography, eluting with 0-100% dichloromethane in hexane to provide the desired product.

Example 126C methyl 3-bromo-1-(3-(naphthalen-1-yloxy)propyl)-4-o-tolyl-1H-indole-2-carboxylate To a solution of EXAMPLE 126B (1.14 g) and 1-(3-bromopropoxy)naphthalene (0.922 g) in N,N-dimethylformamide (20 ml) was added cesium carbonate (2.158 g). The reaction was stirred at room temperature overnight and diluted with ethyl acetate and washed with water. The organic layer was dried over sodium sulfate, filtered and concentrated. The residue was purified by flash chromatography, eluting with 0-50% dichloromethane in hexane to provide the title product.

Example 126D 3-bromo-4-(2-methylphenyl)-1-(3-(1-naphthyloxy)propyl)-1H-indole-2-carboxylic acid A mixture of EXAMPLE 126C (22 mg), NaOH (0.167 ml), methanol (1.5 ml) and tetrahydrofuran (1.500 ml) was stirred at room temperature for 36 hours, acidified with HCl and concentrated. The residue was purified by RPHPLC (mobile phase: 10%-100% acetonitrile in 0.1% TFA aqueous solution during 60 minutes) on a C18 column to provide the title compound. $^1$H NMR (500 MHz, dichloromethane-$d_2$) δ 8.30-8.40 (m, 1H), 7.79-7.85 (m, 1H), 7.56 (d, J=8.54 Hz, 1H), 7.47-7.55 (m, 2H), 7.43 (d, J=8.24 Hz, 1H), 7.35 (t, J=7.93 Hz, 1H), 7.28-7.33 (m, 2H), 7.20-7.27 (m, 2H), 7.13-7.18 (m, 1H), 6.93 (d, J=7.02 Hz, 1H), 6.75 (d, J=7.63 Hz, 1H), 4.78-5.03 (m, 2H), 4.16 (t, J=5.65 Hz, 2H), 2.37-2.54 (m, 2H), 2.01 (s, 3H).

Example 128

4-(2-methylphenyl)-3-((4-methylphenyl)amino)-1-(3-(1-naphthyloxy)propyl)-1H-indole-2-carboxylic acid $^1$H NMR (500 MHz, dimethyl sulfoxide-$d_6$) δ 13.20 (s, 1H), 8.21-8.32 (m, 1H), 7.84-7.92 (m, 1H), 7.63 (d, J=8.54 Hz, 1H), 7.50-7.58 (m, 2H), 7.47 (d, J=8.54 Hz, 1H), 7.39 (t, J=7.93 Hz, 1H), 7.19-7.29 (m, 1H), 6.94-7.03 (m, 1H), 6.82-6.92 (m, 4H), 6.72 (d, J=7.02 Hz, 1H), 6.50-6.62 (m, 3H), 5.98 (d, J=8.54 Hz, 2H), 4.66-5.08 (m, 2H), 4.19 (t, J=5.80 Hz, 2H), 2.31-2.42 (m, 2H), 2.06 (s, 3H), 1.86 (s, 3H).

Example 129

3-(4-hydroxyphenyl)-4-(2-methylphenyl)-1-(3-(1-naphthyloxy)propyl)-1H-indole-2-carboxylic acid $^1$H NMR (500 MHz, dimethyl sulfoxide-$d_6$) δ 12.71 (s, 1H), 8.91 (s, 1H), 8.24-8.37 (m, 1H), 7.86-7.92 (m, 1H), 7.66 (d, J=8.24 Hz, 1H), 7.50-7.60 (m, 2H), 7.44-7.50 (m, 1H), 7.40 (t, J=7.93 Hz, 1H), 7.27 (dd, J=8.54, 7.02 Hz, 1H), 6.81-7.01 (m, 4H), 6.77 (d, J=7.32 Hz, 2H), 6.59 (d, J=7.63 Hz, 2H), 6.22 (d, J=8.24 Hz, 2H), 4.61-5.08 (m, 2H), 4.24 (t, J=5.80 Hz, 2H), 2.27-2.44 (m, 2H), 1.73 (s, 3H).

Example 130

3-(3-hydroxyphenyl)-4-(2-methylphenyl)-1-(3-(1-naphthyloxy)propyl)-1H-indole-2-carboxylic acid $^1$H NMR (500 MHz, dimethyl sulfoxide-$d_6$) δ 12.79 (s, 1H), 8.79 (s, 1H), 8.14-8.47 (m, 1H), 7.83-7.92 (m, 1H), 7.67 (d, J=8.24 Hz, 1H), 7.51-7.59 (m, 2H), 7.45-7.50 (m, 1H), 7.41 (t, J=7.93 Hz, 1H), 7.28 (dd, J=8.24, 7.02 Hz, 1H), 6.89-6.95 (m, 2H), 6.75-6.87 (m, 4H), 6.53-6.61 (m, 1H), 6.27-6.33 (m, 2H), 6.18 (d, J=7.32 Hz, 1H), 4.67-5.03 (m, 2H), 4.24 (t, J=5.80 Hz, 2H), 2.28-2.42 (m, 2H), 1.79 (s, 3H).

Example 131

4-(2-methylphenyl)-1-(3-(1-naphthyloxy)propyl)-3-pyridin-4-yl-1H-indole-2-carboxylic acid $^1$H NMR (500 MHz, dimethyl sulfoxide-$d_6$) δ 13.49 (s, br, 2H), 8.30 (d, J=6.10 Hz, 2H), 8.25 (d, J=7.93 Hz, 1H), 7.88 (d, J=7.63 Hz, 1H), 7.82 (d, J=8.54 Hz, 1H), 7.45-7.58 (m, 3H), 7.37-7.44 (m, 2H), 7.34 (d, J=5.19 Hz, 2H), 6.97-7.04 (m, 1H), 6.84-6.97 (m, 4H), 6.80 (d, J=7.63 Hz, 1H), 4.82-5.09 (m, 2H), 4.28 (t, J=5.65 Hz, 2H), 2.39-2.48 (m, 2H), 1.77 (s, 3H).

Example 132

4-(2-methylphenyl)-1-(3-(1-naphthyloxy)propyl)-3-pyridin-3-yl-1H-indole-2-carboxylic acid $^1$H NMR (500 MHz, dimethyl sulfoxide-$d_6$) δ 13.27 (s, 1H), 8.41 (d, J=5.19 Hz, 2H), 8.21-8.32 (m, 1H), 7.78-7.92 (m, 3H), 7.50-7.59 (m, 2H), 7.47-7.50 (m, 1H), 7.37-7.44 (m, 3H), 6.95-7.02 (m, 1H), 6.88-6.95 (m, 4H), 6.80 (d, J=7.63 Hz, 1H), 4.83-5.19 (m, 2H), 4.28 (t, J=5.80 Hz, 2H), 2.40-2.48 (m, 2H), 1.75 (s, 3H), J=5.80 Hz, 2H), 2.41-2.48 (m, 2H), 1.75 (s, 1H).

Example 133

3-cyano-4-(2-methylphenyl)-1-(3-(1-naphthyloxy)propyl)-1H-indole-2-carboxylic acid

Example 133A methyl 3-cyano-1-(3-(naphthalen-1-yloxy)propyl)-4-o-tolyl-1H-indole-2-carboxylate A mixture of EXAMPLE 126C (100 mg), dicyanozine (222 mg) and Pd(PPh$_3$)$_4$ (21.87 mg, 0.019 mmol) in N,N-dimethylformamide (4 ml) was heated at 180° C. for 400 seconds in a microwave reactor (CEM Discover) and then concentrated. The residue was dissolved in dichloromethane and purified by flash chromatography, eluting with 50%-100% dichloromethane in hexane to provide the desired product.

Example 133B 3-cyano-4-(2-methylphenyl)-1-(3-(1-naphthyloxy)propyl)-1H-indole-2-carboxylic acid A mixture of EXAMPLE 133A (16 mg) and sodium hydroxide (200 μl) in tetrahydrofuran (0.5 ml) and methanol (0.5 ml) was stirred overnight, neutralized with diluted HCl, and concentrated. The residue was purified by RPHPLC to provide the desired product. $^1$H NMR (500 MHz, dimethyl sulfoxide-d$_6$) δ 14.24 (s, 1H), 8.14 (d, J=8.54 Hz, 1H), 7.86 (dd, J=7.48, 5.65 Hz, 2H), 7.35-7.61 (m, 5H), 7.18-7.36 (m, 3H), 7.12 (d, J=7.32 Hz, 1H), 7.06 (d, J=7.02 Hz, 1H), 6.89 (d, J=7.32 Hz, 1H), 4.77-5.18 (m, 2H), 4.24 (t, J=5.03 Hz, 2H), 2.30-2.47 (m, 2H), 1.99 (s, 3H).

Example 134

3-bromo-5-fluoro-1-(3-(1-naphthyloxy)propyl)-1H-indole-2-carboxylic acid

Example 134A ethyl 3-bromo-5-fluoro-1H-indole-2-carboxylate

The title compound was prepared by substituting EXAMPLE 126A with ethyl 5-fluoro-1H-indole-2-carboxylate in EXAMPLE 126B.

Example 134B

To a solution of EXAMPLE 134A (465 mg) and 1-(3-bromopropoxy)naphthalene (431 mg) in N,N-dimethylformamide (10 ml) was added cesium carbonate (1059 mg). The reaction was stirred at room temperature overnight and diluted with ethyl acetate, and washed with water. The organic layer was dried over sodium sulfate, filtered, and concentrated. The residue was purified by RPHPLC to provide ethyl 3-bromo-5-fluoro-1-(3-(naphthalen-1-yloxy)propyl)-1H-indole-2-carboxylate. This ester was hydrolyzed with aqueous NaOH in tetrahydrofuran and methanol to provide the title compound. $^1$H NMR (400 MHz, dimethyl sulfoxide-D$_6$) δ 8.13 (d, J=7.98 Hz, 1H), 7.85 (d, J=7.67 Hz, 1H), 7.74 (dd, J=9.21, 4.30 Hz, 1H), 7.42-7.58 (m, 3H), 7.37 (t, J=7.98 Hz, 1H), 7.27 (dd, J=8.90, 2.45 Hz, 1H), 7.10-7.20 (m, 1H), 6.85 (d, J=7.36 Hz, 1H), 4.87 (t, J=6.90 Hz, 2H), 4.14 (t, J=5.83 Hz, 2H), 2.21-2.39 (m, 2H).

Example 135

5-(benzyloxy)-1-(3-(1-naphthyloxy)propyl)-3-(2-(trifluoromethyl)phenyl)-1H-indole-2-carboxylic acid Example 135A ethyl 5-(benzyloxy)-3-bromo-1H-indole-2-carboxylate The title compound was prepared by substituting EXAMPLE 126A with ethyl 5-(benzyloxy)-1H-indole-2-carboxylate in EXAMPLE 126B.

Example 135B ethyl 5-(benzyloxy)-3-bromo-1-(3-(naphthalen-1-yloxy)propyl)-1H-indole-2-carboxylate To a solution of EXAMPLE 135A (500 mg) and 1-(3-bromopropoxy)naphthalene (354 mg) in N,N-dimethylformamide (10 ml) was added Cs$_2$CO$_3$ (871 mg). The reaction was stirred at room temperature overnight, diluted with ethyl acetate and washed with water. The organic layer was dried over sodium sulfate, filtered and concentrated. The residue was purified by flash chromatography, eluting with 0%-50% dichloromethane in hexane, to provide the desired product.

Example 135C 5-(benzyloxy)-1-(3-(1-naphthyloxy)propyl)-3-(2-(trifluoromethyl)phenyl)-1H-indole-2-carboxylic acid A mixture of EXAMPLE 135B (30 mg), 2-(trifluoromethyl)phenylboronic acid (15.3 mg), tetrakis(triphenylphosphine)palladium(0) (3.1 mg) and cesium fluoride (16.3 mg) in dimethoxyethane (1.4 ml) and methanol (0.7 ml) was heated at 100° C. in a microwave reactor (CEM Discover) for 30 minutes and was concentrated. The residue was purified by flash chromatography, eluting with 0%-100% dichloromethane in hexane, to provide ethyl 5-(benzyloxy)-1-(3-(naphthalen-1-yloxy)propyl)-3-(2-(trifluoromethyl)phenyl)-1H-indole-2-carboxylate. This ester was hydrolyzed with aqueous NaOH in tetrahydrofuran and methanol to provide the title compound. $^1$H NMR (500 MHz, dimethyl sulfoxide-d$_6$) δ 12.67 (s, 1H), 8.04-8.40 (m, 1H), 7.87 (d, J=7.32 Hz, 1H), 7.82 (d, J=7.63 Hz, 1H), 7.69 (t, J=7.32 Hz, 1H), 7.57-7.65 (m, 2H), 7.44-7.56 (m, 3H), 7.26-7.41 (m, 7H), 6.97 (dd, J=9.00, 2.29 Hz, 1H), 6.85 (d, J=7.93 Hz, 1H), 6.55 (d, J=2.14 Hz, 1H), 4.83-4.98 (m, 4H), 4.05-4.24 (m, 2H), 2.28-2.40 (m, 2H).

Example 136

5-fluoro-3-(2-methylphenyl)-1-(3-(1-naphthyloxy)propyl)-1H-indole-2-carboxylic acid $^1$H NMR (500 MHz, dimethyl sulfoxide-d$_6$) δ 12.87 (s, 1H), 8.17 (d, J=8.24 Hz, 1H), 7.86 (d, J=7.93 Hz, 1H), 7.74 (dd, J=9.15, 4.27 Hz, 1H), 7.42-7.57 (m, 3H), 7.38 (t, J=7.93 Hz, 1H), 7.24-7.32 (m, 2H), 7.22 (t, J=7.32 Hz, 1H), 7.07-7.15 (m, 2H), 6.87 (d, J=7.32 Hz, 1H), 6.75 (dd, J=9.31, 2.59 Hz, 1H), 4.77-5.03 (m, 2H), 4.18 (t, J=5.80 Hz, 2H), 2.28-2.43 (m, 2H), 2.01 (s, 3H).

Example 137

5-fluoro-1-(3-(1-naphthyloxy)propyl)-1H-indole-2-carboxylic acid $^1$H NMR (500 MHz, dimethyl sulfoxide-d$_6$) δ 13.08 (s, 1H), 8.21 (d, J=7.93 Hz, 1H), 7.86 (d, J=7.63 Hz, 1H), 7.65 (dd, J=9.00, 4.12 Hz, 1H), 7.47-7.58 (m, 2H), 7.41-7.48 (m, 2H), 7.37 (t, J=7.78 Hz, 1H), 7.24 (s, 1H), 7.01-7.11 (m, 1H), 6.85 (d, J=7.32 Hz, 1H), 4.88 (t, J=6.87 Hz, 2H), 4.13 (t, J=5.49 Hz, 2H), 2.21-2.37 (m, 2H).

Example 138

5-fluoro-1-(3-(1-naphthyloxy)propyl)-3-(2-(trifluoromethyl)phenyl)-1H-indole-2-carboxylic acid $^1$H NMR (500 MHz, dimethyl sulfoxide-d$_6$) δ 12.89 (s, 1H), 8.19 (d, J=8.24 Hz, 1H), 7.87 (d, J=7.93 Hz, 1H), 7.82 (d, J=7.63 Hz, 1H), 7.75 (dd, J=9.15, 4.27 Hz, 1H), 7.69 (t, J=7.48 Hz, 1H), 7.61 (t, J=7.63 Hz, 1H), 7.43-7.57 (m, 3H), 7.38 (t, J=7.93 Hz, 1H), 7.34 (d, J=7.63 Hz, 1H), 7.07-7.16 (m, 1H), 6.85 (d, J=7.63 Hz, 1H), 6.73 (dd, J=9.31, 2.29 Hz, 1H), 4.72-5.16 (m, 2H), 4.06-4.28 (m, 2H), 2.27-2.42 (m, 2H).

Example 139

5-fluoro-3-(2-isopropylphenyl)-1-(3-(1-naphthyloxy)propyl)-1H-indole-2-carboxylic acid $^1$H NMR (500 MHz, dimethyl sulfoxide-$d_6$) δ 12.81 (s, 1H), 8.14 (d, J=8.24 Hz, 1H), 7.86 (d, J=7.93 Hz, 1H), 7.74 (dd, J=9.15, 4.27 Hz, 1H), 7.50-7.55 (m, 1H), 7.44-7.50 (m, 2H), 7.32-7.42 (m, 3H), 7.16-7.22 (m, 1H), 7.09-7.15 (m, 1H), 7.03-7.07 (m, 1H), 6.86 (d, J=7.63 Hz, 1H), 6.70 (dd, J=9.15, 2.44 Hz, 1H), 4.72-5.06 (m, 2H), 4.17 (t, J=5.80 Hz, 2H), 2.58-2.78 (m, 1H), 2.24-2.43 (m, 2H), 1.01 (d, J=6.71 Hz, 3H), 0.94 (d, J=7.02 Hz, 3H).

Example 140

4-(2-methylphenyl)-1-(3-(1-naphthyloxy)propyl)-3-((3-(trifluoromethoxy)phenyl)amino)-1H-indole-2-carboxylic acid $^1$H NMR (500 MHz, dimethyl sulfoxide-$d_6$) δ 13.09 (s, 1H), 8.20-8.35 (m, 1H), 7.81-7.92 (m, 1H), 7.67 (d, J=8.54 Hz, 1H), 7.50-7.58 (m, 2H), 7.47 (d, J=8.24 Hz, 1H), 7.39 (t, J=7.93 Hz, 1H), 7.27 (dd, J=8.39, 7.17 Hz, 1H), 7.10 (s, 1H), 6.82-6.98 (m, 4H), 6.74-6.82 (m, 3H), 6.30 (d, J=8.24 Hz, 1H), 5.96 (d, J=7.93 Hz, 1H), 5.90 (s, 1H), 4.78-5.01 (m, 2H), 4.19 (t, J=5.80 Hz, 2H), 2.31-2.44 (m, 2H), 1.89 (s, 3H).

Example 141

5-(benzyloxy)-1-(3-(1-naphthyloxy)propyl)-3-((3-(trifluoromethoxy)phenyl)amino)-1H-indole-2-carboxylic acid $^1$H NMR (400 MHz, dimethyl sulfoxide-$d_6$) δ 8.22 (d, J=7.67 Hz, 1H), 8.04 (s, 1H), 7.86 (dd, J=7.21, 1.69 Hz, 1H), 7.57 (d, J=8.90 Hz, 1H), 7.48-7.55 (m, 2H), 7.43-7.47 (m, 1H), 7.28-7.41 (m, 6H), 7.17 (t, J=8.13 Hz, 1H), 6.92-6.99 (m, 1H), 6.84 (d, J=7.67 Hz, 1H), 6.76 (d, J=2.45 Hz, 1H), 6.64-6.72 (m, 2H), 6.61 (d, J=6.14 Hz, 1H), 4.94 (s, 2H), 4.78-4.86 (m, 2H), 4.13 (t, J=5.98 Hz, 2H), 2.24-2.35 (m, 2H).

Example 142

5-(benzyloxy)-1-(3-(1-naphthyloxy)propyl)-1H-indole-2-carboxylic acid $^1$H NMR (400 MHz, dimethyl sulfoxide-$d_6$) δ 8.23 (d, J=8.29 Hz, 1H), 7.86 (d, J=7.06 Hz, 1H), 7.49-7.58 (m, 3H), 7.42-7.48 (m, 3H), 7.39 (t, J=7.06 Hz, 3H), 7.29-7.36 (m, 1H), 7.23 (d, J=2.15 Hz, 1H), 7.14 (s, 1H), 6.91 (dd, J=8.90, 2.46 Hz, 1H), 6.84 (d, J=7.98 Hz, 1H), 5.08 (s, 2H), 4.83 (t, J=6.60 Hz, 2H), 4.12 (t, J=6.29 Hz, 2H), 2.27-2.34 (m, 2H).

Example 143

5-(benzyloxy)-3-(2-isopropylphenyl)-1-(3-(1-naphthyloxy)propyl)-1H-indole-2-carboxylic acid $^1$H NMR (400 MHz, dimethyl sulfoxide-$d_6$) δ 8.19 (d, J=7.98 Hz, 1H), 7.86 (d, J=7.36 Hz, 1H), 7.60 (d, J=9.51 Hz, 1H), 7.43-7.56 (m, 3H), 7.25-7.43 (m, 8H), 7.13-7.21 (m, 1H), 7.04 (d, J=6.75 Hz, 1H), 6.98 (dd, J=9.21, 2.45 Hz, 1H), 6.85 (d, J=7.36 Hz, 1H), 6.53 (d, J=2.15 Hz, 1H), 4.74-5.06 (m, 4H), 4.16 (t, J=5.68 Hz, 2H), 2.64-2.81 (m, 1H), 2.27-2.42 (m, 2H), 1.00 (d, J=7.06 Hz, 3H), 0.92 (d, J=6.75 Hz, 3H).

Example 144

3-(2-(te-butoxymethyl)phenyl)-5-fluoro-1-(3-(1-naphthyloxy)propyl)-1H-indole-2-carboxylic acid $^1$H NMR (400 MHz, dimethyl sulfoxide-$d_6$) δ 8.22 (d, J=7.67 Hz, 1H), 7.86 (d, J=7.67 Hz, 1H), 7.70 (dd, J=9.05, 4.14 Hz, 1H), 7.43-7.57 (m, 4H), 7.26-7.41 (m, 3H), 7.15 (dd, J=7.36, 1.23 Hz, 1H), 7.05-7.12 (m, 1H), 6.85 (d, J=7.36 Hz, 1H), 6.77 (dd, J=9.51, 2.45 Hz, 1H), 4.77-5.04 (m, 2H), 4.17 (t, J=5.68 Hz, 2H), 4.11 (q, J=10.74 Hz, 2H), 2.28-2.42 (m, 2H), 0.75-0.88 (m, 9H).

Example 145

5-fluoro-1-(3-(1-naphthyloxy)propyl)-3-(2-((3-(trifluoromethyl)phenoxy)methyl)phenyl)-1H-indole-2-carboxylic acid $^1$H NMR (400 MHz, dimethyl sulfoxide-$d_6$) δ 8.17 (d, J=7.98 Hz, 1H), 7.85 (d, J=7.36 Hz, 1H), 7.66 (dd, J=9.21, 4.30 Hz, 1H), 7.38-7.60 (m, 6H), 7.21-7.37 (m, 3H), 7.12 (d, J=7.98 Hz, 1H), 7.03-7.11 (m, 1H), 6.92 (dd, J=8.13, 1.99 Hz, 1H), 6.75-6.83 (m, 3H), 4.73-5.00 (m, 4H), 3.96-4.15 (m, J=6.44 Hz, 2H), 2.17-2.29 (m, 2H).

Example 146

5-chloro-3-(2-isopropylphenyl)-1-(3-(1-naphthyloxy)propyl)-1H-indole-2-carboxylic acid $^1$H NMR (400 MHz, dimethyl sulfoxide-$d_6$) δ 8.10 (d, J=8.29 Hz, 1H), 7.86 (d, J=7.67 Hz, 1H), 7.75 (d, J=8.90 Hz, 1H), 7.52 (t, J=6.90 Hz, 1H), 7.43-7.49 (m, 2H), 7.32-7.42 (m, 3H), 7.25 (dd, J=8.90, 1.84 Hz, 1H), 7.15-7.22 (m, 1H), 7.04 (d, J=6.75 Hz, 1H), 6.98 (d, J=1.84 Hz, 1H), 6.85 (d, J=7.36 Hz, 1H), 4.92 (t, J=7.36 Hz, 2H), 4.17 (t, J=5.83 Hz, 2H), 2.59-2.74 (m, 1H), 2.30-2.44 (m, 2H), 1.01 (d, J=6.75 Hz, 3H), 0.92 (d, J=7.06 Hz, 3H).

Example 147

5-chloro-3-(2-methylphenyl)-1-(3-(1-naphthyloxy)propyl)-1H-indole-2-carboxylic acid $^1$H NMR (400 MHz, dimethyl sulfoxide-$d_6$) δ 8.13 (d, J=8.59 Hz, 1H), 7.86 (d, J=8.59 Hz, 1H), 7.74 (d, J=8.90 Hz, 1H), 7.42-7.58 (m, 3H), 7.38 (t, J=7.98 Hz, 1H), 7.17-7.34 (m, 4H), 7.12 (d, J=7.06 Hz, 1H), 7.02 (d, J=1.84 Hz, 1H), 6.87 (d, J=7.36 Hz, 1H), 4.75-5.01 (m, 2H), 4.18 (t, J=5.83 Hz, 2H), 2.32-2.43 (m, 2H), 1.99 (s, 3H).

Example 148

5-hydroxy-3-(2-isopropylphenyl)-1-(3-(5,6,7,8-tetrahydronaphthalen-1-yloxy)propyl)-1H-indole-2-carboxylic acid $^1$H NMR (400 MHz, dimethyl sulfoxide-$d_6$) δ 8.84 (s, 1H), 7.35-7.46 (m, 2H), 7.32 (t, J=6.75 Hz, 1H), 7.13-7.21 (m, 1H), 7.04 (d, J=7.98 Hz, 1H), 6.98 (t, J=8.13 Hz, 1H), 6.80 (d, J=7.67 Hz, 1H), 6.63 (d, J=8.29 Hz, 1H), 6.59 (d, J=8.29 Hz, 1H), 6.37 (d, J=2.15 Hz, 1H), 4.72 (t, J=7.36 Hz, 2H), 3.92 (t, J=5.98 Hz, 2H), 2.65-2.73 (m, 2H), 2.57-2.64 (m, 2H), 2.14-2.25 (m, 2H), 1.64-1.78 (m, 4H), 1.04 (d, J=6.75 Hz, 3H), 0.98 (d, J=6.75 Hz, 3H).

Example 149

5-hydroxy-3-(2-isopropylphenyl)-1-(3-(1-naphthyloxy)propyl)-1H-indole-2-carboxylic acid Example 149A ethyl 5-(benzyloxy)-3-(2-isopropylphenyl)-1-(3-(naphthalen-1-yloxy)propyl)-1H-indole-2-carboxylate The title compound was prepared according to the procedure for EXAMPLE 135C by substituting 2-(isopropyl)phenylboronic acid for 2-(trifluoromethyl)phenylboronic acid.

Example 149B ethyl 5-hydroxy-3-(2-isopropylphenyl)-1-(3-(naphthalen-1-yloxy)propyl)-1H-indole-2-carboxylate A mixture of EXAMPLE 149A (250 mg) and dihydroxypalladium (on carbon) (20 mg) in tetrahydrofuran was stirred a room temperature under a hydrogen atmosphere (30 psi) for 29 hours. The insoluble material was filtered off and the filtrate was concentrated. The residue was purified by flash chromatography, eluting with dichloromethane to provide the title compound.

Example 149C 5-hydroxy-3-(2-isopropylphenyl)-1-(3-(1-naphthyloxy)propyl)-1H-indole-2-carboxylic acid To a solution of EXAMPLE 149B (22 mg) in tetrahydrofuran (2 ml) and methanol (2 ml) was added 10% NaOH 0.3 ml. The reaction was heated at 70° C. for 24 hours, cooled, acidified with diluted aqueous HCl and concentrated. The residue was purified by RPHPLC to provide the title compound. $^1$H NMR (400 MHz, dimethyl sulfoxide-$d_6$) δ 8.83 (s, 1H), 8.20-8.23 (m, 1H), 7.85-7.88 (m, 1H), 7.45-7.55 (m, 5H), 7.34-7.40 (m, 2H), 7.28-7.34 (m, 1H), 7.17 (td, J=7.36, 1.23 Hz, 1H), 7.04 (dd, J=7.52, 1.38 Hz, 1H), 6.85 (d, J=7.36 Hz, 1H), 6.75 (dd, J=8.90, 2.45 Hz, 1H), 6.37 (d, J=2.15 Hz, 1H), 4.84 (t, J=7.52 Hz, 2H), 4.15 (t, J=5.68 Hz, 2H), 2.63-2.87 (m, 1H), 2.25-2.41 (m, 2H), 1.02 (d, J=6.75 Hz, 3H), 0.96 (d, J=7.06 Hz, 3H).

Example 150

3-(2-isopropylphenyl)-5-(4-morpholin-4-ylbutoxy)-1-(3-(1-naphthyloxy)propyl)-1H-indole-2-carboxylic acid A mixture of EXAMPLE 149A (36 mg), 1-chloro-4-iodobutane (0.043 ml) and cesium carbonate (116 mg) in N,N-dimethylformamide (2 ml) was stirred at room temperature overnight. The inorganic salt was filtered off. To the N,N-dimethylformamide solution was added morpholine (0.2 ml) and the resulting mixture was heated at 60° C. for 5 hours. The reaction mixture was concentrated and the residue was purified by RPHPLC (mobile phase: 10%-100% acetonitrile in 0.1% TFA aqueous solution during 60 min) on a C18 column to give ethyl 3-(2-isopropylphenyl)-5-(4-morpholinobutoxy)-1-(3-(naphthalen-1-yloxy)propyl)-1H-indole-2-carboxylate. This ester was hydrolyzed with aqueous NaOH in a mixture of tetrahydrofuran and methanol to provide the title compound. $^1$H NMR (400 MHz, dimethyl sulfoxide-$d_6$) δ 9.52 (s, 1H), 8.20 (d, J=8.29 Hz, 1H), 7.87 (d, J=7.98 Hz, 1H), 7.59 (d, J=8.90 Hz, 1H), 7.43-7.57 (m, 3H), 7.30-7.43 (m, 3H), 7.14-7.23 (m, 1H), 7.06 (d, J=7.36 Hz, 1H), 6.89 (dd, J=9.05, 2.30 Hz, 1H), 6.85 (d, J=7.67 Hz, 1H), 6.43 (d, J=2.45 Hz, 1H), 4.88 (t, J=7.21 Hz, 2H), 4.15 (t, J=5.83 Hz, 2H), 3.89-4.03 (m, J=11.97 Hz, 2H), 3.75-3.89 (m, 2H), 3.55-3.70 (m, 2H), 3.07-3.17 (m, 2H), 3.02 (s, br, 2H), 2.61-2.78 (m, 2H), 2.23-2.45 (m, 2H), 1.60-1.85 (m, 4H).

Example 151

5-fluoro-1-(3-(1-naphthyloxy)propyl)-3-(1,3,5-trimethyl-1H-pyrazol-4-yl)-1H-indole-2-carboxylic acid A mixture of 1,3,5-trimethyl-4-(4,4,5,5-tetramethyl-1,3,2-dioxaborolan-2-yl)-1H-pyrazole (43.2 mg), ethyl 3-bromo-5-fluoro-1-(3-(naphthalen-1-yloxy)propyl)-1H-indole-2-carboxylate (The synthesis of this compound was described in EXAMPLE 134B as an intermediate) (43 mg), dicyclohexyl(2',6'-dimethoxybiphenyl-2-yl)phosphine (15.01 mg) and $K_3PO_4$ (58.2 mg) in toluene (2.1 ml) was heated in a microwave reactor (CEM Discover) at 110° C. for 2 hours. The reaction was directly loaded into a silica cartridge, and eluted with 0%-25% ethyl acetate in dichloromethane. The collected desired ester was hydrolyzed with NaOH in tetrahydrofuran-methanol-$H_2O$ at 50° C. overnight to provide the title compound. $^1$H NMR (400 MHz, dimethyl sulfoxide-$d_6$) δ 8.15 (d, J=8.90 Hz, 1H), 7.86 (d, J=7.36 Hz, 1H), 7.71 (dd, J=9.21, 4.30 Hz, 1H), 7.42-7.56 (m, 3H), 7.32-7.41 (m, 1H), 7.05-7.16 (m, 1H), 6.92 (dd, J=9.36, 2.61 Hz, 1H), 6.86 (d, J=7.36 Hz, 1H), 4.69-5.00 (m, 2H), 4.17 (t, J=5.83 Hz, 2H), 3.72 (s, 3H), 2.27-2.43 (m, 2H), 1.99 (s, 3H), 1.90 (s, 3H).

Example 152

3-(2-isopropylphenyl)-1-(3-(1-naphthyloxy)propyl)-5-phenyl-1H-indole-2-carboxylic acid A mixture of ethyl 5-chloro-3-(2-isopropylphenyl)-1-(3-(naphthalen-1-yloxy)propyl)-1H-indole-2-carboxylate (the synthesis of this compound was similar to the intermediate described in EXAMPLE 134) (56 mg), phenylboronic acid (26 mg), diacetoxypalladium (2.39 mg), dicyclohexyl(2',6'-dimethoxybiphenyl-2-yl)phosphine (8.74 mg) and $K_3PO_4$ (67.8 mg) was heated at 180° C. in a CEM microwave synthesizer for 1 hour. The reaction was concentrated and the residue was purified by flash chromatography, eluting with 0-50% dichloromethane in hexane. The collected desired ester was saponified with NaOH in tetrahydrofuran-methanol-$H_2O$ at 50° C. overnight to provide the title compound. $^1$H NMR (400 MHz, dimethyl sulfoxide-$d_6$) δ 12.76 (s, 1H), 8.17 (d, J=8.29 Hz, 1H), 7.86 (d, J=7.67 Hz, 1H), 7.78 (d, J=8.90 Hz, 1H), 7.43-7.58 (m, 6H), 7.32-7.44 (m, 5H), 7.28 (t, J=7.21 Hz, 1H), 7.22 (d, J=1.84 Hz, 1H), 7.16-7.21 (m, 1H), 7.06-7.12 (m, 1H), 6.87 (d, J=7.36 Hz, 1H), 4.95 (t, J=7.06 Hz, 2H), 4.21 (t, J=6.14 Hz, 2H), 2.68-2.82 (m, J=7.06 Hz, 1H), 2.37-2.47 (m, 2H), 1.03 (d, J=6.75 Hz, 3H), 0.96 (d, J=6.75 Hz, 3H).

Example 153

3-(2,6-dimethylphenyl)-5-fluoro-1-(3-(1-naphthyloxy)propyl)-1H-indole-2-carboxylic acid $^1$H NMR (400 MHz, dimethyl sulfoxide-$d_6$) δ 12.72 (s, 1H), 8.19 (d, J=7.98 Hz, 1H), 7.86 (d, J=7.36 Hz, 1H), 7.74

(dd, J=9.21, 4.30 Hz, 1H), 7.42-7.56 (m, 3H), 7.37 (t, J=7.98 Hz, 1H), 7.05-7.20 (m, 4H), 6.84 (d, J=7.67 Hz, 1H), 6.62 (dd, J=9.05, 2.61 Hz, 1H), 4.93 (t, J=6.90 Hz, 2H), 4.14 (t, J=5.98 Hz, 2H), 2.26-2.44 (m, 2H), 1.87 (s, 6H).

Example 154

3-(2-isopropylphenyl)-1-(3-(1-naphthyloxy)propyl)-1H-indole-2-carboxylic acid $^1$H NMR (400 MHz, dimethyl sulfoxide-$d_6$) δ 8.20 (d, J=7.98 Hz, 1H), 7.83-7.91 (m, 1H), 7.67 (d, J=8.29 Hz, 1H), 7.43-7.57 (m, 3H), 7.30-7.42 (m, 3H), 7.22-7.28 (m, 1H), 7.13-7.22 (m, 1H), 6.98-7.11 (m, 3H), 6.86 (d, J=7.36 Hz, 1H), 4.83-4.97 (m, 2H), 4.18 (t, J=5.98 Hz, 2H), 2.62-2.75 (m, 1H), 2.29-2.43 (m, 2H), 1.02 (d, J=6.75 Hz, 3H), 0.94 (d, J=7.06 Hz, 3H).

Example 155

1-(3-(1-naphthyloxy)propyl)-5-((1E)-pent-1-enyl)-1H-indole-2-carboxylic acid $^1$H NMR (500 MHz, dimethyl sulfoxide-$d_6$) δ 12.94 (s, 1H), 8.24 (d, J=7.93 Hz, 1H), 7.87 (d, J=7.63 Hz, 1H), 7.60 (s, 1H), 7.48-7.56 (m, 3H), 7.46 (d, J=8.24 Hz, 1H), 7.37 (t, J=7.93 Hz, 1H), 7.32 (dd, J=8.85, 1.22 Hz, 1H), 7.20 (s, 1H), 6.85 (d, J=7.63 Hz, 1H), 6.44 (d, J=15.87 Hz, 1H), 6.12-6.25 (m, 1H), 4.85 (t, J=6.87 Hz, 2H), 4.13 (t, J=5.80 Hz, 2H), 2.26-2.35 (m, 2H), 2.09-2.21 (m, 2H), 1.38-1.53 (m, 2H), 0.92 (t, J=7.32 Hz, 3H).

Example 156

3-(2,6-dimethylphenyl)-1-(3-(1-naphthyloxy)propyl)-1H-indole-2-carboxylic acid $^1$H NMR (400 MHz, dimethyl sulfoxide-$d_6$) δ 12.59 (s, 1H), 8.21-8.27 (m, 1H), 7.83-7.89 (m, 1H), 7.68 (d, J=8.59 Hz, 1H), 7.42-7.57 (m, 3H), 7.37 (t, J=7.82 Hz, 1H), 7.20-7.27 (m, 1H), 7.07-7.18 (m, 3H), 6.94-7.05 (m, 2H), 6.84 (d, J=7.67 Hz, 1H), 4.94 (t, J=7.06 Hz, 2H), 4.15 (t, J=5.83 Hz, 2H), 2.32-2.43 (m, 2H), 1.88 (s, 6H).

Example 157

1-(3-(1-naphthyloxy)propyl)-3-(1,3,5-trimethyl-1H-pyrazol-4-yl)-1H-indole-2-carboxylic acid $^1$H NMR (400 MHz, dimethyl sulfoxide-$d_6$) δ 8.20 (d, J=7.98 Hz, 1H), 7.86 (d, J=7.98 Hz, 1H), 7.66 (d, J=8.90 Hz, 1H), 7.42-7.56 (m, 3H), 7.33-7.40 (m, 1H), 7.20-7.28 (m, 2H), 7.07 (t, J=7.52 Hz, 1H), 6.86 (d, J=7.67 Hz, 1H), 4.73-5.02 (m, 2H), 4.18 (t, J=5.83 Hz, 2H), 3.74 (s, 3H), 2.30-2.44 (m, 2H), 2.01 (s, 3H), 1.92 (s, 3H).

Example 158

3-(2-chlorophenyl)-5-fluoro-1-(3-(1-naphthyloxy)propyl)-1H-indole-2-carboxylic acid $^1$H NMR (400 MHz, dimethyl sulfoxide-$d_6$) δ 13.00 (s, 1H), 8.18 (d, J=7.98 Hz, 1H), 7.86 (d, J=7.36 Hz, 1H), 7.75 (dd, J=9.05, 4.14 Hz, 1H), 7.43-7.59 (m, 4H), 7.31-7.43 (m, 4H), 7.06-7.17 (m, 1H), 6.78-6.92 (m, 2H), 4.64-5.21 (m, 2H), 4.19 (t, J=5.83 Hz, 2H), 2.26-2.42 (m, 2H).

Example 159

3-((1E)-5-(dimethylamino)pent-1-enyl)-5-fluoro-1-(3-(1-naphthyloxy)propyl)-1H-indole-2-carboxylic acid

Example 159A (E)-ethyl 3-(5-chloropent-1-enyl)-5-fluoro-1-(3-(naphthalen-1-yloxy)propyl)-1H-indole-2-carboxylate A mixture of ethyl 3-bromo-5-fluoro-1-(3-(naphthalen-1-yloxy)propyl)-1H-indole-2-carboxylate (The synthesis of this compound was described in EXAMPLE 134B as an intermediate) (404 mg), (E)-2-(5-chloropent-1-enyl)-4,4,5,5-tetramethyl-1,3,2-dioxaborolane (0.394 ml), diacetoxypalladium (19.28 mg), dicyclohexyl(2',6'-dimethoxybiphenyl-2-yl)phosphine (70.5 mg) and $K_3PO_4$ (547 mg) was heated in a microwave reactor (CEM Discover) at 100° C. for 1 hour. The insoluble material was removed by filtration and the filtrate was concentrated. The residue was purified by flash chromatography, eluting with dichloromethane to provide the title compound.

Example 159B

Example 159A (100 mg) in tetrahydrofuran (1 ml) was mixed with 1 M dimethylamine in methanol (10 ml) and the resulting solution was heated 50° C. for 3 days and concentrated. The residue was dissolved in tetrahydrofuran and methanol. 3 ml of 10% aqueous NaOH was added. The mixture was heated at 50° C. overnight and was concentrated. The residue was purified by RPHPLC (mobile phase: 10%-100% acetonitrile in 0.1% TFA aqueous solution during 60 min) on a C18 column to provide the title compound. $^1$H NMR (500 MHz, dimethyl sulfoxide-$d_6$) δ 13.56 (s, br, 1H), 9.39 (s, br, 1H), 8.19 (d, J=7.93 Hz, 1H), 7.87 (d, J=7.93 Hz, 1H), 7.64-7.73 (m, 2H), 7.43-7.59 (m, 3H), 7.38 (t, J=7.93 Hz, 1H), 7.04-7.18 (m, 2H), 6.85 (d, J=7.32 Hz, 1H), 6.17-6.31 (m, 1H), 4.82 (t, J=7.02 Hz, 2H), 4.14 (t, J=5.80 Hz, 2H), 3.06-3.16 (m, 2H), 2.80 (d, J=4.58 Hz, 6H), 2.22-2.35 (m, 4H), 1.78-1.90 (m, 2H).

Example 160

3-((1E)-6-((2-carboxybenzoyl)amino)hex-1-enyl)-5-fluoro-1-(3-(1-naphthyloxy)propyl)-1H-indole-2-carboxylic acid

Example 160A (E)-ethyl 3-(6-chlorohex-1-enyl)-5-fluoro-1-(3-(naphthalen-1-yloxy)propyl)-1H-indole-2-carboxylate The title compound was prepared by substituting (E)-2-(6-chlorohex-1-enyl)-4,4,5,5-tetramethyl-1,3,2-dioxaborolane for (E)-2-(5-chloropent-1-enyl)-4,4,5,5-tetramethyl-1,3,2-dioxaborolane in EXAMPLE 159A.

Example 160B 3-((1E)-6-((2-carboxybenzoyl)amino)hex-1-enyl)-5-fluoro-1-(3-(1-naphthyloxy)propyl)-1H-indole-2-carboxylic acid A mixture of EXAMPLE 160A (531 mg) and potassium 1,3-dioxoisoindolin-2-ide (213 mg) in N,N-dimethylformamide (10 ml) was heated at 80° C. for 8 hours. The reaction was diluted with ethyl acetate and washed with water. The organic layer was dried over sodium sulfate and was concentrated. The residue was purified by flash chromatography, eluting with 0-100% ethyl acetate in dichloromethane to give (E)-ethyl 3-(6-(1,3-dioxoisoindolin-2-yl)hex-1-enyl)-5-fluoro-1-(3-(naphthalen-1-yloxy)propyl)-1H-indole-2-carboxylate. This ester was dissolved in a mixture of tetrahydrofuran and methanol and 5 equivalents of aqueous NaOH (10%) was added. The mixture was heated at 50° C. for 5 hours. The reaction mixture was concentrated and the residue was dissolved in dimethyl sulfoxide and trifluoroacetic acid-methanol (3:1), and purified by RPHPLC to provide the title compound. $^1$H NMR (400 MHz, dimethyl sulfoxide-$d_6$) δ 13.06 (s, 2H), 8.25 (t, J=5.52 Hz, 1H), 8.19 (dd, J=7.83, 1.38 Hz, 1H), 7.86 (dd, J=7.21, 1.99 Hz, 1H), 7.74 (dd, J=7.52, 1.38 Hz, 1H), 7.60-7.69 (m, 2H), 7.43-7.58 (m, 5H), 7.34-7.41 (m, 2H), 6.99-7.16 (m, 2H), 6.85 (d, J=7.36 Hz, 1H), 6.15-6.32 (m, 1H), 4.65-4.96 (m, 2H), 4.13 (t, J=5.68 Hz, 2H), 3.20-3.29 (m, 2H), 2.20-2.36 (m, 4H), 1.49-1.67 (m, 4H).

Example 161

3-((1E)-6-aminohex-1-enyl)-5-fluoro-1-(3-(1-naphthyloxy)propyl)-1H-indole-2-carboxylic acid (E)-ethyl 3-(6-(1,3-dioxoisoindolin-2-yl)hex-1-enyl)-5-fluoro-1-(3-(naphthalen-1-yloxy)propyl)-1H-indole-2-carboxylate (The synthesis of this compound was described in EXAMPLE 160B as an intermediate.) was dissolved in a mixture of tetrahydrofuran and methanol and 5 equivalents of aqueous NaOH (10%) was added. The mixture was heated at 50° C. for 2 days. The reaction mixture was concentrated and the residue was purified by reverse phase HPLC (mobile phase: 0-100% acetonitrile in 0.1% TFA aqueous solution during 60 min) on a C18 column to provide the title compound. $^1$H NMR (400 MHz, dimethyl sulfoxide-$d_6$) δ 8.18 (d, J=9.21 Hz, 1H), 7.82-7.89 (m, 1H), 7.57-7.70 (m, 4H), 7.42-7.55 (m, 4H), 7.37 (t, J=7.67 Hz, 1H), 7.01-7.14 (m, 2H), 6.84 (d, J=7.67 Hz, 1H), 6.14-6.29 (m, 1H), 4.80 (t, J=7.83 Hz, 2H), 4.13 (t, J=5.68 Hz, 2H), 2.70-2.97 (m, 2H), 2.11-2.37 (m, 4H), 1.41-1.76 (m, 4H).

Example 162

3-(6-aminohexyl)-5-fluoro-1-(3-(1-naphthyloxy)propyl)-1H-indole-2-carboxylic acid A mixture of (E)-ethyl 3-(6-(1,3-dioxoisoindolin-2-yl)hex-1-enyl)-5-fluoro-1-(3-(naphthalen-1-yloxy)propyl)-1H-indole-2-carboxylate (The synthesis of this compound was described in EXAMPLE 160B as an intermediate.) (270 mg) and hydrazine (0.030 ml) in tetrahydrofuran (1.00 ml) and ethanol (3 ml) was heated at 50° C. overnight and concentrated. The residue was dissolved in tetrahydrofuran and methanol and then aqueous 10% NaOH was added. The resulting was heated at 50° C. overnight and concentrated. The residue was purified by RPHPLC to provide the title compound. $^1$H NMR (400 MHz, dimethyl sulfoxide-$d_6$) δ 8.17 (dd, J=8.44, 1.07 Hz, 1H), 7.84-7.89 (m, 1H), 7.60 (dd, J=9.21, 4.30 Hz, 1H), 7.41-7.56 (m, 4H), 7.32-7.40 (m, 1H), 7.01-7.11 (m, 1H), 6.84 (d, J=7.06 Hz, 1H), 4.80 (t, J=7.21 Hz, 2H), 4.12 (t, J=5.83 Hz, 2H), 2.94-3.06 (m, 2H), 2.75 (t, J=8.29 Hz, 2H), 2.20-2.35 (m, 2H), 1.43-1.63 (m, 4H), 1.27-1.36 (m, 4H).

Example 163

3-(5-(dimethylamino)pentyl)-5-fluoro-1-(3-(1-naphthyloxy)propyl)-1H-indole-2-carboxylic acid A mixture of EXAMPLE 159 (45 mg) and Pt/C (5%) (10 mg) in tetrahydrofuran (2 ml) was stirred under hydrogen (30 psi) at room temperature for 2.5 hours. The insoluble material was filtered off and the filtrate was concentrated. The residue was purified by RPHPLC to provide the desired product. $^1$H NMR (400 MHz, dimethyl sulfoxide-$d_6$) δ 9.28 (s, 1H), 8.17 (d, J=7.67 Hz, 1H), 7.81-7.91 (m, 1H), 7.61 (dd, J=9.21, 4.30 Hz, 1H), 7.43-7.56 (m, 4H), 7.37 (t, J=7.82 Hz, 1H), 7.01-7.10 (m, 1H), 6.84 (d, J=7.36 Hz, 1H), 4.80 (t, J=6.90 Hz, 2H), 4.12 (t, J=5.83 Hz, 2H), 2.91-3.07 (m, 4H), 2.19-2.35 (m, 2H), 1.50-1.69 (m, 4H), 1.25-1.39 (m, 2H).

Example 164

6-chloro-1-(3-(1-naphthyloxy)propyl)-1H-indole-2-carboxylic acid $^1$H NMR (400 MHz, dimethyl sulfoxide-$d_6$) δ 8.23-8.27 (m, 1H), 7.83-7.87 (m, 1H), 7.71 (s, 1H), 7.67 (d, J=8.29 Hz, 1H), 7.43-7.54 (m, 3H), 7.36 (t, J=7.98 Hz, 1H), 7.27 (s, 1H), 7.06 (dd, J=8.59, 1.53 Hz, 1H), 6.84 (d, J=7.36 Hz, 1H), 4.84 (t, J=6.90 Hz, 2H), 4.11 (t, J=5.68 Hz, 2H), 2.27-2.33 (m, 2H).

Example 165

3-(2-((1 E)-5-(dimethylamino)pent-1-enyl)phenyl)-5-fluoro-1-(3-(1-naphthyloxy)propyl)-1H-indole-2-carboxylic acid $^1$H NMR (500 MHz, dimethyl sulfoxide-$d_6$) δ 12.90 (s, 1H), 9.20 (s, 1H), 8.16 (d, J=8.24 Hz, 1H), 7.87 (d, J=7.93 Hz, 1H), 7.72-7.80 (m, 1H), 7.67 (d, J=7.63 Hz, 1H), 7.50-7.56 (m, 1H), 7.45-7.50 (m, 2H), 7.22-7.41 (m, 3H), 7.10-7.19 (m, 2H), 6.88 (d, J=7.63 Hz, 1H), 6.77 (dd, J=9.46, 2.44 Hz, 1H), 6.04-6.21 (m, 2H), 4.90-5.00 (m, 1H), 4.82-4.91 (m, 1H), 4.20 (t, J=5.80 Hz, 2H), 2.83-2.92 (m, 2H), 2.63-2.72 (m, 6H), 2.34-2.41 (m, 2H), 1.97 (q, J=6.61 Hz, 2H), 1.55-1.65 (m, 2H).

Example 166

3-(2-(dimethylamino)phenyl)-5-fluoro-1-(3-(1-naphthyloxy)propyl)-1H-indole-2-carboxylic acid $^1$H NMR (400 MHz, dimethyl sulfoxide-$d_6$) δ 8.18 (d, J=7.98 Hz, 1H), 7.84-7.88 (m, 1H), 7.74 (dd, J=8.90, 4.30 Hz, 1H), 7.42-7.56 (m, 5H), 7.34-7.41 (m, 1H), 7.19-7.25 (m, 2H), 7.09-7.15 (m, 1H), 6.95 (dd, J=9.21, 2.45 Hz, 1H), 6.87 (d, J=7.06 Hz, 1H), 4.87 (t, J=7.06 Hz, 2H), 4.19 (t, J=5.98 Hz, 2H), 2.63 (s, 6H), 2.33-2.42 (m, 2H).

Example 167

1-(3-(1-naphthyloxy)propyl)-1H-indole-2-carboxylic acid $^1$H NMR (500 MHz, dimethyl sulfoxide-$d_6$) δ 12.96 (s, 1H), 8.06-8.44 (m, 1H), 7.82-7.90 (m, 1H), 7.68 (d, J=7.93 Hz, 1H), 7.60 (d, J=8.54 Hz, 1H), 7.50-7.55 (m, 2H), 7.46 (d, J=8.24 Hz, 1H), 7.37 (t, J=7.93 Hz, 1H), 7.28 (s, 1H), 7.19 (t, J=7.63 Hz, 1H), 7.09 (t, J=7.48 Hz, 1H), 6.84 (d, J=7.63 Hz, 1H), 4.88 (t, J=7.02 Hz, 2H), 4.13 (t, J=5.80 Hz, 2H), 2.27-2.37 (m, 2H).

Example 168

1-methyl-5-(4-(2-methylphenyl)-1-(3-(1-naphthyloxy)propyl)-1H-indol-2-yl)-1H-pyrazol-3-ol

Example 168

1-methyl-5-(4-(2-methylphenyl)-1-[3-(1-naphthyloxy)propyl]-1H-indol-2-yl)-1H-pyrazol-3-ol

Example 168A ethyl 3-(1-(3-(naphthalen-1-yloxy)propyl)-4-o-tolyl-1H-indol-2-yl)-3-oxopropanoate A solution of 1-(3-(naphthalen-1-yloxy)propyl)-4-o-tolyl-1H-indole-2-carboxylic acid (EXAMPLE 103) (536 mg) and 1,1'-carbonyldiimidazole (200 mg) in tetrahydrofuran (10 ml) was stirred at room temperature overnight. To a suspension of potassium ethyl malonate (419 mg) in acetonitrile (10 ml) and triethylamine (0.515 ml) was added magnesium chloride (300 mg) and the mixture was stirred at room temperature for 4 hours then cooled in an ice bath. The above-prepared solution was added dropwise to the first solution, and the resultant suspension was stirred at room temperature for three days. After this time the solvent was removed in vacuo, the residue was taken up in toluene (50 ml), cooled (ice bath), and aqueous HCl (12%) was slowly added. The mixture was warmed to room temperature and extracted twice with ethyl acetate. The combined layers were washed with aqueous $NaHCO_3$, and brine and dried over $Na_2SO_4$. After concentration of the solvent, the residue was loaded on a column and eluted with 5% ethyl acetate in hexane to give the title compound.

Example 168B 1-methyl-5-(4-(2-methylphenyl)-1-[3-(1-naphthyloxy)propyl]-1H-indol-2-yl)-1H-pyrazol-3-ol To a solution of EXAMPLE 168A (75 mg) in dioxane (2 ml) and water (1 ml) was added acetic acid (0.2 ml) and hydrazine monohydrate (0.2 ml). The mixture was stirred at 100° C. overnight, and was purified via RPHPLC to afford the final product. $^1$H NMR (300 MHz, DMSO-$d_6$) δ 8.24 (m, 1H), 7.88 (m, 1H), 7.54 (m, 3H), 7.47 (d, 1H), 7.40 (d, 1H), 7.30 (m, 5H), 7.14 (t, 1H), 6.88 (d, 2H), 6.23 (s, 1H), 5.70 (s, 1H), 4.91 (m, 2H), 4.21 (m, 2H), 3.51 (m, 3H), 2.36 (m, 2H), 2.14 (s, 3H)

Example 169

4-(2-methylphenyl)-1-(3-(1-naphthyloxy)propyl)-2-(1H-tetraazol-5-yl)-1H-indole

Example 169A 1-(3-(naphthalen-1-yloxy)propyl)-4-o-tolyl-1H-indole-2-carboxamide To a solution of 1-(3-(naphthalen-1-yloxy)propyl)-4-o-tolyl-1H-indole-2-carboxylic acid (EXAMPLE 103) (0.9 g) in dichloromethane containing oxalyl chloride (2 mL) was added a few drops of N,N-dimethylformamide. The mixture was stirred for 3 hours at room temperature. The mixture was concentrated under vacuum and the residue was dissolved in dichloromethane (20 ml) and added to a cooled (0° C.) solution of concentrated ammonia in water (30 ml). After the addition, the mixture was stirred for 2 hours and then extracted with ethyl acetate (200 ml). The organic layer was then washed with water, brine and dried over $Na_2SO_4$. Evaporation of the solvent gave the title compound.

Example 169B 1-(3-(naphthalen-1-yloxy)propyl)-4-o-tolyl-1H-indole-2-carbonitrile To a cooled (0° C.) solution of EXAMPLE 168A (880 mg) in tetrahydrofuran (10 mL) and dichloromethane (2 ml) and triethylamine (2 ml) was added, followed by the addition of trifluoroacetic anhydride (2 ml) dropwise. After the addition, the mixture was stirred for 3 hours at 0° C. After this time the mixture was diluted with ethyl acetate (200 mL) and water (80 mL). The aqueous layer was extracted with ether twice. The combined extracts were washed with water (×3), brine and dried over $Na_2SO_4$. Evaporation of solvent gave crude product.

Example 169C 4-(2-methylphenyl)-1-[3-(1-naphthyloxy)propyl]-2-(1H-tetraazol-5-yl)-1H-indole To a mixture of EXAMPLE 168B (416 mg) in N,N-dimethylformamide (10 ml) was added $NaN_3$ (281 mg) and $NH_4Cl$ (231 mg). The mixture was stirred at reflux overnight. After this time the mixture was concentrated under vacuum and the residue was partitioned between ethyl acetate (200 ml) and water (60 ml). The organic phase was washed with brine and dried over $Na_2SO_4$. After concentration of solvent, the residue was dissolved in dimethylsulfoxide/methanol(1: 1, 2 ml) and purified via RPHPLC. $^1$H NMR (300 MHz, DMSO-$d_6$) δ 8.24 (m, 1H), 7.88 (m, 1H), 7.54 (m, 3H), 7.47 (d, 1H), 7.40 (d, 1H), 7.30 (m, 5H), 7.14 (t, 1H), 6.88 (d, 2H), 6.23 (s, 1H), 5.70 (s, 1H), 4.91 (m, 2H), 4.21 (m, 2H), 3.51 (m, 3H), 2.36 (m, 2H), 2.14 (s, 3H).

The foregoing is meant to illustrate the invention but not to limit it. Variations and changes obvious to one skilled in the art are intended to be within the scope of the invention as defined in the appended claims.

We claim:

1. A compound of Formula I,

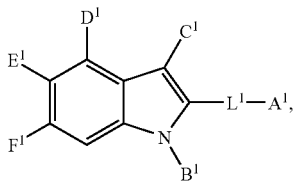

or a therapeutically acceptable salt thereof, wherein
$L^1$ is a bond;
$A^1$ is C(O)OH;
$B^1$ is $R^4$;
$C^1$ is $R^2$ or $R^3$;
each of $D^1$, $E^1$ and $F^1$ is H;
$R^2$ is heteroaryl which is unfused or fused with benzene, heteroarene or $R^{2A}$; $R^{2A}$ is cycloalkane, cycloalkene, heterocycloalkane or heterocycloalkene;
$R^3$ is heterocycloalkyl or heterocycloalkenyl, each of which is unfused or fused with benzene, heteroarene or $R^{3A}$; $R^{3A}$ is cycloalkane, cycloalkene, heterocycloalkane or heterocycloalkene;
$R^4$ is alkyl, alkenyl or alkynyl, each of which is substituted with $OR^5$;
$R^5$ is $R^6$, $R^7$, $R^8$ or $R^9$,
$R^6$ is phenyl which is unfused or fused with benzene, heteroarene or $R^{6A}$; $R^{6A}$ is cycloalkane, cycloalkene, heterocycloalkane or heterocycloalkene;
$R^7$ is heteroaryl which is unfused or fused with benzene, heteroarene or $R^{7A}$; $R^{7A}$ is cycloalkane, cycloalkene, heterocycloalkane or heterocycloalkene;
$R^8$ is cycloalkyl, cycloalkenyl, heterocycloalkyl or heterocycloalkenyl, each of which is unfused or fused with benzene, heteroarene or $R^{8A}$; $R^{8A}$ is cycloalkane, cycloalkene, heterocycloalkane or heterocycloalkene;
$R^9$ is alkyl, alkenyl or alkynyl, each of which is unsubstituted or substituted with one, two, three, four or five of independently selected $R^{9A}$, $OR^{9A}$, $SR^{9A}$, $S(O)R^{9A}$, $SO_2R^{9A}$, $NH_2$, $NHR^{9A}$, $N(R^{9A})_2$, $C(O)R^{9A}$, $C(O)NH_2$, $C(O)NHR^{9A}$, $C(O)N(R^{9A})_2$, $NHC(O)R^{9A}$, $NR^{9A}C(O)R^{9A}$, $NHSO_2R^{9A}$, $NR^{9A}SO_2R^{9A}$, $NHC(O)OR^{9A}$, $NR^{9A}C(O)OR^{9A}$, $SO_2NH_2$, $SO_2NHR^{9A}$, $SO_2N(R^{9A})_2$, $NHC(O)NH_2$, $NHC(O)R^{9A}NHC(O)N(R^{9A})_2$, $NR^{9A}C(O)N(R^{9A})_2$, OH, (O), C(O)OH, CN, $CF_3$, $OCF_3$, $CF_2CF_3$, F, Cl, Br or I;
$R^{9A}$ is $R^{9B}$, $R^{9C}$ or $R^{9D}$;
$R^{9B}$ is phenyl which is unfused or fused with benzene, heteroarene or $R^{9B2}$; $R^{9B2}$ is cycloalkane, cycloalkene, heterocycloalkane or heterocycloalkene;
$R^{9C}$ is heteroaryl which is unfused or fused with benzene, heteroarene or $R^{9C2}$; $R^{9C2}$ is cycloalkane, cycloalkene, heterocycloalkane or heterocycloalkene;
$R^{9D}$ is cycloalkyl, cycloalkenyl, heterocycloalkyl or heterocycloalkenyl, each of which is unfused or fused with benzene, heteroarene or $R^{9D2}$; $R^{9D2}$ is cycloalkane, cycloalkene, heterocycloalkane or heterocycloalkene;
wherein each foregoing cyclic moiety is independently unsubstituted or substituted with one or two or three independently selected $R^{10}$, $OR^{10}$, $C(O)R^{10}$, $NO_2$, $N(R^{10})_2$, $C(O)NHR^{10}$, $SO_2N(R^{10})_2$, C(O)OH, OH, (O), $CF_3$, $OCF_3$, F, Cl, Br or I;
$R^{10}$ is $R^{11}$, $R^{12}$, $R^{13}$ or $R^{14}$;
$R^{11}$ is phenyl which is unfused or fused with benzene, heteroarene or $R^{11A}$; $R^{11A}$ is cycloalkane, cycloalkene, heterocycloalkane or heterocycloalkene;
$R^{12}$ is heteroaryl which is unfused or fused with benzene, heteroarene or $R^{12A}$; $R^{12A}$ is cycloalkane, cycloalkene, heterocycloalkane or heterocycloalkene;
$R^{13}$ is cycloalkyl, cycloalkenyl, heterocycloalkyl or heterocycloalkenyl, each of which is unfused or fused with benzene, heteroarene or $R^{13A}$; $R^{13A}$ is cycloalkane, cycloalkene, heterocycloalkane or heterocycloalkene;
$R^{14}$ is alkyl, alkenyl or alkynyl, each of which is unsubstituted or substituted with one, two, three, four or five of independently selected $R^{15}$, $OR^{15}$, $SR^{15}$, $S(O)R^{15}$, $SO_2R^{15}$, $NH_2$, $NHR^{15}$, $N(R^{15})_2$, $C(O)R^{15}$, $C(O)NH_2$, $C(O)NHR^{15}$, $C(O)N(R^{15})_2$, $NHC(O)R^{15}$, $NR^{15}C(O)R^{15}$, $NHSO_2R^{15}$, $NR^{15}SO_2R^{15}$, $NHC(O)OR^{15}$, $NR^{15}C(O)OR^{15}$, $SO_2NH_2$, $SO_2NHR^{15}$, $SO_2N(R^{15})_2$, $NHC(O)NH_2$, $NHC(O)R^{15}NHC(O)N(R^{15})_2$, $NR^{15}C(O)N(R^{15})_2$, OH, (O), C(O)OH, CN, $CF_3$, $OCF_3$, $CF_2CF_3$, F, Cl, Br or I;
$R^{15}$ is $R^{16}$, $R^{17}$, $R^{18}$ or $R^{19}$;
$R^{16}$ is phenyl which is unfused or fused with benzene, heteroarene or $R^{15A}$; $R^{15A}$ is cycloalkane, cycloalkene, heterocycloalkane or heterocycloalkene;
$R^{17}$ is heteroaryl which is unfused or fused with benzene, heteroarene or $R^{16A}$; $R^{16A}$ is cycloalkane, cycloalkene, heterocycloalkane or heterocycloalkene;

$R^{18}$ is cycloalkyl, cycloalkenyl, heterocycloalkyl or heterocycloalkenyl, each of which is unfused or fused with benzene, heteroarene or $R^{18A}$; $R^{18A}$ is cycloalkane, cycloalkene, heterocycloalkane or heterocycloalkene;

$R^{19}$ is alkyl, alkenyl or alkynyl, each of which is unsubstituted or substituted with $R^{20}$;

$R^{20}$ is phenyl, heteroaryl, cycloalkyl, cycloalkenyl or heterocycloalkyl;

wherein $R^{11}$, $R^{12}$, $R^{13}$, $R^{16}$, $R^{17}$, and $R^{18}$ are independently unsubstituted or substituted with one or two or three or four or five of independently $OR^{21}$, $NO_2$, $CF_3$, F, Cl, Br or I; and $R^{21}$ is alkyl, alkenyl, alkynyl, phenyl, heteroaryl, cycloalkyl, cycloalkenyl or heterocycloalkyl.

2. The compound of claim 1, wherein $R^2$ is heteroaryl;

$R^3$ is heterocycloalkyl;

$R^4$ is alkyl substituted with $OR^5$;

$R^5$ is $R^6$, $R^7$, $R^8$ or $R^9$, $R^6$ is phenyl which is unfused or fused with benzene, heteroarene or $R^{6A}$; $R^{6A}$ is cycloalkane;

$R^7$ is heteroaryl;

$R^8$ is cycloalkyl, cycloalkenyl, heterocycloalkyl or heterocycloalkenyl;

$R^9$ is alkyl, alkenyl or alkynyl, each of which is unsubstituted or substituted with one, two, three, four or five of independently selected $R^{9A}$, $OR^{9A}$, $SR^{9A}$, $S(O)R^{9A}$, $SO_2R^{9A}$, $NH_2$, $NHR^{9A}$, $N(R^{9A})_2$, $C(O)R^{9A}$, $C(O)NH_2$, $C(O)NHR^{9A}$, $C(O)N(R^{9A})_2$, $NHC(O)R^{9A}$, $NR^{9A}C(O)R^{9A}$, $NHSO_2R^{9A}$, $NR^{9A}SO_2R^{9A}$, $NHC(O)OR^{9A}$, $NR^{9A}C(O)OR^{9A}$, $SO_2NH_2$, $SO_2NHR^{9A}$, $SO_2N(R^{9A})_2$, $NHC(O)NH_2$, $NHC(O)R^{9A}NHC(O)N(R^{9A})_2$, $NR^{9A}C(O)N(R^{9A})_2$, OH, (O), C(O)OH, CN, $CF_3$, $OCF_3$, $CF_2CF_3$, F, Cl, Br or I;

$R^{9A}$ is $R^{9B}$, $R^{9C}$ or $R^{9D}$;

$R^{9B}$ is phenyl;

$R^{9C}$ is heteroaryl;

$R^{9D}$ is cycloalkyl, cycloalkenyl, heterocycloalkyl or heterocycloalkenyl;

wherein each foregoing cyclic moiety is independently unsubstituted or substituted with one or two or three independently selected $R^{10}$, $OR^{10}$, $C(O)R^{10}$, $NO_2$,)N$(R^{10})_2$, $C(O)NHR^{10}$, $SO_2N(R^{10})_2$, C(O)OH, OH, (O), $CF_3$, $OCF_3$, F, Cl, Br or I;

$R^{10}$ is $R^{11}$, $R^{12}$, $R^{13}$ or $R^{14}$;

$R^{11}$ is phenyl which is unfused or fused with benzene;

$R^{12}$ is heteroaryl;

$R^{13}$ is cycloalkyl, cycloalkenyl, heterocycloalkyl or heterocycloalkenyl;

$R^{14}$ is alkyl, alkenyl or alkynyl, each of which is unsubstituted or substituted with one, two, three, four or five of independently selected $R^{15}$, $OR^{15}$, $SR^{15}$, $S(O)R^{15}$, $SO_2R^{15}$, $NH_2$, $NHR^{15}$, $N(R^{15})_2$, $C(O)R^{15}$, $C(O)NH_2$, $C(O)NHR^{15}$, $C(O)N(R^{15})_2$, $NHC(O)R^{15}$, $NR^{15}C(O)R^{15}$, $NHSO_2R^{15}$, $NR^{15}SO_2R^{15}$, $NHC(O)OR^{15}$, $NR^{15}C(O)OR^{15}$, $SO_2NH_2$, $SO_2NHR^{15}$, $SO_2N(R^{15})_2$, $NHC(O)NH_2$, $NHC(O)R^{15}NHC(O)N(R^{15})_2$, $NR^{15}C(O)N(R^{15})_2$, OH, (O), C(O)OH, CN, $CF_3$, $OCF_3$, $CF_2CF_3$, F, Cl, Br or I;

$R^{15}$ is $R^{16}$, $R^{17}$, $R^{18}$ or $R^{19}$;

$R^{16}$ is phenyl;

$R^{17}$ is heteroaryl;

$R^{18}$ is cycloalkyl, cycloalkenyl, heterocycloalkyl or heterocycloalkenyl;

$R^{19}$ is alkyl, alkenyl or alkynyl, each of which is unsubstituted or substituted with $R^{20}$;

$R^{20}$ is phenyl, heteroaryl, cycloalkyl, cycloalkenyl or heterocycloalkyl;

wherein $R^{11}$, $R^{12}$, $R^{13}$, $R^{16}$, $R^{17}$, and $R^{18}$ are independently unsubstituted or substituted with one or two or three or four or five of independently $OR^{21}$, $NO_2$, $CF_3$, F, Cl, Br or I; and $R^{21}$ is alkyl, alkenyl, alkynyl, phenyl, heteroaryl, cycloalkyl, cycloalkenyl or heterocycloalkyl.

3. The compound of claim 2 wherein $R^5$ is $R^6$, $R^7$, or $R^8$;

$R^6$ is phenyl which is unfused or fused with benzene, heteroarene or $R^{6A}$; $R^{6A}$ is cycloalkane;

$R^7$ is heteroaryl;

$R^8$ is cycloalkyl, cycloalkenyl, heterocycloalkyl or heterocycloalkenyl;

wherein each foregoing cyclic moiety is independently unsubstituted or substituted with one or two or three independently selected $R^{10}$, $OR^{10}$, $C(O)R^{10}$, $NO_2$, $N(R^{10})_2$, $C(O)NHR^{10}$, $SO_2N(R^{10})_2$, C(O)OH, OH, (O), $CF_3$, $OCF_3$, F, Cl, Br or I;

$R^{10}$ is $R^{11}$, $R^{13}$ or $R^{14}$;

$R^{11}$ is phenyl which is unfused or fused with benzene;

$R^{13}$ is heterocycloalkyl;

$R^{14}$ is alkyl or alkenyl, each of which is unsubstituted or substituted with one, two, three, four or five of independently selected $R^{15}$, $OR^{15}$, $SO_2R^{15}$, $N(R^{15})_2$, F, Cl, Br or I;

$R^{15}$ is $R^{16}$, $R^{18}$ or $R^{19}$;

$R^{16}$ is phenyl;

$R^{18}$ is heterocycloalkyl;

$R^{19}$ is alkyl;

wherein $R^{11}$ and $R^{16}$ are independently unsubstituted or substituted with one or two or three or four or five of independently $OR^{21}$, $NO_2$, $CF_3$, F, Cl, Br or I; and $R^{21}$ is alkyl.

4. A composition comprising an excipient and a therapeutically effective amount of a compound of claim 1.

5. A compound selected from the group consisting of 1-(3-(1-naphthyloxy)propyl)-3-piperidin-1-yl-1H-indole-2-carboxylic acid;

3-morpholin-4-yl-1-(3-(1-naphthyloxy)propyl)-1H-indole-2-carboxylic acid;

3-(4-carboxypiperidin-1-yl)-1-(3-(1-naphthyloxy)propyl)-1H-indole-2-carboxylic acid; and 1-(3-(1-naphthyloxy)propyl)-3-(1,3,5-trimethyl-1H-pyrazol-4-yl)-1H-indole-2-carboxylic acid;

or a therapeutically acceptable salt thereof.

6. The compound of claim 1, where $B^1$ is 3-(1-naphthyloxy)propyl.

7. 1-(3-(1-Naphthyloxy)propyl)-3-(1,3,5-trimethyl-1H-pyrazol-4-yl)-1H-indole-2-carboxylic acid or a therapeutically acceptable salt thereof.

* * * * *

UNITED STATES PATENT AND TRADEMARK OFFICE
CERTIFICATE OF CORRECTION

PATENT NO. : 7,981,888 B2  
APPLICATION NO. : 12/104319  
DATED : July 19, 2011  
INVENTOR(S) : Song et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 53 days.

Signed and Sealed this
Twenty-second Day of November, 2011

David J. Kappos
*Director of the United States Patent and Trademark Office*

UNITED STATES PATENT AND TRADEMARK OFFICE
CERTIFICATE OF CORRECTION

PATENT NO. : 7,981,888 B2
APPLICATION NO. : 12/104319
DATED : July 19, 2011
INVENTOR(S) : Xiaohong Song et al.

It is certified that error appears in the above-identified patent and that said Letters Patent is hereby corrected as shown below:

In The Claims:

Column 8, Claim 2, Line 43 please revise – "independently selected $R^{10}$, $OR^{10}$, $C(O)R^{10}$, $NO_2$,)N" to read as --independently selected $R^{10}$, $OR^{10}$, $C(O)R^{10}$, $NO_2$, N--

Signed and Sealed this
Eighth Day of May, 2012

David J. Kappos
*Director of the United States Patent and Trademark Office*

SEQUENCE LISTING

<160> NUMBER OF SEQ ID NOS: 1

<210> SEQ ID NO 1
<211> LENGTH: 20

```
<212> TYPE: PRT
<213> ORGANISM: Artificial Sequence
<220> FEATURE:
<223> OTHER INFORMATION: Assay protein
<220> FEATURE:
<221> NAME/KEY: MOD_RES
<222> LOCATION: 1
<223> OTHER INFORMATION: Gly is modified with 6-FAM
<220> FEATURE:
<221> NAME/KEY: MOD_RES
<222> LOCATION: 20
<223> OTHER INFORMATION: Phe is modified with amide

<400> SEQUENCE: 1

Gly Glu Leu Glu Val Glu Phe Ala Thr Gln Leu Arg Arg Phe Gly Asp
 1               5                  10                  15

Lys Leu Asn Phe
            20
```